US009528920B2

(12) United States Patent
Hale

(10) Patent No.: US 9,528,920 B2
(45) Date of Patent: *Dec. 27, 2016

(54) ASPIRATION-FREE WELL PLATE APPARATUS AND METHODS

(71) Applicant: CytoSaver LLC, Palo Alto, CA (US)

(72) Inventor: Matthew B. Hale, Redwood City, CA (US)

(73) Assignee: Cytosaver LLC, Palo Alto, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 14/635,386

(22) Filed: Mar. 2, 2015

(65) Prior Publication Data

US 2015/0168278 A1 Jun. 18, 2015

Related U.S. Application Data

(62) Division of application No. 14/215,645, filed on Mar. 17, 2014, now Pat. No. 8,968,682.

(Continued)

(51) Int. Cl.
*G01N 1/40* (2006.01)
*G01N 1/34* (2006.01)
(Continued)

(52) U.S. Cl.
CPC ............. *G01N 1/4005* (2013.01); *B01J 8/006* (2013.01); *B01L 3/50255* (2013.01); *G01N 1/34* (2013.01); *G01N 1/40* (2013.01); *G01N 1/4077* (2013.01); *B01D 61/18* (2013.01); *B01D 63/16* (2013.01); *B01D 2315/02* (2013.01);
(Continued)

(58) Field of Classification Search
CPC . G01N 1/4005; B01L 3/50255; Y10T 436/255
See application file for complete search history.

(56) References Cited

U.S. PATENT DOCUMENTS 4,948,564 A 8/1990 Root et al.
5,141,719 A 8/1992 Fernwood et al.
(Continued)

FOREIGN PATENT DOCUMENTS

EP 1 953 552 A1 8/2008
WO WO 01/78895 A2 10/2001

OTHER PUBLICATIONS

International Search Report and Written Opinion for PCT/US2014/030320, mailed on Aug. 8, 2014, 8 pages.
(Continued)

*Primary Examiner* — P. Kathryn Wright
(74) *Attorney, Agent, or Firm* — Cooley LLP

(57) ABSTRACT

A well plate includes a including a top portion, a bottom portion and a membrane disposed between the top portion and the bottom portion. The top portion defines a sample well in fluid communication with an opening defined by the membrane and in fluid communication with a reservoir defined by the bottom portion. The well plate is configured to be used in a centrifugation process of a test sample including a sample material and a wash liquid. The test sample configured to be received within the sample well and the reservoir. The membrane configured to filter the wash liquid from the test sample during the centrifugation process such that the wash liquid can pass from the reservoir, through the membrane and can be captured within a collection chamber while the sample material remains within the reservoir.

18 Claims, 40 Drawing Sheets

Related U.S. Application Data

(60) Provisional application No. 61/787,554, filed on Mar. 15, 2013.

(51) Int. Cl.
| | | |
|---|---|---|
| *B01J 8/00* | (2006.01) | |
| *B01L 3/00* | (2006.01) | |
| *G01N 35/00* | (2006.01) | |
| *B01D 61/18* | (2006.01) | |
| *B01D 63/16* | (2006.01) | |

(52) U.S. Cl.
CPC . *B01L 2200/028* (2013.01); *B01L 2200/0631* (2013.01); *B01L 2200/0652* (2013.01); *B01L 2300/0829* (2013.01); *B01L 2400/0409* (2013.01); *G01N 2001/4088* (2013.01); *G01N 2035/00495* (2013.01); *Y10T 436/255* (2015.01)

(56) References Cited

U.S. PATENT DOCUMENTS

| | | |
|---|---|---|
| 6,338,802 B1 | 1/2002 | Bodner et al. |
| 8,968,682 B2 | 3/2015 | Hale |
| 2003/0219360 A1 | 11/2003 | Olivier |
| 2004/0089615 A1 | 5/2004 | Weiss et al. |
| 2005/0095175 A1 | 5/2005 | Desilets et al. |
| 2005/0161400 A1 | 7/2005 | Pitt et al. |
| 2005/0191759 A1 | 9/2005 | Pedersen-Bjergaard et al. |
| 2009/0143572 A1 | 6/2009 | Inomata et al. |
| 2013/0065771 A1 | 3/2013 | Oroskar et al. |

OTHER PUBLICATIONS

European Search Report for Application No. 14764523.8, mailed on Oct. 24, 2016, 7 pages.

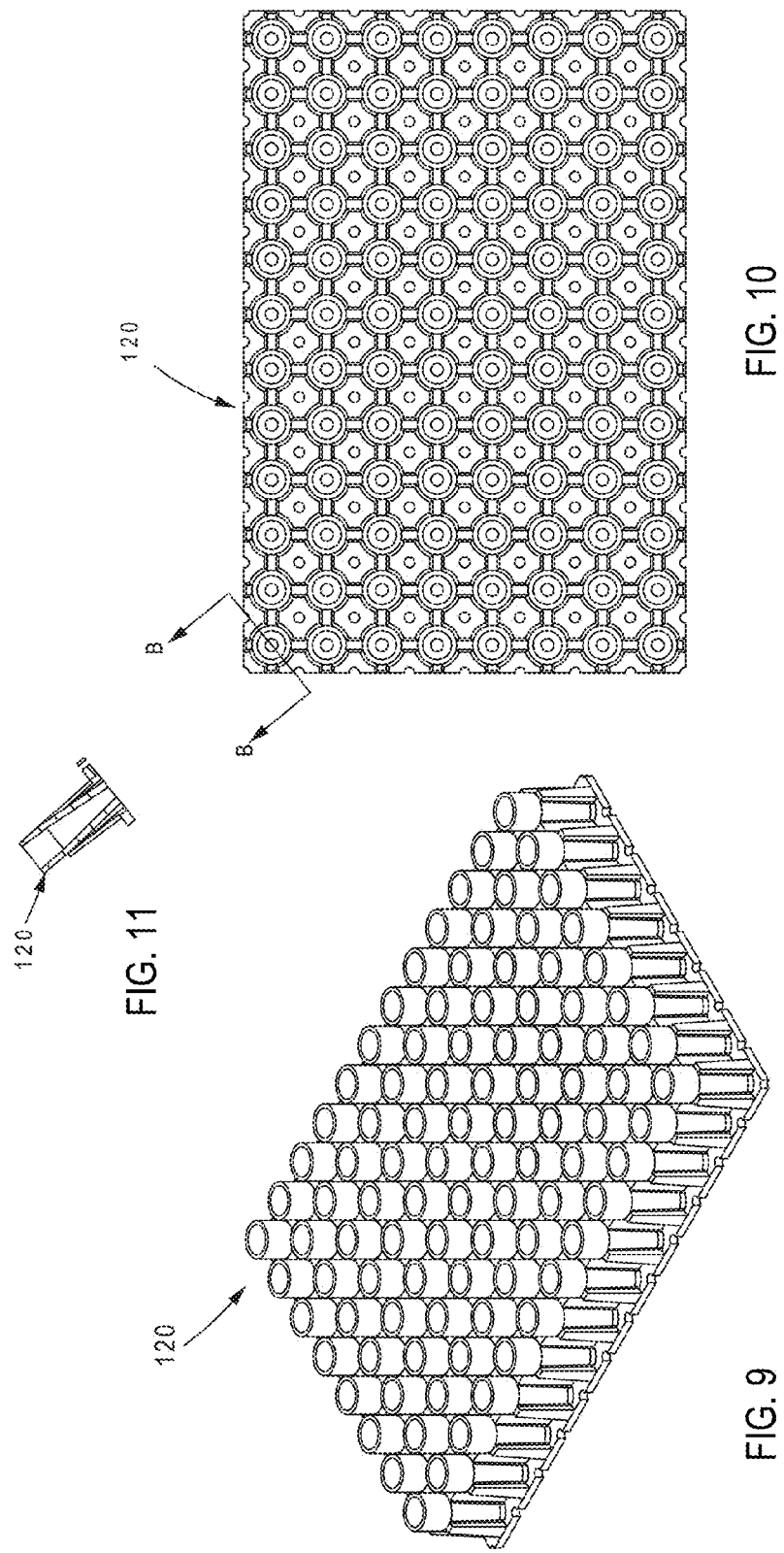

ASPIRATION-FREE WELL PLATE APPARATUS AND METHODS

CROSS-REFERENCE TO RELATED APPLICATIONS

This application is a divisional of U.S. patent application Ser. No. 14/215,645, entitled "Aspiration-Free Well Plate Apparatus and Methods," filed Mar. 17, 2014, which claims priority to and the benefit of U.S. Provisional Patent Application No. 61/787,554, entitled "Aspiration-Free Well Plate Apparatus and Methods," filed Mar. 15, 2013, the disclosures of which are incorporated herein by reference in their entirety.

BACKGROUND

Embodiments described herein relate generally to biological testing devices and more particularly, to apparatus and methods of using test plates having multiple wells for holding multiple samples to be used in analytical testing fields.

Cellular assays typically require exposing cells to a series of different liquids with different properties, usually referred to as culture media, buffers, stains, staining cocktails, fixatives, permeabilization agents, and similar liquids. The cells are exposed to a series of different liquids by removing the cells from the majority of the current liquid and then adding the next successive liquid in the series. This is typically done in the following manner: cells suspended in their current liquid are transferred to a tube or to the wells of a well plate, and then spun in a centrifuge at a speed sufficient to generate a centripetal acceleration that can pull the cells to the bottom of the well (e.g., between about 200 relative centrifugal force (rcf) and about 600 rcf) to form what is known as a "pellet". The liquid (supernatant) can then be decanted or aspirated and discarded, leaving the cell pellet at the bottom of the tube or well in a relatively small residual volume of the liquid. The next liquid in the series can then be added into a volume that is much larger than the residual volume of the last liquid, and as such, the cells can be exposed almost exclusively to the new liquid.

A known problem with this approach, however, is that a fraction of the cells can be lost each time the sample is centrifuged and the liquid fraction removed by decanting or aspiration. This problem is compounded by starting with a very small cell number (e.g., fewer than 200,000 cells) because the stability of the pellet is proportional to the number of cells in the pellet. For example, at low cell numbers the pellet resulting from centrifugation is unstable and an unacceptably large fraction of the sample is lost when the supernatant is discarded by decanting or aspiration. As many experiments may require five or more serially performed centrifugation steps, with some requiring more than twenty centrifugation steps, it may be impractical to work with low cell numbers if a high fraction of the starting cell number must be recovered at the end of all of the centrifugation steps. This is problematic for the growing number of applications involving limited sample material, including analysis of biological samples from pediatric patients or cells derived from certain biopsies or clinical aspirates. In particular, primary stem cells or derived stem cells are usually available in very small numbers and the quantity that can be used in an assay may be as low as 5,000 cells, or lower. Conventional centrifugation and aspiration or decanting approaches are poorly suited for cell numbers as low as 5,000 as, in some instances, effectively none of the cells can be recovered. Many cell types, and stem cells in particular, are sensitive to the high centripetal acceleration force required by conventional methods.

An alternative approach has been developed for bead-based assays where the bottom of the wells of a well plate include a porous membrane. Such well plates can be centrifuged or placed on a manifold that uses a vacuum to pull the liquid fraction through the bottom of the plate. Unfortunately, when cells are used in these membrane-bottomed cell plates a high fraction of the cells become irretrievably stuck in the membrane material, even when using state-of-the-art low-binding membranes making this unsuitable for many downstream cellular assays.

An additional problem of the conventional methods mentioned above is that the supernatant that is separated from the cells may contain biohazardous elements, such as infectious viruses like Hepatitis, HIV, or other agents. Conventional methods decant the supernatant or aspirate the supernatant to transfer it to a vessel that contains chemicals that neutralize the biohazardous elements. The process of decanting or aspirating of the supernatant carries a risk of exposing the person performing the assay to the biohazards in the supernatant. Eliminating the need to decant or aspirate the supernatant can reduce this risk.

Thus, there is a need for an effective way to repeatedly wash cells without substantially losing cells in each wash step. In addition, there is a need for a way to effectively deal with a biohazardous supernatant by minimizing handling. Also, there is a need for an effective way to reduce centrifugation forces on the cells to increase cell viability, while still maintaining high sample separation and recovery.

SUMMARY

Apparatus and methods of using test tubes or plates having one or more wells (e.g., multi-well plates) for holding one or more samples to be used in analytical testing fields are described herein. In some embodiments, a well plate includes a top portion, a bottom portion and a membrane disposed between the top portion and the bottom portion. The top portion defines a sample well in fluid communication with an opening defined by the membrane and in fluid communication with a reservoir defined by the bottom portion. The well plate is configured to be used in a centrifugation process of a test sample including a sample material and a wash liquid. The test sample is configured to be received within the sample well and the reservoir. The membrane is configured to filter the wash liquid from the test sample during the centrifugation process such that the wash liquid can pass from the reservoir, through the membrane and can be captured within a collection chamber, while the sample material remains within the reservoir.

BRIEF DESCRIPTION OF THE DRAWINGS

FIGS. 9 and 10 are a perspective view and a top view, respectively, of the top plate of FIG. 2.

FIG. 11 is a cross-sectional view of a portion of the top plate taken along line B-B in FIG. 10.

DETAILED DESCRIPTION

Figure 1:
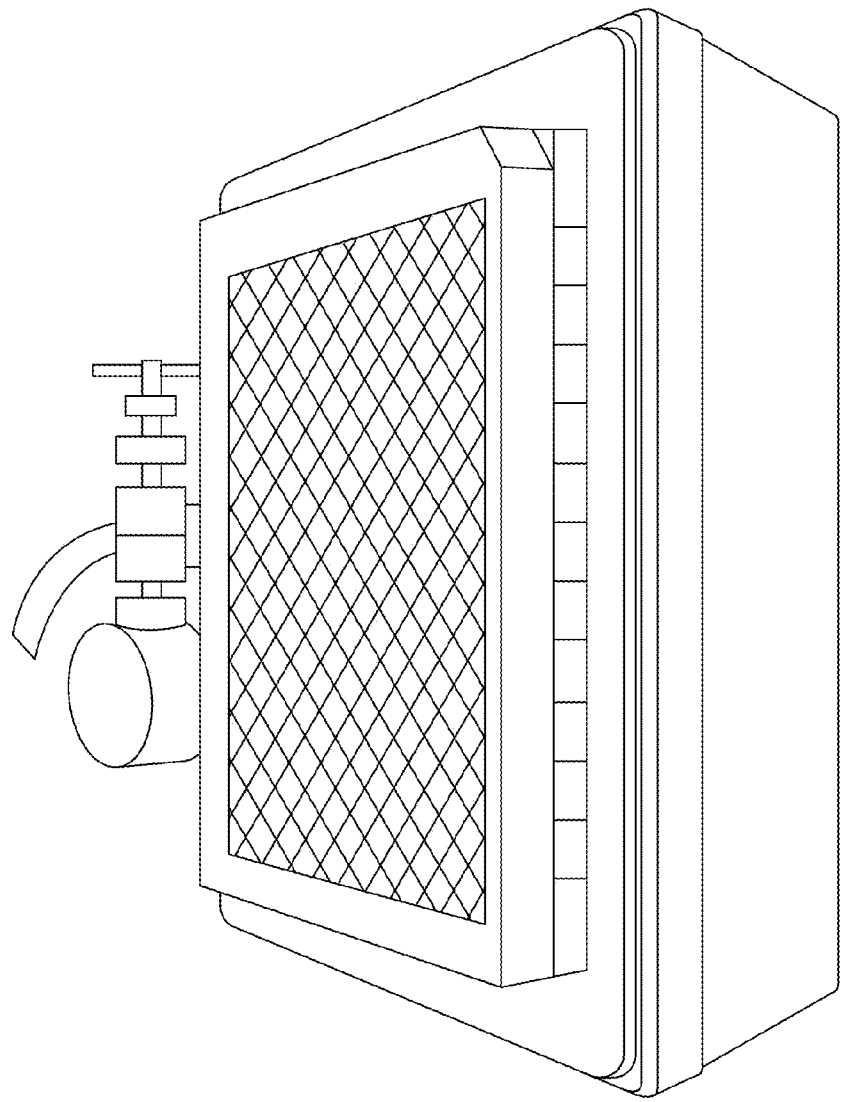
FIG. 1 is an illustration of a known well plate with a manifold for drawing liquid through the bottom of the well plate.

Apparatus and methods of using test tubes or plates having one or more wells (e.g., multi-well plates) for holding one or more samples to be used in analytical testing fields are described herein. In some embodiments, a well plate includes a top portion, a bottom portion and a membrane disposed between the top portion and the bottom portion. The top portion defines a sample well in fluid communication with an opening defined by the membrane and in fluid communication with a reservoir defined by the bottom portion. The well plate is configured to be used in a centrifugation process of a test sample including a sample material and a wash liquid. The test sample is configured to be received within the sample well and the reservoir. The membrane is configured to filter the wash liquid from the test sample during the centrifugation process such that the wash liquid can pass from the reservoir, through the membrane and can be captured within a collection chamber, while the sample material remains within the reservoir.

In some embodiments, a well plate includes a set of sample wells each in fluid communication with a reservoir from a set of reservoirs, and a membrane at least partially disposed between the set of sample wells and the set of reservoirs. The membrane defines a set of openings that are each in fluid communication with a different sample well from the set of sample wells and a different reservoir from the set of reservoirs. Each sample well from the set of sample wells and each reservoir from the set of reservoirs is configured to receive a test sample including a test material and a wash liquid. The membrane is configured to filter the wash liquid from each test sample disposed within the set of sample wells and the set of reservoirs during a centrifugation process such that the wash liquid can pass from each reservoir from the set of reservoirs through the membrane to be captured within a collection chamber, while the sample material of each test sample remains within the respective reservoir from the set of reservoirs.

In some embodiments, a tube assembly includes a sleeve member, a top tube, a base member, and a membrane. The top tube is configured to be received at least partially within an interior region of the sleeve member, and the membrane is disposed between a portion of the top tube and the base member. The top tube defines a sample well in fluid communication with an opening defined by the membrane and a reservoir defined by the base member. The tube assembly is configured to be used in a centrifugation process of a test sample, which includes a sample material and a wash liquid. The test sample is configured to be received through the sample well to be disposed within the reservoir. The membrane is configured to filter the wash liquid from the sample material during the centrifugation process such that the wash fluid can pass up through the membrane and into a collection chamber defined by the sleeve member, while the sample material remains within the reservoir.

Apparatus and methods are described herein for use in testing and analysis of assays including cells, or particles similar in size to cells. In some embodiments, a device such as those described herein can be used for assays involving cells or particles, and methods can be used for preparing samples by repeated washing and centrifugation, such as those described herein. For example, a device such as those described herein can be used with cells and/or particles that have a diameter between 0.5 micron and 50 microns. In one example use, any of the devices described herein can be used to test and analyze cells and/or particles having a diameter between 2 microns and 20 microns, which is the size of most mammalian leukocytes.

Apparatus and methods are described herein that can be used during centrifugation to test sample cells and particles. During centrifugation, the wash liquid used during the testing process can be captured within a collection chamber of the apparatus or device. Thus, the need to aspirate or decant the wash liquid can be reduced or eliminated. In some embodiments, a well plate assembly can include a top plate, a bottom plate and a membrane disposed between the top plate and the bottom plate. The well plate assembly can be used in a centrifugation process for cells and/or particles. During the centrifugation process, while the cells are drawn to a bottom reservoir portion of the well plate assembly, the wash liquid (e.g., effluent) can rise from the reservoir, be filtered through the membrane, and directed through drain holes of the well plate assembly and captured in a collection chamber. In some embodiments, an absorbent member can be disposed within the collection chamber to capture the wash liquid therein. In some embodiments, the absorbent member can be impregnated with chemicals that can neutralize biohazards in the wash liquid or effluent within the collection chamber.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together (e.g., via a weld, an adhesive, or any suitable method).

As used herein, the term "sample" refers to a composition whose contents and/or constituents are to be tested. A sample can be heterogeneous, containing a variety of components (e.g., different proteins) or homogenous, containing one component. In some instances, a sample can be naturally occurring, a biological material, and/or a man-made material. Furthermore, a sample can be in a native or denatured form. In some instances, a sample can be a single cell (or contents of a single cell) or multiple cells (or contents of multiple cells), a blood sample, a tissue sample, a skin sample, a urine sample, culture media, bovine serum albumen, antibodies, cytokines, small molecule drugs, quantum dots, oligonucleotides, fluorophores, fixatives, and/or the like. In some instances, a sample can be from a living organism, such as a eukaryote, prokaryote, mammal, human, yeast, and/or bacterium or the sample can be from a virus. In some instances, a sample can be one or more stem cells (e.g., any cell that has the ability to divide for indefinite periods of time and to give rise to specialized cells). Suitable examples of stem cells can include but are not limited to embryonic stem cells (e.g., human embryonic stem cells (hES)), and non-embryonic stems cells (e.g., mesenchymal, hematopoietic, induced pluripotent stem cells (iPS cells), or adult stem cells (MSC)).

The embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polypropylene, polyesters, polycarbonates, polyethersulfone, polyacrylates, polymers of ethylene-vinyl acetates and other acyl substituted cellulose acetates, non-degradable polyurethanes, polystyrenes, polyvinyl chloride, polyvinyl fluoride, poly (vinyl imidazole), chlorosulphonate polyolefins, polyethylene oxide, and/or blends and copolymers thereof.

Figure 2:
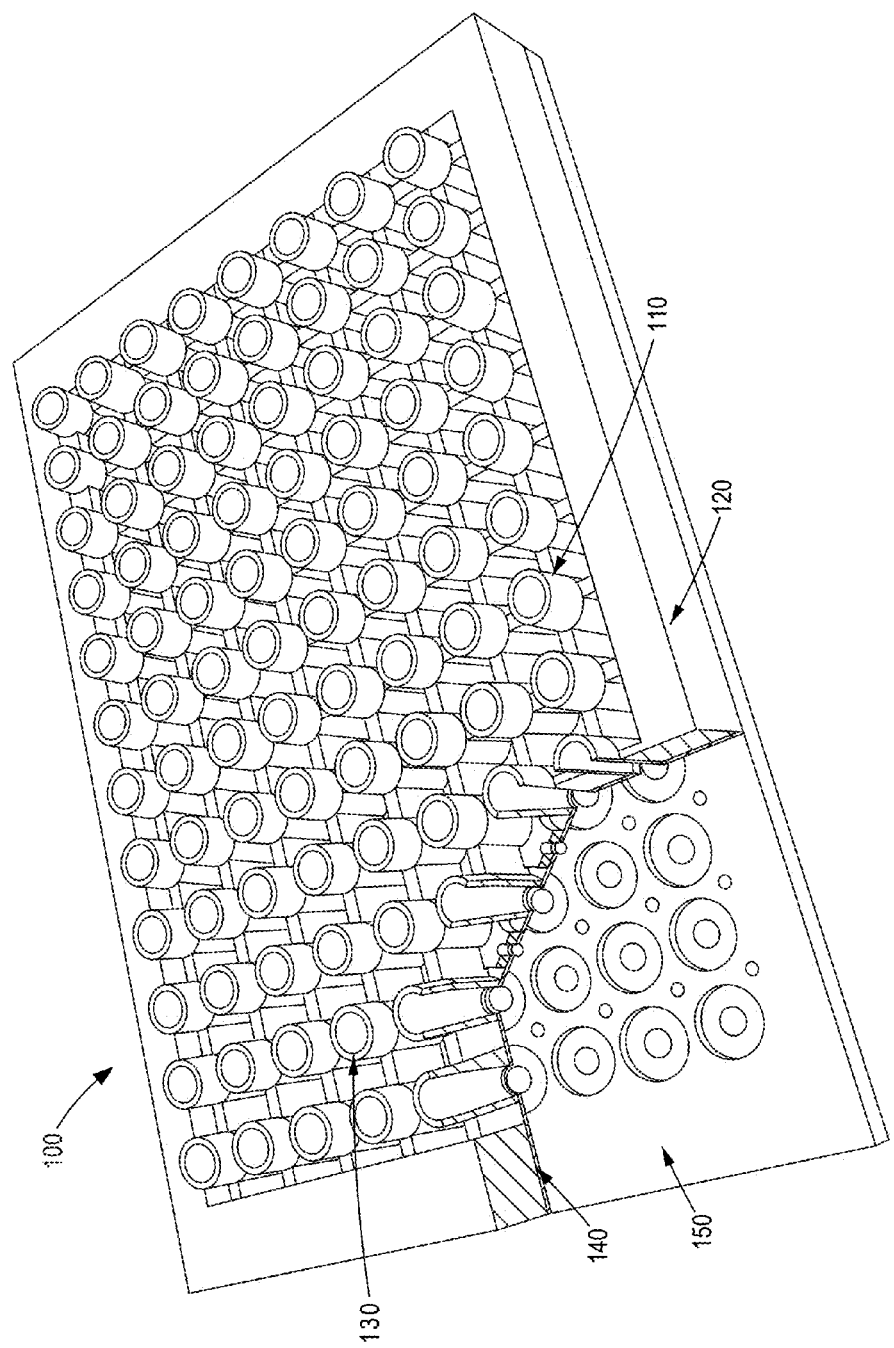
FIG. 2 is a perspective view of a well plate assembly, according to an embodiment, with a portion of the well plate of the plate assembly removed to show inner details.

FIG. 1 is a perspective view of a known well plate assembly provided for reference. FIG. 2 is a perspective view of a well plate assembly 100, according to an embodiment. FIG. 2 illustrates the well plate assembly 100 with a portion removed for illustration purposes. Well plate assembly 100 (also referred to herein as "plate assembly") can include multiple wells 110 in which an assay can be disposed. In this embodiment, the plate assembly 100 includes 96 wells disposed, for example, in an 8×12 arrangement.

Well plate assembly 100 includes a top plate 120, a bottom plate 150 and a microporous membrane 140 disposed between the top plate 120 and the bottom plate 150. Top plate 120 and bottom plate 150 can be formed with a suitable material(s), such as, for example, polystyrene, nylon, polypropylene, polyethylene therethalate, polypropylene, polyethylene, polysulphone, polyethersulfone, polytetrafluoroethylene (PTFE), cellulose acetate, and/or polyvinylidene fluoride. Top plate 120 and bottom plate 150 can each be formed, for example, by an injection molding process, machining, 3D printing or other suitable manufacturing techniques. In some embodiments, top plate 120 and bottom plate 150 are monolithically formed, although it should be understood that they can be formed to include multiple components and/or multiple different materials. In some embodiments, bottom plate 150 can be formed with a transparent glass material that is suitable for use with assay techniques that require light transmission, such as, for example, with microscopy, while top plate 120 can be formed with a transparent plastic material or, alternatively, an opaque, anti-reflective plastic material. In another example, the top plate 120 can be formed such that each well 110 is formed with a highly-inert plastic material, such as, for example, PTFE, and is molded over a support material or, alternatively, press-fit into or molded within a second plastic support material to make top plate 120. Although this embodiment is shown as a standard 96 well plate, it should be understood that the features described herein can be scaled and applied to any other size well plate size including, for example, arrays of 4, 6, 9, 24, 384, and 1536 wells or even as a single well tube. In some embodiments, the top plate 120 and the bottom plate 150 are separately formed by injection molding.

Membrane 140 can be formed with a substantially planar microporous sheet. In some embodiments, the membrane 140 can be formed with a material such that the membrane 140 is a barrier to the passage of cells, but allows liquid to pass through with little impedance. Such membranes can include, but are not restricted to, hydrophilic membranes including those used in plasmapheresis such as polyethersulfone membranes with a pore size between, for example, 0.2 micron and 2 microns and that are considered "low-binding" in that proteins and cells do not readily stick to them. In some embodiments, the pore size is smaller than the diameter of the cells that are to be retained in the sample well (e.g., most leukocytes are approximately 8 microns in diameter), but large enough to allow reagents that exit the plate assembly 100 to pass through the membrane 140. For example, such reagents can include, but are not limited to, human serum constituents, culture media, bovine serum albumen, antibodies, cytokines, small molecule drugs, quantum dots, oligonucleotides, fluorophores, fixatives, alcohols, and isotopes appropriate for mass cytometry chelated and attached to polymers. Additionally, the membrane 140 can be formed with a material such that the membrane 140 is chemically compatible with the reagents and wash liquids to be used in the assay process. Membrane 140 may be made of a material that has low cell adhesion and other properties that reduce cells being bound to the membrane itself.

In some embodiments, the membrane 140 can be a hydrophilic membrane that can be used with aqueous wash solutions that readily wet out and reduce the effect of meniscus formation. In some embodiments, the membrane 140 can be a hydrophobic membrane that can be used when it is desirable to have low water absorption and with nonaqueous solutions. Choosing a membrane material with a high transmembrane flow rate may be advantageous and one such membrane is a Type 6F sold by Membrana GmbH, Wuppertal, Germany, which has a transmembrane flow of greater than 90 milliliters/(minute square centimeter bar). The type of membrane to use for a particular application can also depend on the liquids to be used in that application. For example, some assays may involve liquids that may interact unfavorably with the particular membrane.

In some embodiments, the membrane 140 can be formed as a porous polypropylene membrane, which although it can be less hydrophilic can still be used for plasmapheresis in some settings. The membrane 140 can be formed with a variety of different materials, such as, for example, various polymers, including polypropylene, polyethylene, polysulphone, polyethersulfone, polytetrafluoroethylene, regenerated cellulose, cellulose acetate, polyvinylidene fluoride, and others.

Top plate 120 and bottom plate 150 can be coupled together by conventional methods, including those typically used to assemble filter plates. Such coupling methods can include, for example, ultrasonic welding, insert molding, co-molding, press-fitting, thermal adhesion, and/or adhesives, such as, epoxies, urethanes and polyurethanes. The membrane 140 can be disposed between the top plate 120 and the bottom plate 150 and be coextensive with the perimeter edges of the top plate 120 and bottom plate 150, as shown, for example, in FIG. 2, or can be slightly smaller to allow the edges to be ultrasonically welded around the perimeter of the top plate 120 and bottom plate 150. Alternatively, the membrane 140 may be pre-cut into an array of pieces, each large enough for a single well. The membrane 140 can be bonded to the top plate 120, the bottom plate 150 and/or to both the top plate 120 and the bottom plate 150. In some embodiments, mechanical fasteners (not shown in FIGS. 1-14), such as, for example, screws, bolts, and/or clips can be used in addition to or alternatively to join the top plate 120 and the bottom plate 150 together. In other embodiments, the top plate 120 and the bottom plate 150 can be formed such that they can be press-fit together or snapped together without adhesive or fasteners.

Figure 3:
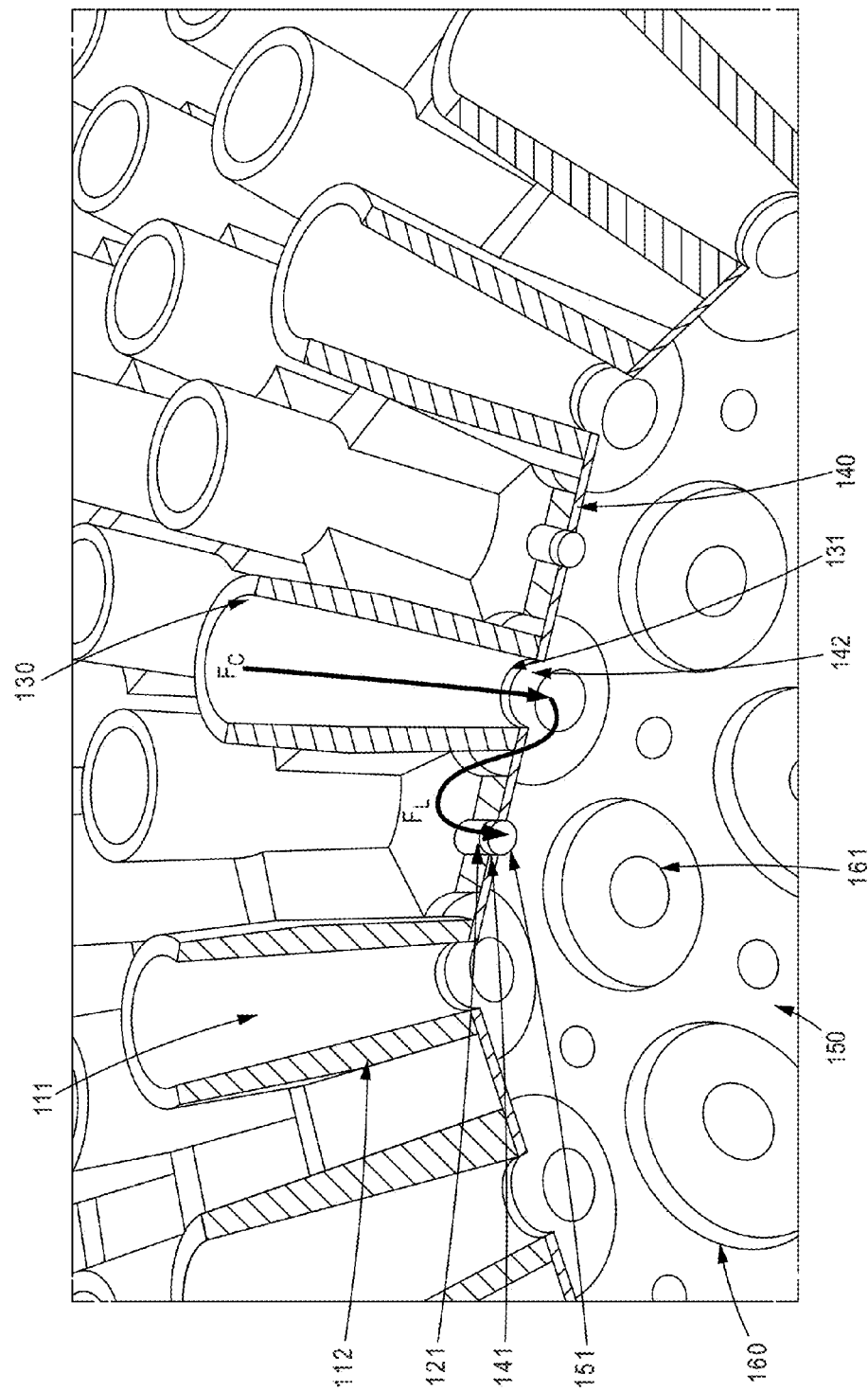
FIG. 3 is an enlarged perspective view of a portion of the well plate assembly of FIG. 2.

FIG. 3 illustrates a detailed cut-away section of the top plate 120 and membrane 140, which exposes a portion of the bottom plate 150 for illustration purposes. As shown in FIG. 3, the top plate 120 defines top openings 130 and bottom openings 131 each in fluid communication with the interior volume 111 of the wells 110 through which an assay can be inserted into the well 110. The top plate 120 also defines drain holes 121. The membrane 140 defines openings 142 that are substantially centrally aligned with openings 131 of the top plate 120. The bottom plate 150 defines a reservoir 160 with a recessed portion 161 and drain holes 151. The drain holes 121 of the top plate are in fluid communication with drain holes 141 defined in the membrane 140, which are each in fluid communication with one of the bottom plate drain holes 151. The drain holes 121, drain holes 141 and drain holes 151 can be the same or different diameter and can be at least partially aligned or concentric with each other. While illustrated as generally u-shaped, the reservoir 160 and/or the recessed portion 161 can be any shape. For example, the reservoir 160 and/or the recessed portion 161 can be conically shaped, c-shaped, or v-shaped. In some embodiments, different recessed portions can have different shapes depending on, for example, the intended use of the well plate and the volume of cells to be collected, for example.

In use, in some applications where the well plate assembly 100 is to be centrifuged, a wash liquid along with cells or particles to be tested can be disposed within an interior volume 111 (also referred to herein as "well column") of the wells 110. While being centrifuged, as shown by flow directional arrow $F_C$ in FIG. 3, the cells are drawn to a bottom portion of the well column 111 by centripetal force, through opening 131 and opening 142 and into the reservoir 160 of the bottom plate 150. As shown by flow directional arrow $F_L$ in FIG. 3, the wash liquid separates from the cells and in an effort to meet equilibrium raises up through a portion of the membrane 140 to a top surface of the top plate 120 between the wells 110. The wash liquid can then pass through the top plate drain hole 121, through the membrane drain hole 141, and then through the bottom plate drain hole 151 and into a collection chamber (not shown) disposed, for example, below the bottom plate 150. For example, in some embodiments, the well plate assembly 100 can include a collection chamber or tray to collect the wash liquid that separates from the cells during the centrifugation process and drops down through the drain holes 121, 141 and 151. The collection tray can be integrated into a one-piece assembly by attachment to the bottom of the bottom plate 150, or can be a removable tray that can be manually emptied after each centrifugation step. An example of such a tray is described with respect to well plate assemblies 300 and 400 herein (see, e.g., FIGS. 17, 18 and 21).

Centripetal acceleration directly opposes the flow of liquid out of the reservoir 160 and through membrane 140, thus forcing the cells away from the membrane 140 and to a bottom portion of the reservoir 160. The level of the remaining supernatant in the well column 111 can be equal to a height of the top plate drain hole 121. The height of the entrance to top plate drain hole 121 can act as a weir, and by adjusting this height above the membrane 140, the amount of the remaining supernatant in the well column 111 after centrifugation can be adjusted. The cells or particles within the well 110 can collect or "pellet" in the reservoir 160 of the bottom plate 150, and in particular, within the recessed portion 161 of the reservoir 160. The size of the pores in the membrane 140 can be too small to allow the cells to pass up through the membrane 140 with the wash liquid during centrifugation. The forces that bind cells and other particles irretrievably to the membrane as a consequence of liquid flowing through the membrane must be adequately opposed by the centripetal acceleration acting on these particles. This requires optimization of the device such that the well height above the membrane, reservoir geometry, membrane material, membrane pore size, and functional membrane surface area per well is optimized to ensure that liquid does not flow through the membrane until sufficient centripetal acceleration is achieved and so that the rate of the flow through the membrane and other factors that would irretrievably bind particles to the membrane are adequately opposed by centripetal acceleration.

Figure 4:
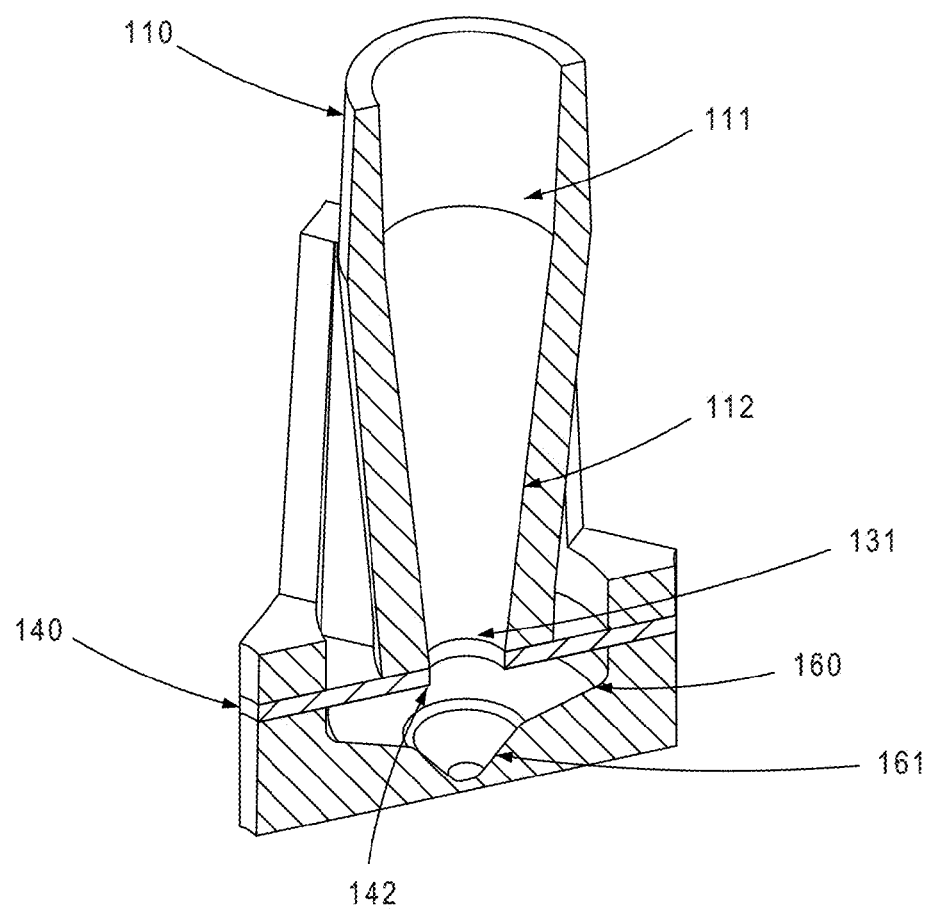
FIG. 4 is a detailed cut-away view of a well of the well plate assembly of FIG. 2.
Figure 7:
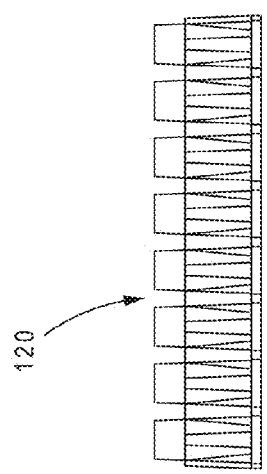
FIGS. 5-8 are a top view, a bottom view, a right side view, and a front view, respectively, of the top plate of FIG. 2.
Figure 8:
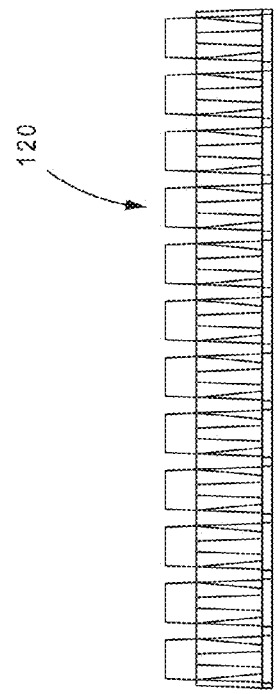

FIG. 4 is a detailed section view of a well 110 of well plate assembly 100. As shown in FIG. 4, the inner walls 112 of the wells 110 are tapered such that a diameter of the well column 111 (e.g., interior volume) at a base opening 131 defined by the top plate 120 is less than a diameter of the well column 111 at top opening 130. The taper of the inner walls 112 can help concentrate the cells or particles in the central recessed portion 161 of the reservoir 160 and or increase the functional surface area of membrane 140 per well. The taper can also facilitate the top plate 120 releasing from the mold during an injection molding process of forming the top plate 120.

In some embodiments, the reservoir 160 in the bottom plate 150 is also tapered to direct the cells or particles to the center recessed portion 161. The recessed portion 161 is centrally located within the lowest portion of the reservoir 160. Cells or particles can first collect in the recessed portion 161, and depending on the quantity of cells or particles in the sample, can also fill other areas of the reservoir 160. Such a configuration allows cells to be readily accessed (e.g., by pipetting) through the well 110, directly into the reservoir 160.

Figure 5:
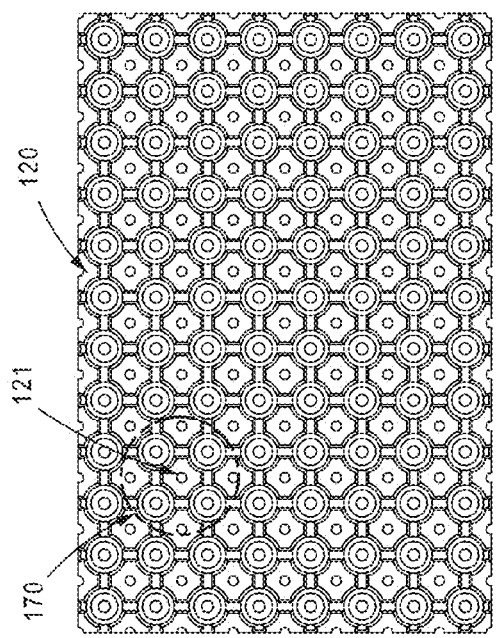
Figure 6:
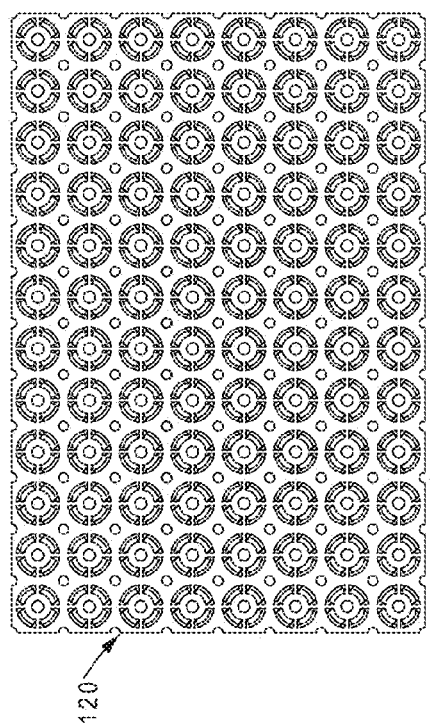
Figure 14:
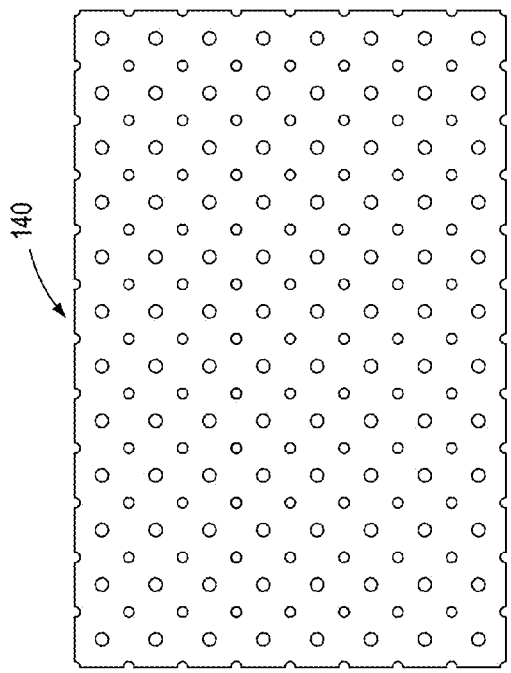
FIG. 14 is a top view of a membrane of the well plate assembly of FIG. 2.
Figure 13:
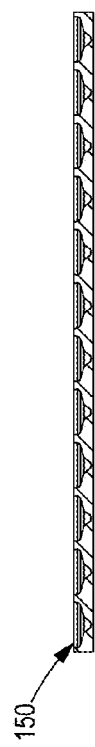
FIG. 13 is a cross-sectional view of the base plate taken along line-A-A in FIG. 12.
Figure 12:
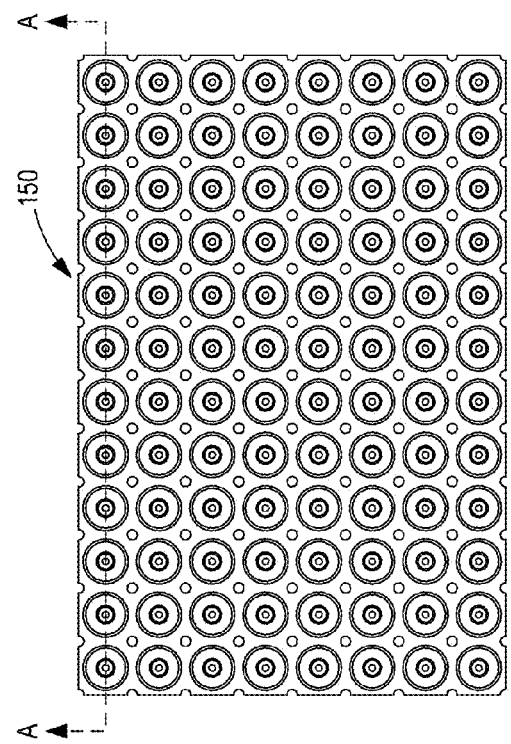
FIG. 12 is a top view of a base plate of the well plate assembly of FIG. 2.

FIGS. 5-8 are further illustrations of the plate assembly 100. The planar perimeter portion of the top plate 120 and the bottom plate 150 are not shown in FIGS. 5-8. As shown in FIG. 5, each square grouping of four wells 170 share a common top plate drain hole 121 located in the center of each grouping. FIG. 9 includes a perspective view of the top plate 120 and FIG. 10 is another top view of top plate 120. FIG. 11 is a section view B-B taken along line B-B in FIG. 10. FIGS. 12 and 13 are a top view and a side cross section view, respectively, of the bottom plate 150 and FIG. 14 is a top view of the membrane 140. Although plate assembly 100 includes a single membrane 140 that extends beneath all wells 110, in some embodiments, the well assembly 100 can include multiple membranes each disposed beneath a single well 110 of the top plate 120.

Figure 15:
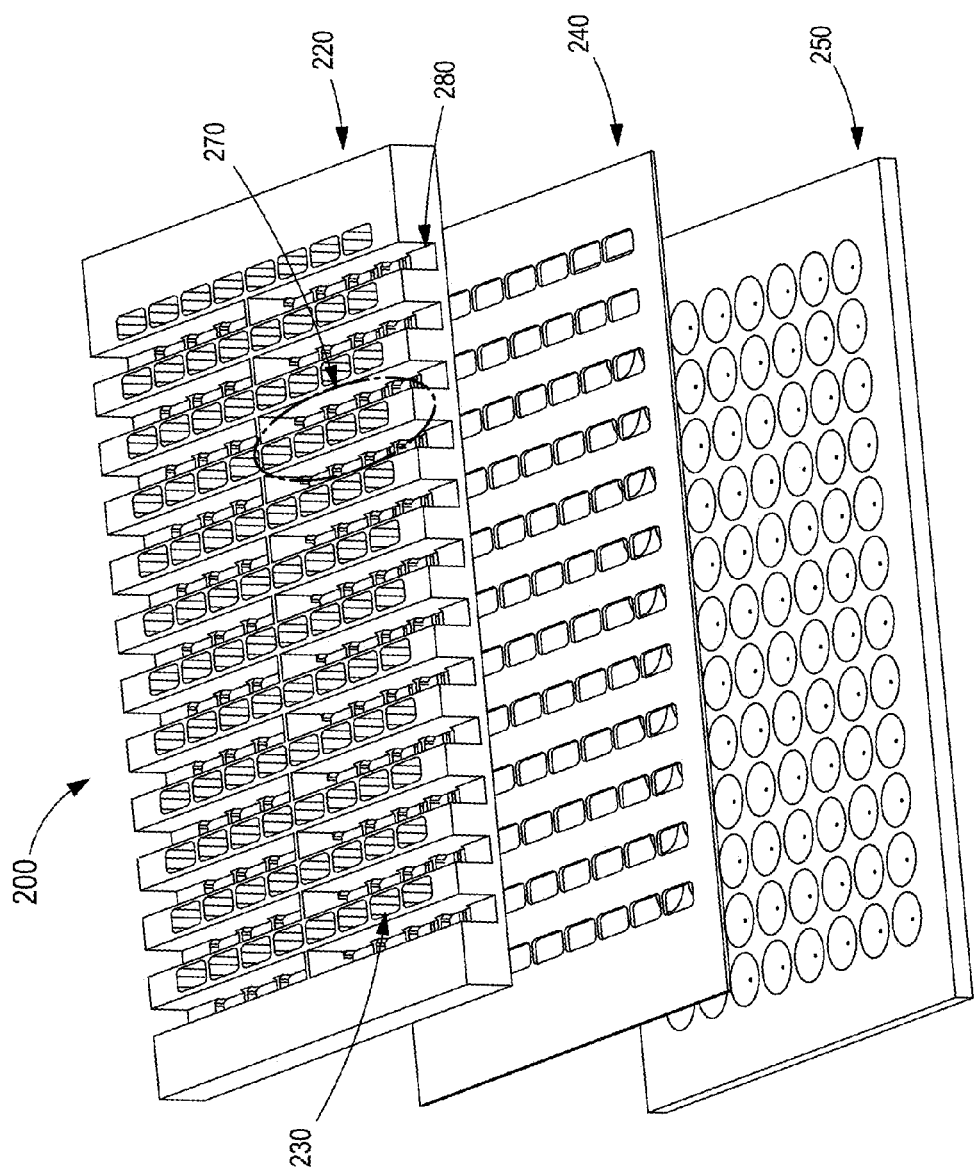
FIG. 15 is an exploded view of a well plate assembly, according to another embodiment.

FIG. 15 is an exploded view of another embodiment of a well plate assembly. A well plate assembly 200 (also referred to herein as "plate assembly") includes a top plate 220, a microporous membrane 240, and a bottom plate 250. The top plate 220, bottom plate 250, and membrane 240 can be coupled together in the same or similar manner as described above for well plate assembly 100. Each of the top plate 120, bottom plate 150 and membrane 140 can also be formed the same or similar as described above for well plate assembly 100.

Figure 16:
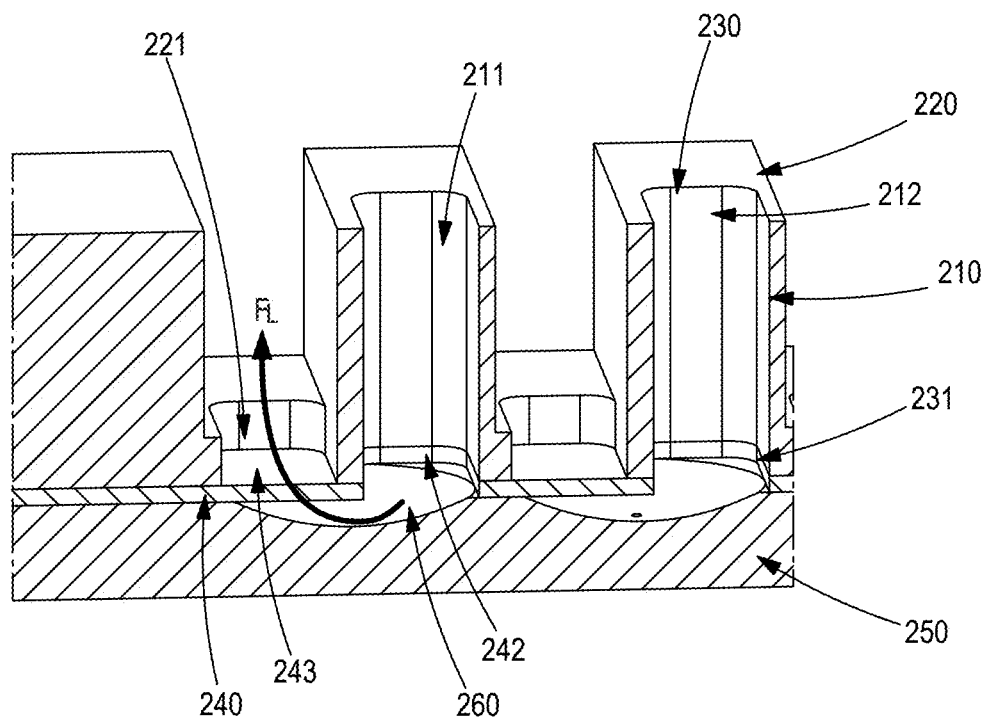
FIG. 16 is a detailed cross-sectional view of a portion of the well plate assembly of FIG. 15.

The top plate 220 includes multiple wells 210 and defines multiple drain channels 280 that provide a common drain to a row or group of wells 270. For example, a common drain channel 280 can be provided for a group of two, three, four, five, etc. wells. The supernatant that leaves the wells 210 through the membrane 240 is directed by the drain channels 280 to the edge of the top plate 220 where it drops off the top plate 220 and can be collected by a collection tray placed under the assembly (not shown). Drain holes as shown in assembly 100 are not required in the embodiment shown in plate assembly 200. Each of the wells 210 includes walls 212 that define a bore with an interior volume 211. In this embodiment, the shape of the bore is substantially rectangular. The wells 210 also define a top opening 230 and a base opening 231 each in fluid communication with the interior volume 211. FIG. 16 illustrates a detailed cross section of a well 210 of well plate assembly 200. In this embodiment, the interior walls 212 that define the interior volume 211 have a constant or substantially constant shape and size (e.g., are not tapered) but could be tapered if required for ease of manufacturing. As shown in FIGS. 15 and 10, the interior walls 212 have a cross-section that is substantially rectangular.

The bottom plate 250 defines multiple reservoirs 260 disposed off-center of the well bottom openings 230. In this embodiment, membrane 240 defines multiple apertures 242 that correspond to the shape of the interior volume 211 defined by walls 212 of top plate 220. As shown in FIG. 16, the top plate 220 defines membrane windows 221 that are each disposed over a portion 243 of the membrane 240 such that liquid can drain up through the membrane 240 as shown by directional arrow $F_L$, through the membrane windows 221 and into drain channels 280 (shown in FIG. 15) and thereby to the outside edge of the top plate 220. For example, although not shown, the well plate assembly 200 can also include a collection chamber or tray to collect the wash liquid that separates from the cells during the centrifugation process and is passed by the drain channels 280 to the outside edge of the top plate 220. The collection chamber can be at least partially defined by a tray disposed below the bottom plate 250.

Figure 17:
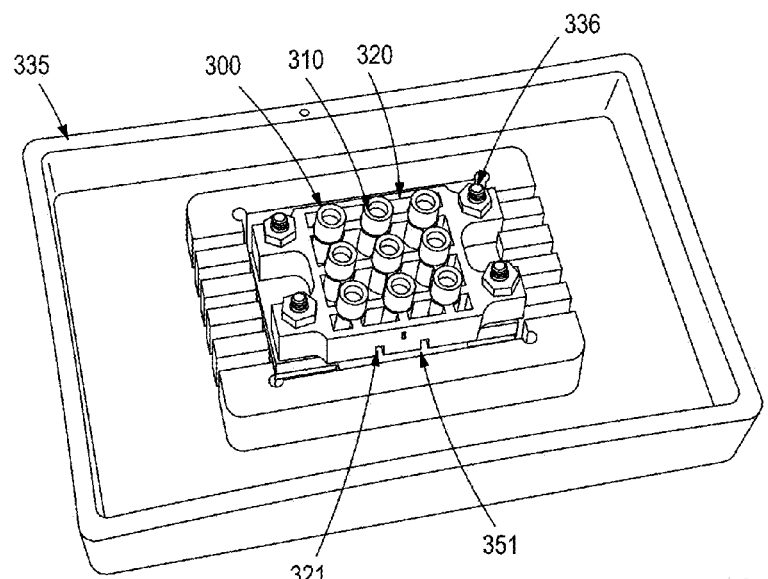
FIG. 17 is a perspective view of a well plate assembly, according to an embodiment and an effluent tray, according to an embodiment.
Figure 19:
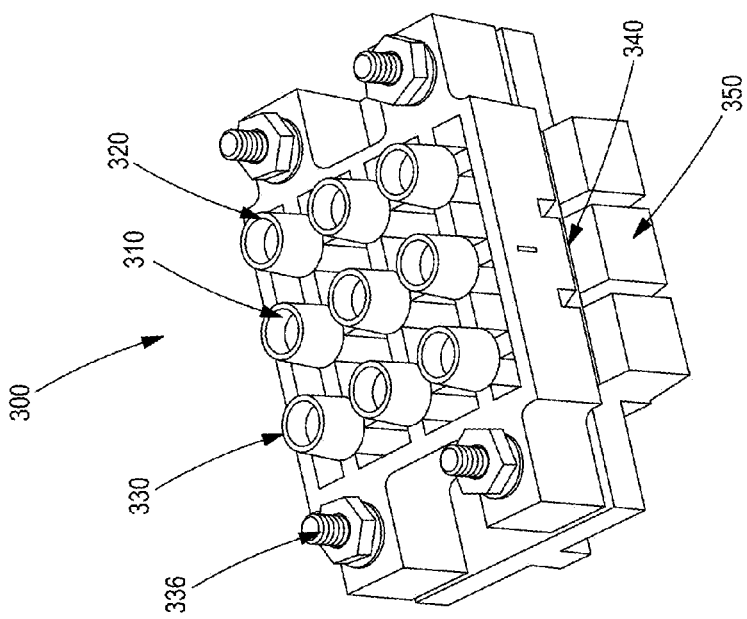
FIG. 19 is a perspective view of the well plate assembly of FIG. 17.

FIG. 17 shows another embodiment of a well plate assembly that is similar in design and function to the well plate assembly 100, but with only nine wells. A well plate assembly 300 includes a nine well array of wells 410 and is disposed on an effluent collection tray 335. As with previous embodiments, the well plate assembly 300 (also referred to herein as "plate assembly") includes a top plate 320, a bottom plate 350 and a membrane 340 (see, e.g., FIG. 19) disposed between the top plate 320 and the bottom plate 350. The top plate 320, bottom plate 350, and membrane 340 can be coupled together with adhesive and mechanical fasteners 336 as shown in FIGS. 17 and 19. Each of the top plate 120, bottom plate 150 and membrane 140 can also be formed the same or similar as described above for previous embodiments.

The top plate 320 includes wells 310 that define an interior region or volume and defines top openings 330 and bottom openings (not shown). The top plate 320 also includes drain holes 321. The membrane 340 includes an opening (not shown) that can be substantially aligned with the bottom opening of the top plate 320 and drain holes (not shown). The bottom plate 350 includes reservoirs (not shown) and drain holes 351, as described above for previous embodiments.

Figure 18:
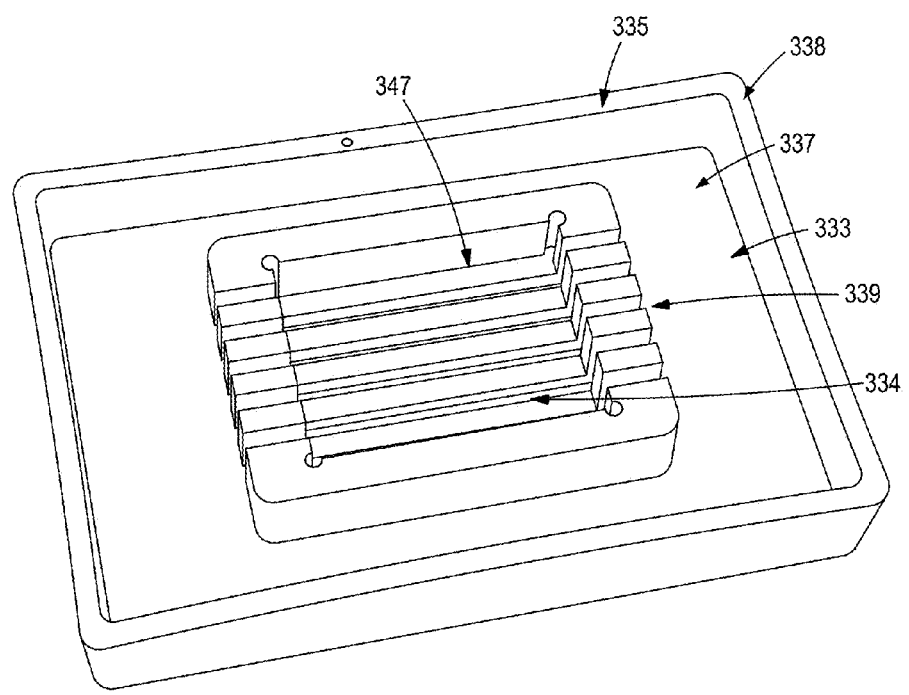
FIG. 18 is a top perspective view of the effluent tray of FIG. 17.

As shown in FIG. 17 the well plate assembly 300 can be disposed within an effluent collection tray (also referred to herein as "tray") 335. FIG. 18 is a top perspective view of the effluent collection tray 335. The effluent collection tray 335 includes a containment wall 338 that surrounds the perimeter of the tray 335 and defines a collection chamber 333 that can hold the effluent (e.g., wash liquid) that left the wells through the membrane 340 during centrifugation. A central platform 339 extends above a base 337 of the effluent collection tray 335 and defines an interior region 347 in which the plate assembly 300 can be disposed, as shown in FIG. 17. The platform 339 defines multiple channels 334, which allow the effluent to drain from the drain holes 321 and 351 and into the collection chamber 333 of the tray 335.

In use, samples placed in the wells 310 can pass through bottom openings (not shown) in the top plate 320, through the apertures (not shown) of the membrane 340 and into the reservoirs (not shown) of the bottom plate 350. During centrifugation, the cells can collect within the reservoirs of the bottom plate 350 and the effluent (e.g., wash liquid; also referred to as supernatant) can rise up through the membrane 340 and then out or down through the drain holes 321 of the top plate 320, the membrane drain holes (not shown), the bottom plate drain holes 351 and into the collection chamber 333 of the tray 335.

Figure 20:
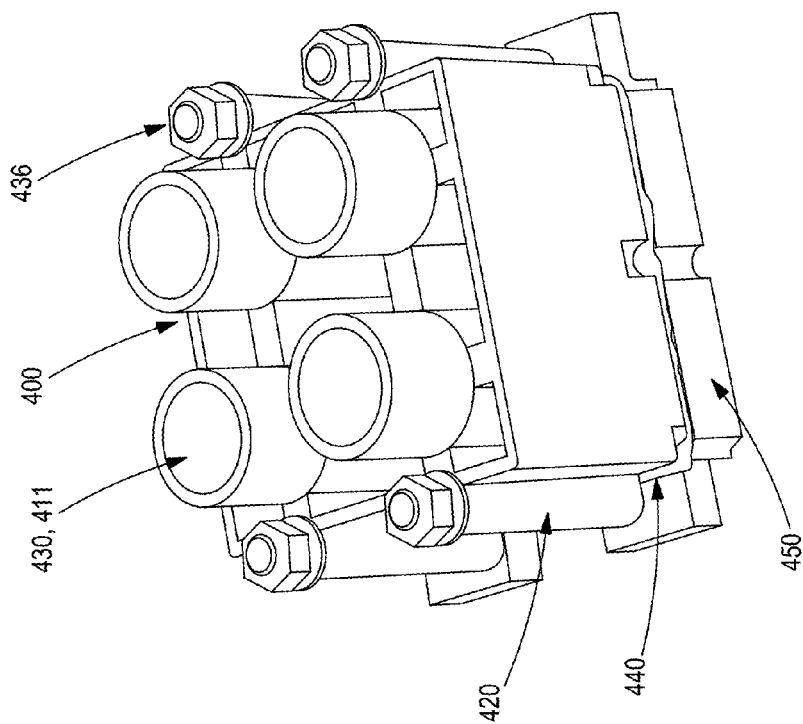
FIG. 20 is perspective view of a well plate assembly, according to another embodiment.
Figure 22:
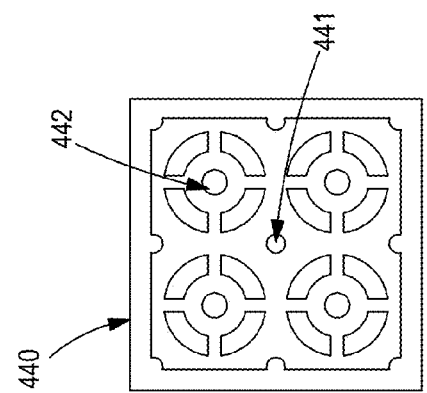
FIG. 22 is a top view of a membrane of the well plate assembly of FIG. 20.
Figure 21:
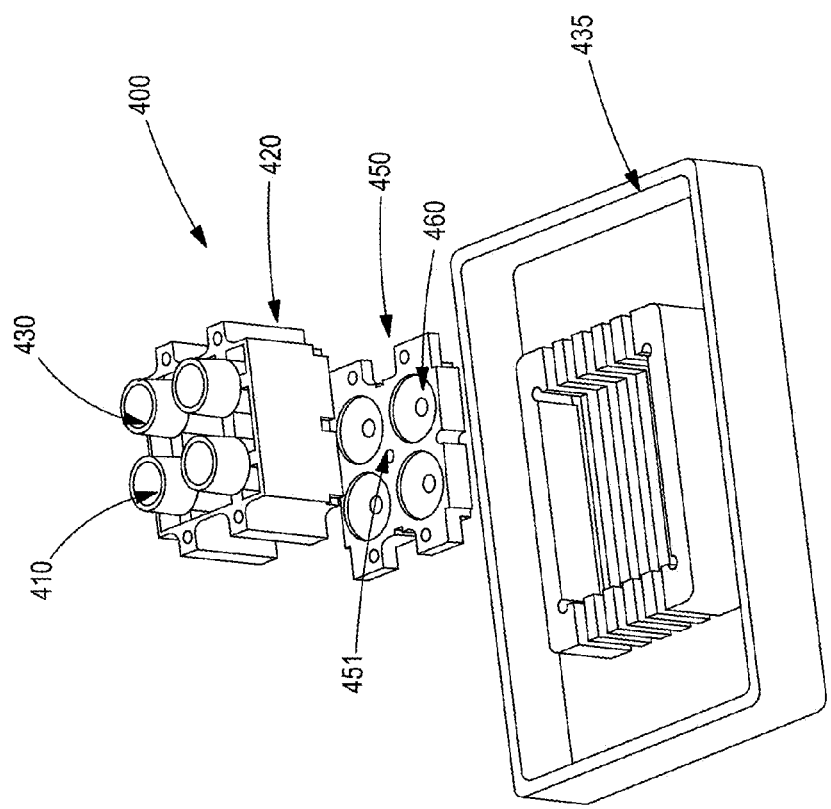
FIG. 21 is an exploded view of the well plate assembly of FIG. 20 and the effluent tray of FIG. 18.

FIGS. 20-22 illustrate a well plate assembly 400 that includes four wells 410. The well plate assembly 400 (also referred to herein as "plate assembly") includes a top plate 420, a bottom plate 450, and a membrane 440 disposed between the top plate 420 and the bottom plate 450. As with the previous embodiment, the top plate 420 can be coupled to the bottom plate 450 with fasteners 490. FIG. 22 is a top view of membrane 440. The plate assembly 400 can be used with an effluent tray 435 in a similar manner as described for plate assembly 300. The effluent tray 435 can include the same or similar features and functions as described for effluent tray 335. Each well 410 of the top plate 420 defines a top opening 430 and a base opening (not shown) each in fluid communication with an interior region 411 of the well 410. The top plate 420 can also define drain holes (not shown). The base plate 450 defines four reservoirs 460 that align with wells 410, and a drain hole 451.

The membrane 440 defines multiple well apertures 442 and multiple drain holes 441. The well apertures 442 can substantially align with the wells 410. In use, samples placed in the wells 410 can pass through the bottom opening (not shown) in the top plate and through the membrane well aperture 442 and into the reservoirs 460 of the bottom plate 450. During centrifugation, the effluent can pass up through the membrane 440, and then out through the top plate drain holes (not shown), the membrane drain hole 441, the drain holes 451 of the base plate 450 and into the effluent tray 435.

Figure 23:
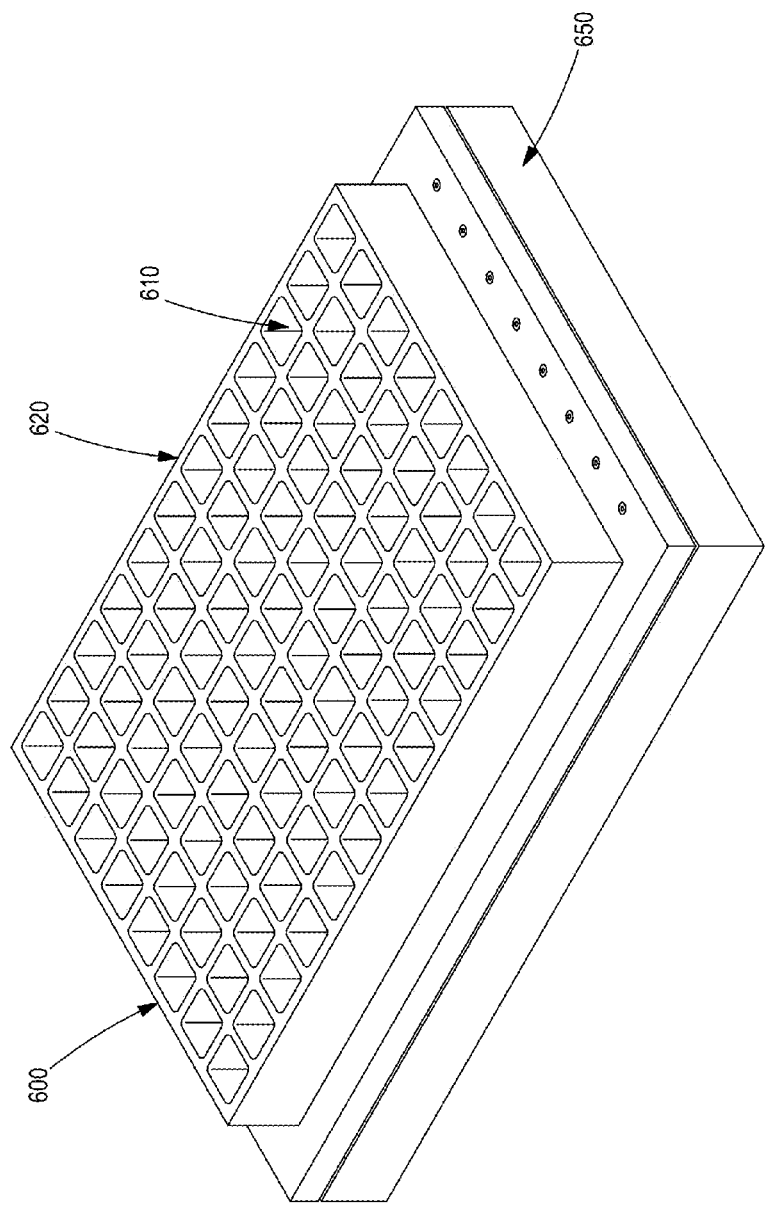
FIG. 23 is a perspective view of a well plate assembly, according to another embodiment.
Figure 24:
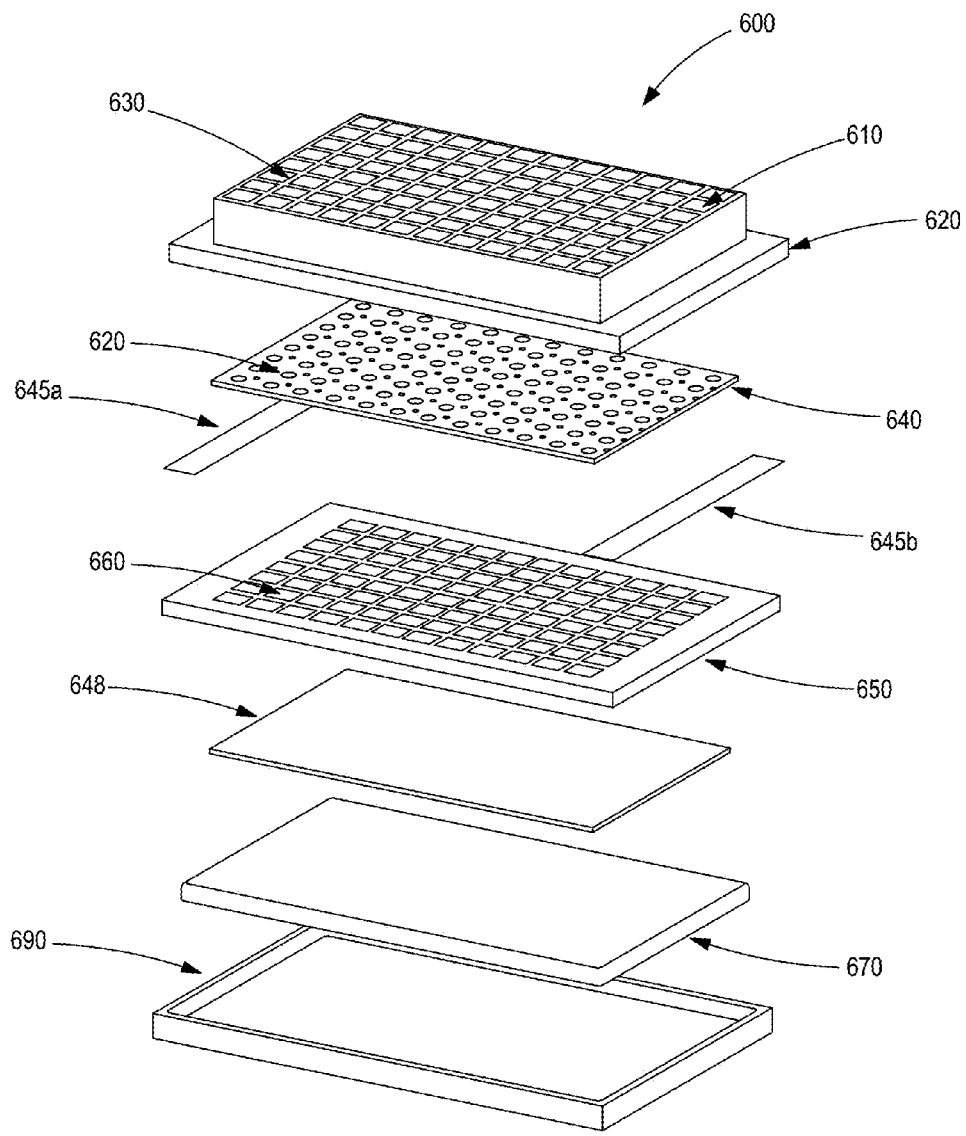
FIG. 24 is an exploded view of the well plate assembly of FIG. 23.
Figure 25:
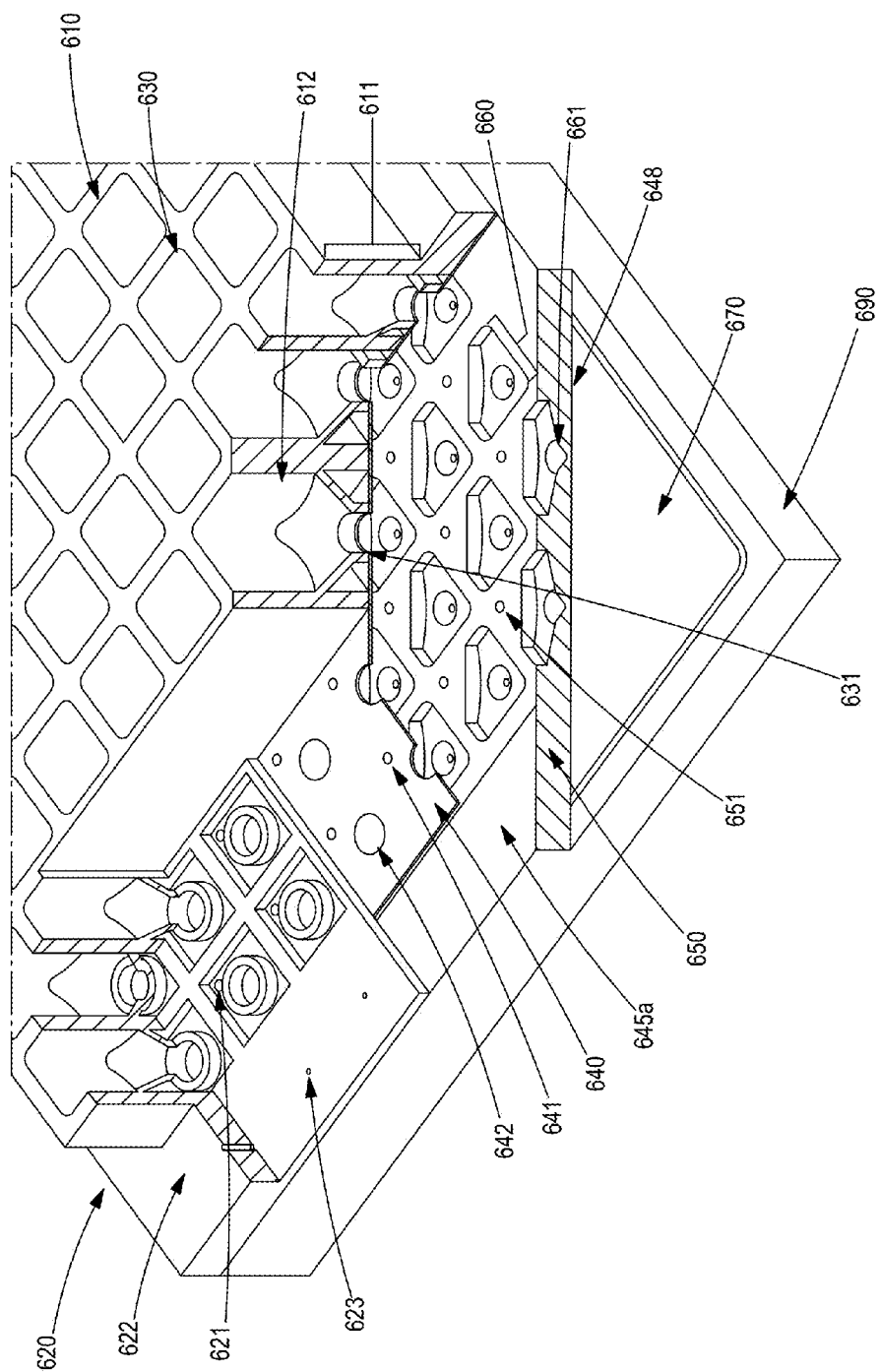
FIG. 25 is an enlarged view of a portion of the well plate assembly of FIG. 23 with a portion of the well plate assembly removed for illustration purposes.

FIGS. 23-25 illustrate another embodiment of a well plate assembly. A well plate assembly 600 includes 96 wells 610 in a standard 8×12 array configuration. An exploded view of well plate assembly 600 is shown in FIG. 24, and FIG. 25 is an enlarged view of a portion of the well plate assembly 600 with portions removed for illustration purposes. The well plate assembly 600 (also referred to herein as "plate assembly") includes a top plate 620, a bottom plate 650 and a membrane 640 disposed between the top plate 620 and the bottom plate 650. The top plate 620 includes a planar border portion or flange 622 that defines vent holes 623 as shown in FIG. 25. Samples can be introduced into wells 610 through a well top opening 630 defined by each of the wells 610. The wells 610 each have interior walls 612 that define a well bore or interior volume 611 that has a lightly-tapered top portion and a heavily-tapered bottom portion. In some embodiments, the well bore or interior volume 611 can have a non-tapered top portion and a tapered bottom portion. The top plate 620 also defines bottom openings 631 and drain holes 621.

The membrane 640 is a substantially planar sheet of microporous hydrophilic membrane material and defines membrane well apertures 642 and drain holes 641. A vent membrane shown in 645a and 645b is made of substantially planar sheets of a porous membrane that can filter air leaving a collection chamber (described in more detail below) when displaced by effluent flowing into the collection chamber. In some embodiments, the pore size of this air filtering vent membrane can be, for example, 0.2 microns. Bottom plate 650 defines drain holes 651 and well retention reservoirs 660 with recessed portions 661, and forms an upper portion of an effluent collection chamber of a collection tray 690 (described in more detail below). An optional effluent trapping membrane 648 can be a substantially planar hydrophobic membrane with defined micro-holes (not shown). An absorbent member 670 is disposed within the collection chamber of the tray 690 and can be impregnated with chemicals that neutralize biohazards in the effluent within the collection chamber.

The membrane 640 can be coupled to the top plate 620 and bottom plate 650 such that a liquid-tight seal is formed between the membrane 640 and the adjacent surfaces of the top plate 620 and the bottom plate 650. During use, cell suspensions and buffers can be loaded into the interior volume 611 of the wells 610 through openings 630, which define a top portion of the wells 610. In this embodiment, the wells 610 can be sized to hold, for example, over 730 microliters of liquid. When centrifuged at a rate greater than 100 rcf, for example, the liquid flows down through the well openings 631, through membrane well apertures 642 and into the well retention reservoir 660 in the bottom plate 650. The pressure generated by the centripetal acceleration acting on the column of liquid in the wells 610 forces the liquid up through the microporous membrane 640. The size of the pores in the membrane 640 can be too small to allow cells to pass through the membrane 640. Liquid that flows up through the membrane 640 can drain out through the top plate drain holes 621, through membrane drain holes 641, through bottom plate drain holes 651, through the microholes in effluent trapping membrane 648 (e.g., the hydrophobic membrane), and lastly into the absorbent material member 670 within the collection tray 690 where any biohazardous agents (such as, for example, viral or bacterial pathogens, etc.) in the effluent can be neutralized by chemicals in the absorbent material member 670 (e.g., formaldehyde, sodium hypochlorite, etc.).

After the height of the liquid in the wells 610 is no higher than the level of the top plate drain holes 621, the pressure generated by centripetal acceleration acting on the liquid in the wells 610 is no longer sufficient for liquid to pass through membrane 640. In this embodiment, the volume of liquid that remains in the well 610 (e.g., the residual volume) is slightly greater than the volume of the well retention reservoir 660, which can be, for example, 90 microliters. During centrifugation, the centripetal acceleration of well plate assembly 600 can pull the cells away from the membrane 640 and opposite the flow of the liquid through the membrane 640, and the cells can collect in the recessed portions 661 of reservoirs 660. This can minimize cells sticking to the membrane 640 and thereby minimizes cell loss, as well as membrane clogging.

The effluent trapping membrane 648 (e.g., hydrophobic membrane with micro-holes) is an optional component of the well plate assembly 600. The effluent trapping membrane 648, if employed, can function as a one-way valve such that effluent enters the collection chamber (defined by the bottom plate 650 and the tray 690) from the drain holes 651 in the bottom plate 650 driven by the centripetal acceleration generated during centrifugation, but cannot pass back through the drain holes 651 to the top plate 620 during normal handling, even if inverted, as the force of gravity alone is insufficient to make polar liquids pass through small diameter micro-holes in a hydrophobic membrane. During normal handling, effluent membrane 648 can help prevent liquids in the absorbent material member 670 from coming to the surface of the top plate 620 and possibly contaminating adjacent wells 610 by traveling back through membrane 640 and into the well collection reservoirs 660. The hydrophobic membrane has micro-holes aligned with the drain holes in the top plate. The sizes of the micro-holes are sufficient to allow efficient transfer of effluent into the collection chamber during centrifugation including any macromolecules in the effluent, but their small diameter coupled with the hydrophobic nature of the membrane prohibits polar liquids from passing back through during normal handling. The size of these micro-holes can be determined by the desired function and can in some embodiments be, for example, between 0.2 microns and 1000 microns.

The vent membrane 645a and 645b filters air displaced from the collection chamber to reduce or limit biohazardous elements from exiting the collection chamber as aerosol or as airborne particles.

Figure 27:
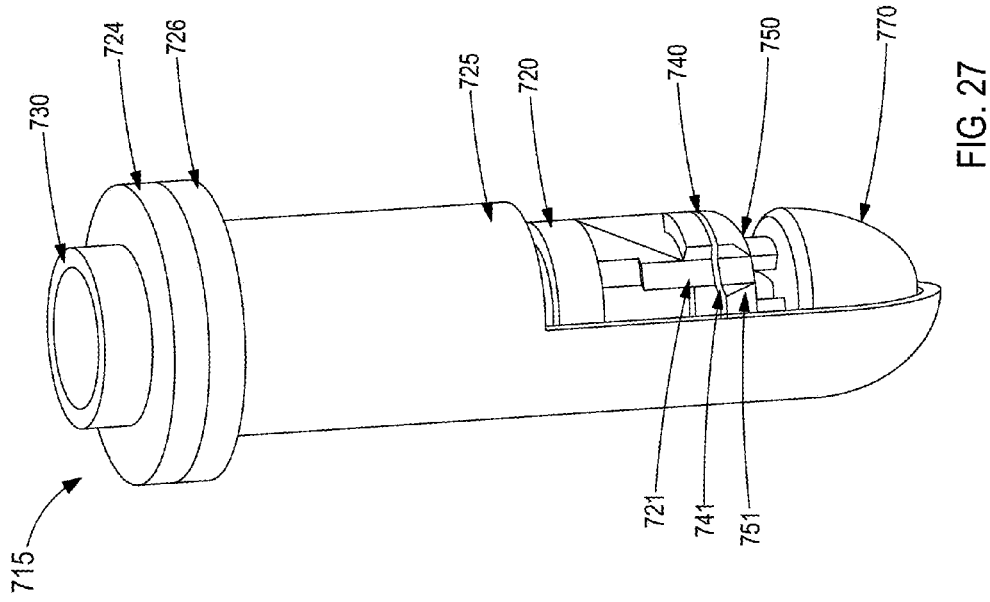
FIG. 27 is a perspective view of the tube assembly of FIG. 26, with a portion of the tub assembly removed for illustration purposes.
Figure 26:
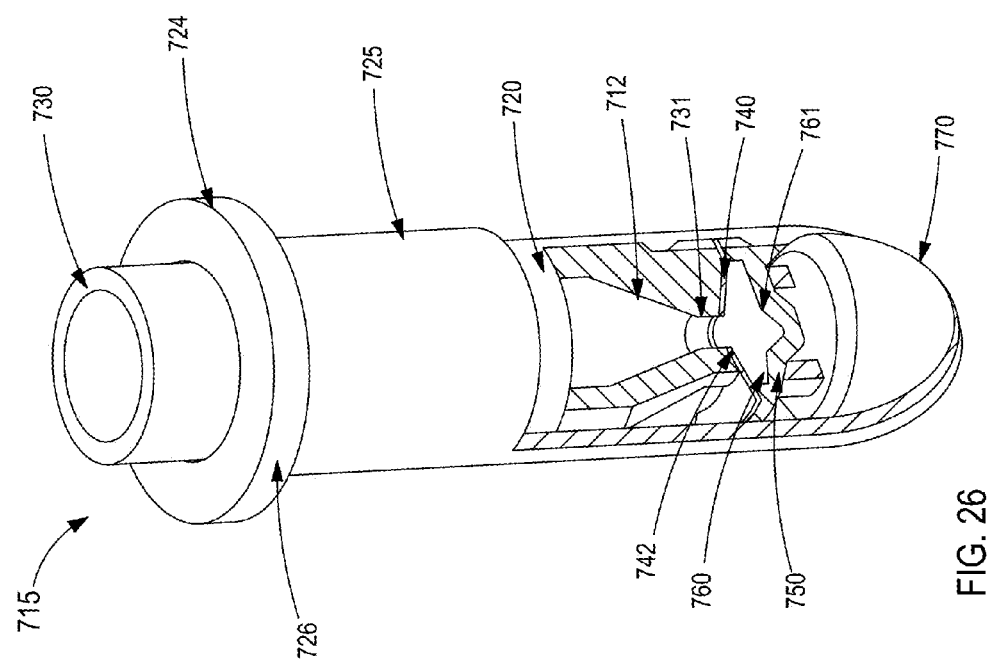
FIG. 26 is a perspective view of a tube assembly, according to an embodiment, with a portion of the tube assembly removed for illustration purposes.
Figure 28:
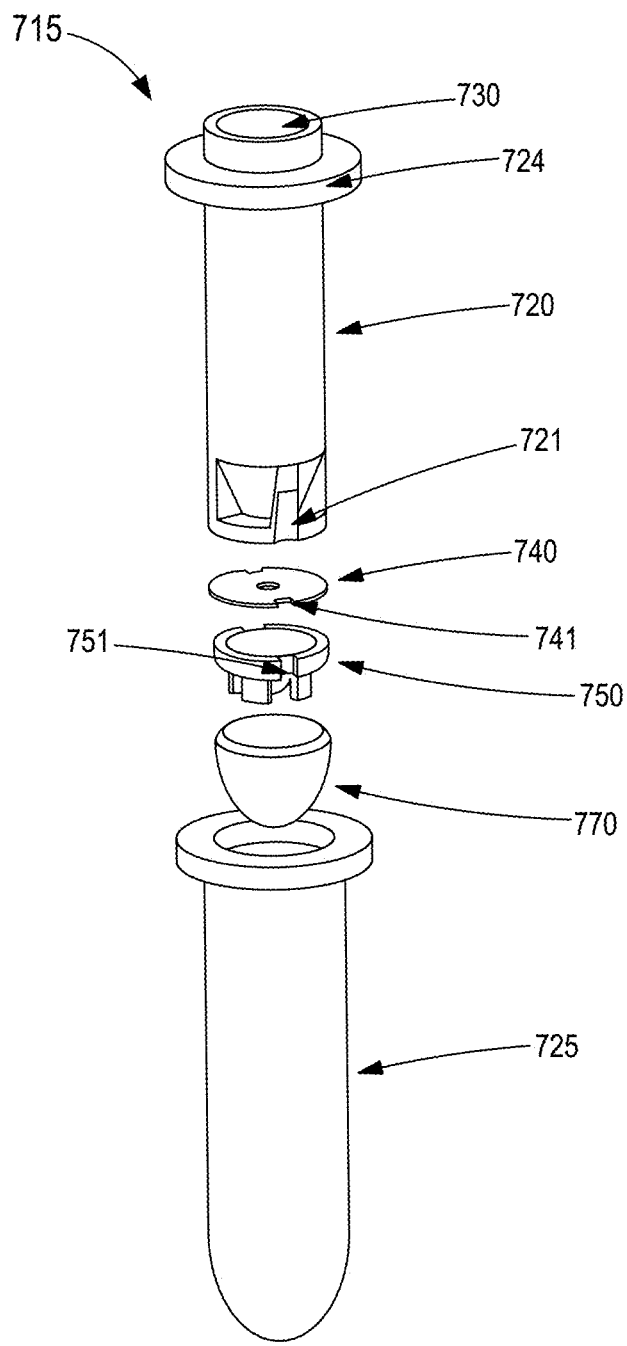
FIG. 28 is an exploded view of the tube assembly of FIG. 26.

FIGS. 26-28 illustrate a tube assembly 715, according to an embodiment. Similar to well plate assembly 600 described above, a tube assembly can be employed for certain types of assays in which it is desirable to collect and neutralize potentially hazardous effluent. As shown, for example, in FIG. 26, the tube assembly 715 includes a top tube 720 that defines a top opening 730. The top tube 720 includes a flange 724 that rests on a sleeve flange 726 and allows for limited insertion of top tube 720 within a sleeve member 725. A microporous membrane 740 is disposed between top tube 720 and a base 750. Liquid can pass up through membrane 740, through a notch 721 in the top tube 720, through a notch 741 in the membrane 740, then through a notch 751 in the base 750, and into a bottom portion of sleeve member 725. An optional absorbent material member 770 can rests within the bottom portion of sleeve member 725 and can absorb any effluent.

As shown, for example, in FIG. 26, in this embodiment, top tube 720 of tube assembly 720 includes a tapered inner bore 712 in fluid communication with top opening 730 and a base opening 731. Membrane 740 has a circular tube aperture 742 centrally disposed and aligned with the tube base opening 731. Samples can be placed into tube 720 and can flow into a reservoir 760 of the base 750, and cells or particles can collect in recessed portions 761 of the reservoir 760. During centrifugation, liquid flows through membrane 740 and eventually into the bottom portion of sleeve 725 where it can be absorbed by absorbent material member 770.

Figure 29:
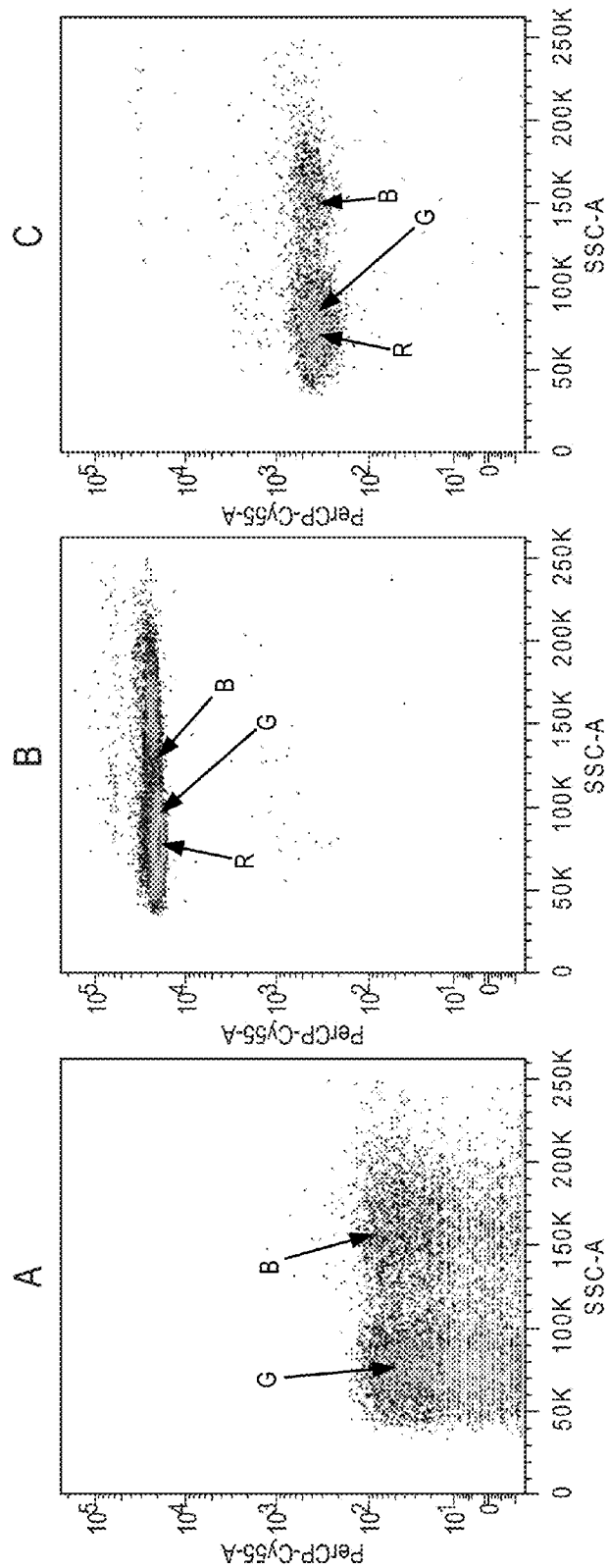
FIG. 29 illustrates multiple flow cytometry dot plots of example data generated using, for example, a well plate assembly according to an embodiment, showing proof-of-principle and efficacy.

FIGS. 29-33 illustrate data generated during, for example, use of the four-well plate assembly 400 described herein. Specifically, a prototype of well plate assembly 400 was used to process human blood samples and generate the data shown in FIGS. 29-33. After washing, the samples were run in BD TruCount™ tubes to obtain the most accurate cell number counts possible. FIG. 29 includes three bivariate dot plots summarizing the data from flow cytometric analysis of a Propidium Iodide (PI) washout experiment demonstrating the efficacy of the prototype washing cells following staining with PI. PI is a fluorescent dye that binds to DNA and efficiently stains permeabilized cells making these cells fluoresce with well-known excitation and emission frequencies. Use of PI for analytical purposes requires that cells remain in a solution of PI because washing PI stained cells has been shown to reduce the amount of PI bound to the cells (PI washout). In FIG. 29 methanol permeabilized peripheral blood mononuclear cells (PBMC) from a human whole blood sample were analyzed by a flow cytometer prior to staining with PI (Plot A), after staining with PI (Plot B), and after washing the stained cells with the prototype (Plot C). Individual cells are represented as individual dots on the plots where their position in two dimensional space is plotted by their intrinsic light scattering property on the x-axis (linear scale) and the amount of PI fluorescence is plotted on the y-axis (logarithmic scale, base 10). Where multiple cells overlap in the plot a color scale from blue through green to red allows the visualization of the density of cells in that region of the plot. Plot A shows the methanol permeabilized peripheral blood mononuclear cells (PBMC) from the blood sample prior to staining with PI; note the dots (cells) are plotted relatively low on the y-axis because there is no signal from PI and the detector is registering only background noise in the PI detection channel (PerCP-Cy55 channel). Plot B shows the permeabilized PBMC after staining with PI, but before washing with the prototype; note the cells are plotted relatively high on the y-axis because there is so much PI bound to the cells that it is near the maximum value that can be registered on the detection channel. Plot C shows the permeabilized and PI stained PBMC after washing with the prototype; note the cells are plotted much lower on the y-axis than in Plot B corresponding to a significant reduction in the amount of PI bound to the cells. The y-axis in these plots is on a logarithmic base 10 scale so washing in the prototype results in a greater than 50 fold reduction in PI fluorescence.

Figure 30:
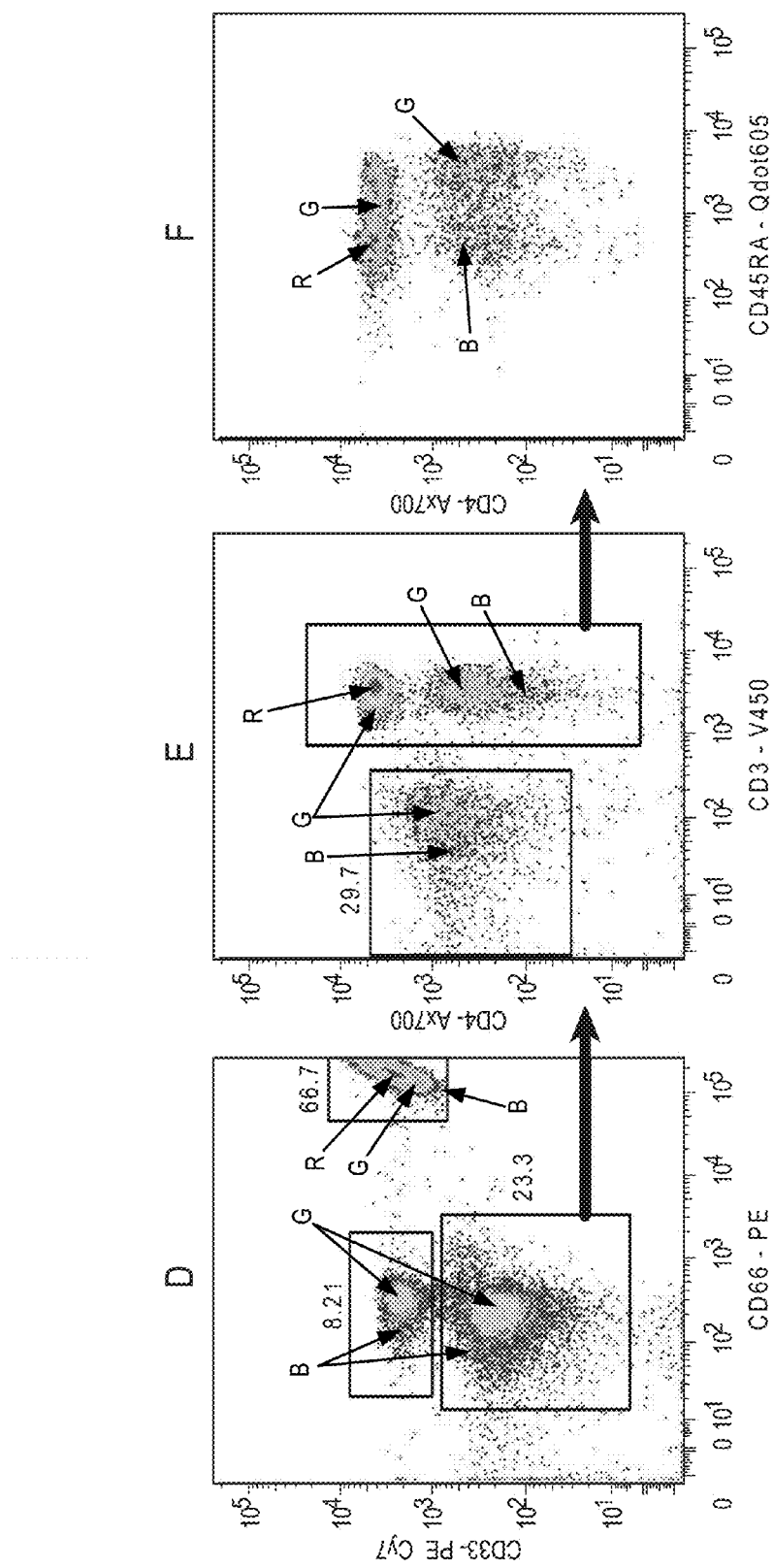
FIGS. 30 and 31 each illustrate different plots of flow cytometry data generated using, for example, a well plate assembly according to an embodiment, showing proof-of-principle and efficacy.
Figure 31:
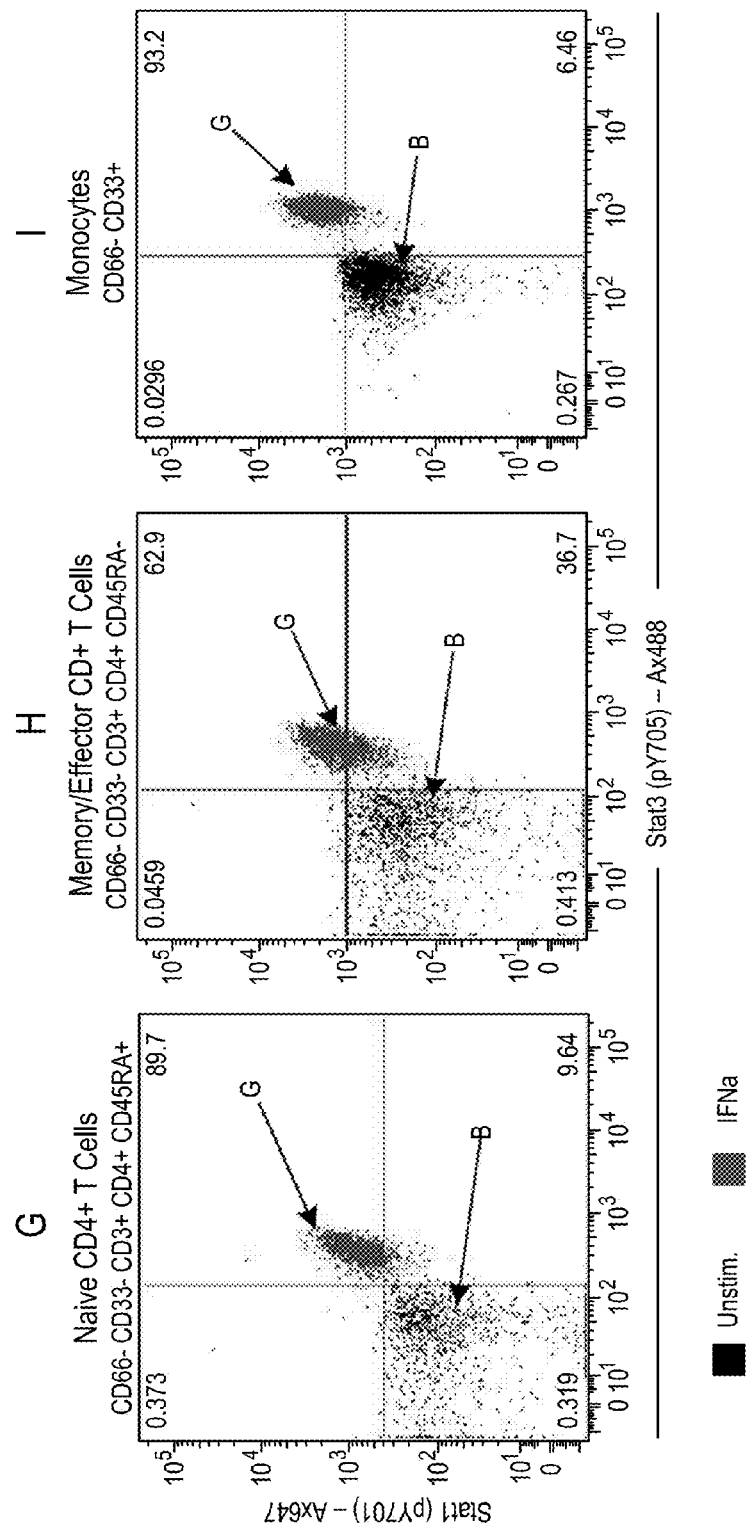

The results of a surface gating of whole blood phospho-flow experiment washed in the prototype of well plate assembly 400 is shown in FIG. 30 and the intracellular staining from that experiment is shown in FIG. 31. This experiment demonstrates the utility of this well plate assembly design for antibody staining and washing samples for complex flow cytometry experiments. A human whole blood sample was split into two aliquots, one incubated for 15 minutes with cytokine interferon alpha (IFNa) at a final concentration of 100 nanograms per milliliter while the other aliquot was incubated with a similar volume of phosphate buffered saline as a control. At the end of the 15 minute incubation both aliquots were fixed, erythrocytes lysed, and antibody staining for detection of surface epitopes was followed by methanol permeabilization and subsequent antibody staining for detection of intracellular epitopes as known in the art (see, e.g., U.S. Patent App. Publication No. 2009/0155838, the disclosure of which is incorporated herein by reference in its entirety). Plot D shows a population of cells highly positive for cell surface marker CD66 which corresponds to granulocytes and much lower levels of this marker on other cells types, as expected. It also shows a clearly CD33 positive population that is low for CD66 expression which corresponds to Monocytes. The population that is low for both CD66 and CD33 is analyzed in Plot E for expression of CD3 and CD4; two populations are found to be positive for CD3 corresponding to CD4+ and CD4− T cells, as expected. Taking all of the CD3 positive cells and analyzing them in the bivariate Plot F it is clear that both the CD4+ and CD4− populations of T cells have their own subsets of CD45RA+ and CD45RA− T cells corresponding to naïve and memory/effector T cells, respectively, as known in the art. Plots on FIG. 31 show the intracellular phospho-specific antibody staining results from this experiment for three different cell types defined by the expression of surface epitopes listed at the top of each plot (gating based on these epitopes as shown in FIG. 30); Plot G shows the phospho-specific antibody staining for Naïve CD4+ T cells, Plot H shows the phospho-specific antibody staining for Memory/Effector T cells, and Plot I shows the phospho-specific antibody staining for Monocytes. Incubating human PBMC with IFNa is known in the art to induce phosphorylation of specific amino acid residues (specific phospho-epitopes) on the signaling proteins STAT1 and STAT3. In this experiment, two fluorescently labeled antibodies that bind with high specificity to these specific phospho-epitopes were used to stain the cells. Cells from the aliquot incubated with IFNa are plotted as red dots (labeled R in FIG. 31), cells from the aliquot incubated with the saline control are plotted as black dots (labeled B in FIG. 31). As expected, in each Plot G, H, and I the red dots are to the right and above the black dots corresponding to significant detection of IFNa induced phosphorylation of STAT1 and STAT3. An unwashed fraction was diluted four times prior to being run, which helps reduce background noise.

Figure 32:
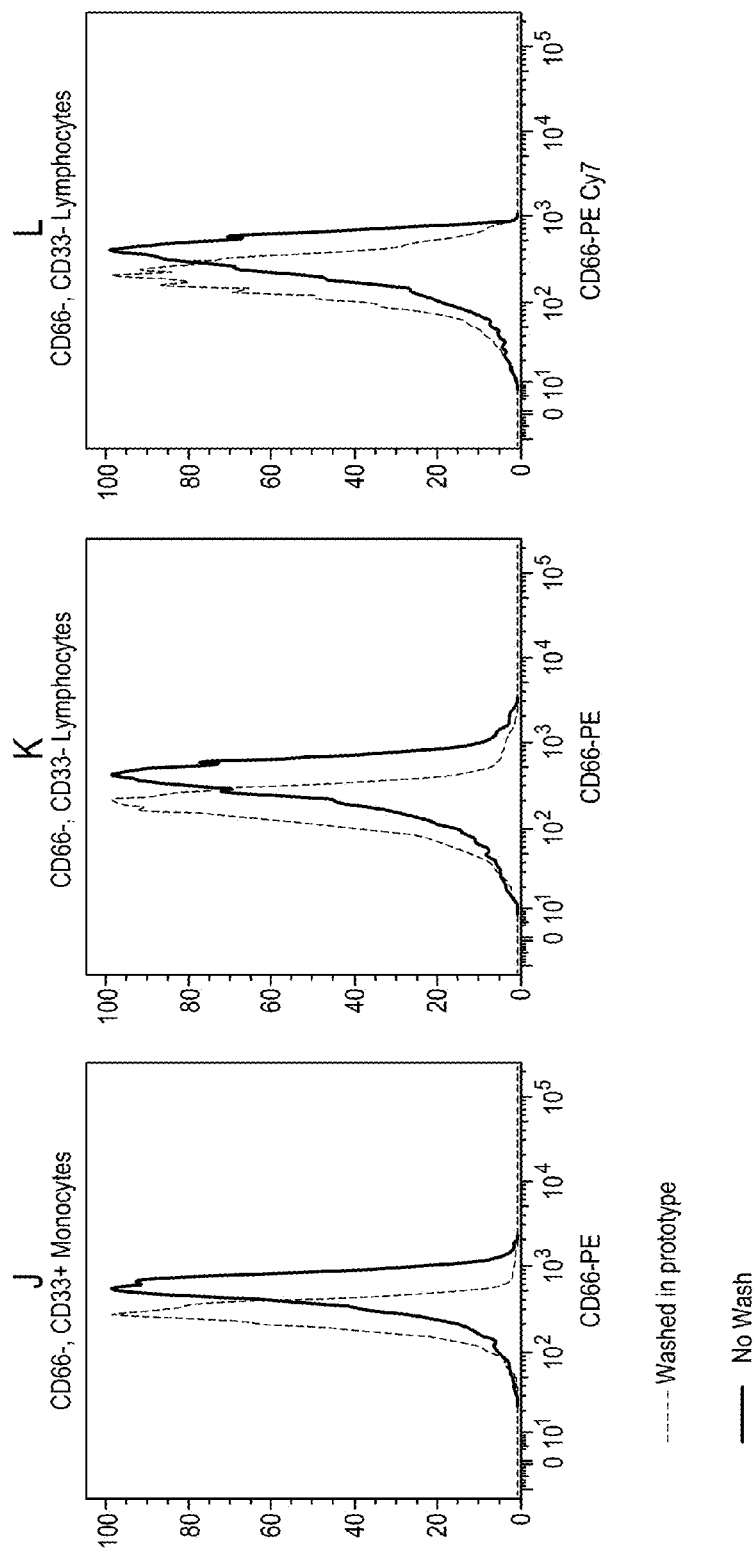
FIGS. 32 and 33 each show flow cytometry plots of example data generated using, for example, a well plate assembly according to an embodiment, showing proof-of-principle and efficacy.

FIG. 32 shows the effectiveness of the well plate assembly 400 reducing background staining of surface antibodies when the well plate assembly was used to wash stained cells. In an ideal scenario, where the background binding of the antibody was zero, the intensity of the antibody's staining on cells lacking the target surface protein would be zero. In actual use, antibodies do not bind only to their target but also other elements of the cell, referred to as non-specific staining, and as a result the background staining of every antibody is distinctly non-zero, especially when cells are fixed and permeabilized. Background staining is one of the primary challenges of flow cytometry, especially intracellular flow cytometry, because it limits signal-to-noise and thereby makes it difficult to detect low-abundance analytes in cells. Washing cells has been shown to effectively reduce the background binding of all antibodies by washing away a high fraction of antibodies sticking non-specifically to the cell while not dislodging an antibody molecule if bound to its proper target due to the high-affinity of this interaction. In each Plot J, K, and L a histogram shows the amount of background staining found on each cell type (each cell type defined by a combination of surface markers listed at the top of the plot) where the x-axis shows the level of staining with fluorescently labeled antibody that has high specificity for a surface marker not found on the cell type in that plot. The y-axis scale is from zero to one hundred percent and quantifies the fraction of the sample at each value on the x-axis. The x-axis value of the peak of each histogram is approximately the median value of background staining (x-axis value) for the cell type. The red histogram (labeled R in FIG. 32) in each plot shows the background staining of the cells prior to being washed in the prototype and the blue histogram (labeled B in FIG. 32) shows the background staining of the cells after being washed in the prototype. As can be seen in each Plot J, K, and L, the peak of the blue histogram is distinctly to the left of the peak of the red histogram indicating that washing in the prototype significantly reduced background staining. Note that the x-axis is a logarithmic scale, base 10, so the difference in the peaks corresponds to approximately a 5 fold difference in background staining. Washing was effective even when large protein fluorophores such as phycoerythrin (PE) were conjugated to the antibodies. Though not shown here, washing was effective even when Quantum Dots were conjugated to the antibodies demonstrating that the membrane of the well plate assembly allowed Quantum Dot conjugates to pass through (e.g., the pore size was large enough).

Figure 33:
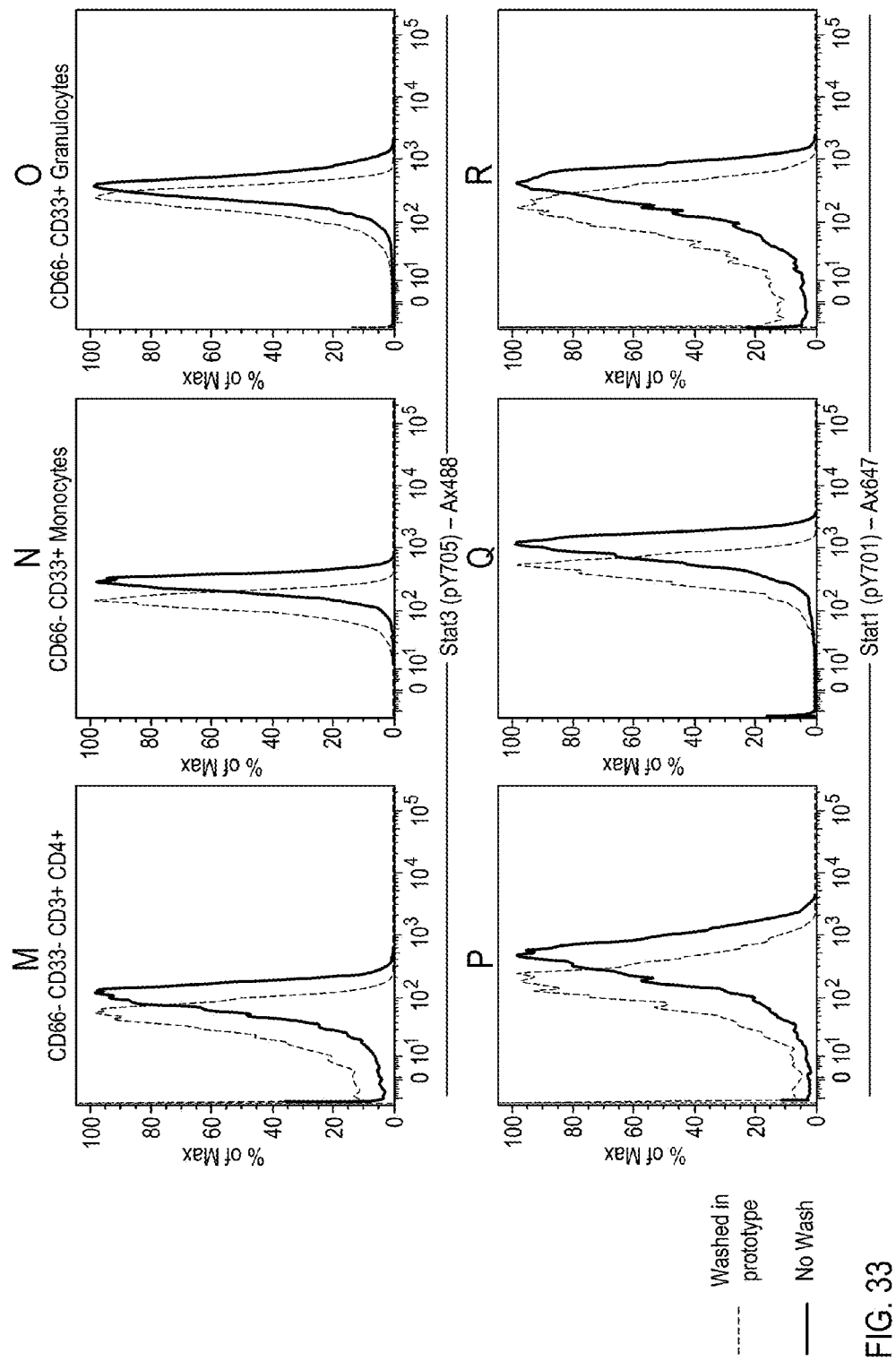

FIG. 33 shows the effectiveness of the washing process on background staining with phospho-specific antibodies. All plots are of an aliquot of human blood that was incubated with saline as a control so the cells have low levels of the phospho-epitopes targeted by the phospho-specific antibodies used here. The cell surface markers that identify the cell type are listed at the top of each column of plots. The histograms in the top row of plots quantify the staining of the cells with an antibody that binds to a specific tyrosine residue of the signaling protein STAT3 only when it is phosphorylated (tyrosine 705). The histograms in the bottom row of plots quantify the staining of the cells with an antibody that binds to a specific tyrosine residue of the signaling protein STAT1 only when it is phosphorylated (tyrosine 701). As in FIG. 32, the red histogram (labeled R in FIG. 33) in each plot shows the background staining of the cells prior to being washed in the prototype and the blue histogram (labeled B in FIG. 33) shows the background staining of the cells after being washed in the prototype. Staining permeabilized cells with these antibodies results in some non-specific background binding to the cells such that histograms of the cells prior to being washed by conventional methods is higher than after being washed by conventional methods. As can be seen in the plots of FIG. 33, the blue histograms are to the right of the red histograms in each plot demonstrating that the prototype effectively washes cells stained with phospho-specific antibodies and thereby reduces background staining with these antibodies.

In another example, a well plate assembly as described herein can be designed to optimize cell counting by flow cytometry (CD4 T cell counts for HIV patients as well as other applications). In this example, each well of the well plate assembly has within it a known number of beads whose light scattering and fluorescence make them easy to discriminate from leukocytes (similar to the approach used by Becton Dickinson's TruCount tubes). Within the well are also the desired fluorescently labeled antibodies required to stain the blood samples such that cells of interest are properly characterized by expression of cell surface markers that are specifically bound by the antibodies (i.e., CD3, CD4, CD19, CD14, CD66, etc.). For maximal antibody stability, the antibodies may be in a solution containing agents that improve their stability such as bovine serum albumin or the antibodies may be lyophilized or otherwise dried down (the beads can also be dried down). An appropriate volume of the whole human blood to be analyzed is added to the wells of the well plate assembly and incubated at 4 degrees Celsius for 20 minutes until antibody staining is complete. An appropriate volume would be, for example, 100 microliters, but much smaller and much larger volumes are also anticipated including, but not limited to volumes between 5 microliters up to 1 milliliter. If desired, erythrocyte lysis can be carried out after this 20 minute antibody staining reaction by hypotonic shock through the addition of distilled water or ammonium chloride erythrocyte lysis buffer, or other techniques known in the field for erythrocyte lysis. A wash buffer composed of phosphate buffered saline (with or without the addition of bovine serum albumin and or other reagents) is added in a volume sufficient to stop the lysis reaction.

The well plate assembly is then centrifuged to generate a centripetal acceleration that permits proper operation (e.g., 100 rcf to 200 rcf may be sufficient, but higher or lower accelerations may be desired for proper function) such that most of the liquid fraction of the sample (the effluent) flows through membrane 1 (e.g., membrane 648 in well plate assembly 600—the hydrophilic membrane), then drains through the drain holes, through the micro holes in membrane 2 (e.g., membrane 648 in well plate assembly 600—the hydrophobic membrane), which are aligned with the drain holes, and into the absorbent material in the collection tray where any biohazardous agents in the effluent are neutralized by chemicals in the absorbent material (such as, for example, concentrated sodium hypochlorite). The stained, lysed, and washed samples can then be analyzed by flow cytometry or by other cell based analysis methods. An apparatus as described herein can be configured such that it can be used directly on flow cytometers or other analysis instruments capable of drawing samples directly from 96 well plates. Although some of these instruments are not currently configured to draw samples from such a deep well plate, optional accessories for such devices can allow the use of deep welled plates.

Figure 34:
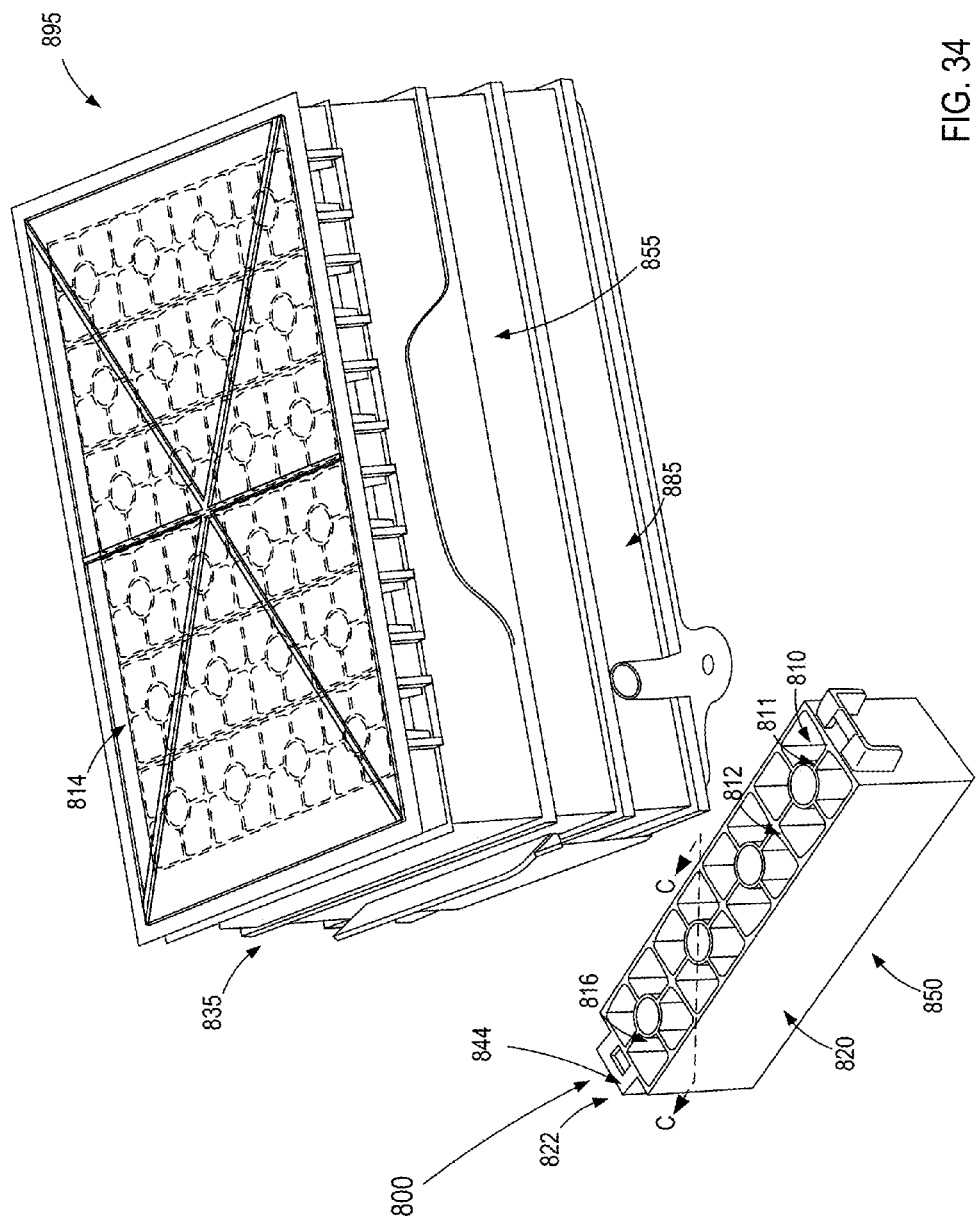
FIG. 34 is a perspective view of a well plate assembly and a tray assembly according to another embodiment.

Referring now to FIGS. 34-41, a well plate assembly 800 (also referred to herein as "plate assembly") and a tray assembly 895 are illustrated according to an embodiment. The tray assembly 895 can be any suitable shape, size, or configuration. For example, as shown in FIGS. 34-37, the tray assembly 895 can include a coupling tray 835, a collection tray 855, and a drain tray 885 arranged in a substantially stacked configuration. The coupling tray 835 can be configured to couple the well plate assembly 800 to the tray assembly 895. More specifically, the coupling tray 835 includes containment walls 838 that define an inner volume 829 that can receive a portion of the well plate assembly 800. Furthermore, opposite sides of, for example, two of the containment walls 838 can include and/or define a coupling portion 832 that can selectively engage a portion of the well plate assembly 800 such that the well plate assembly 800 traverses the inner volume 829. In this manner, a portion of the well plate assembly 800 can be disposed in the inner volume 829 (e.g., the portion of the well plate assembly 800 is substantially circumscribed by the containment walls 838). The arrangement of the coupling tray 835 can be such that the coupling portion 832 can engage a coupling portion of any number of well plate assemblies 800 having any suitable configuration. For example, as shown in FIGS. 34-37, the coupling portion 832 can be configured to matingly engage coupling portions or flanges 822 of the well plate assembly 800. Although a single well plate assembly 800 is shown, more than one well plate assembly 800 can be coupled to coupling tray 835. For example, as shown in FIG. 34, in this embodiment, the well plate assembly 800 includes 16 wells, and six well plate assemblies 800 can be coupled to the coupling tray 835. In other embodiments, the coupling portion 832 can be configured to engage a well plate assembly including, for example, 96 wells or more. The tray assembly 895 can also include and/or can be coupled to a lid 814 that is configured to substantially cover and/or enclose the inner volume 829 of the coupling tray 835 and/or the well plate assembly 800 coupled thereto.

Figure 35:
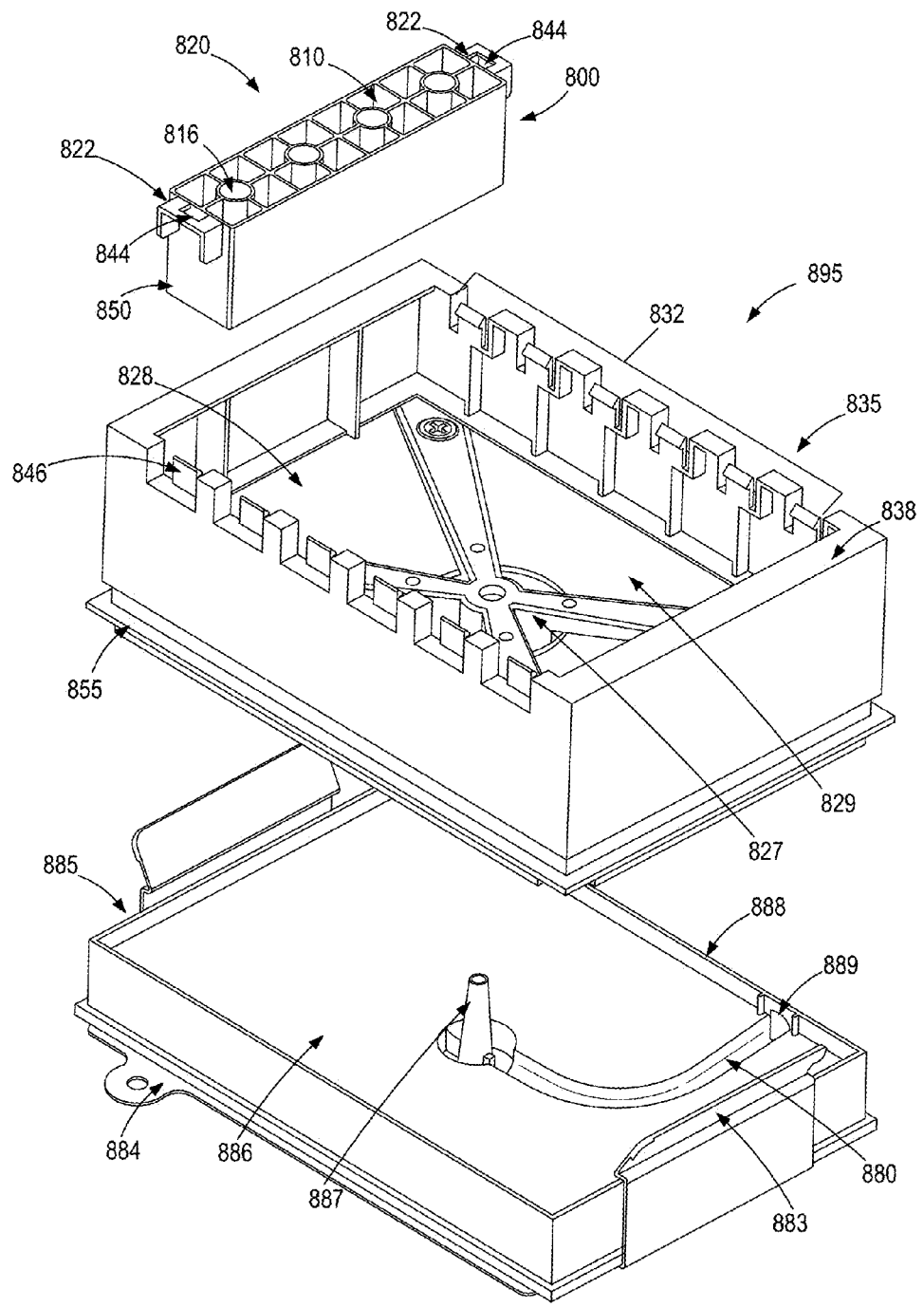
FIG. 35 is a partially exploded view of the tray assembly and well plate assembly of FIG. 34.
Figure 36:
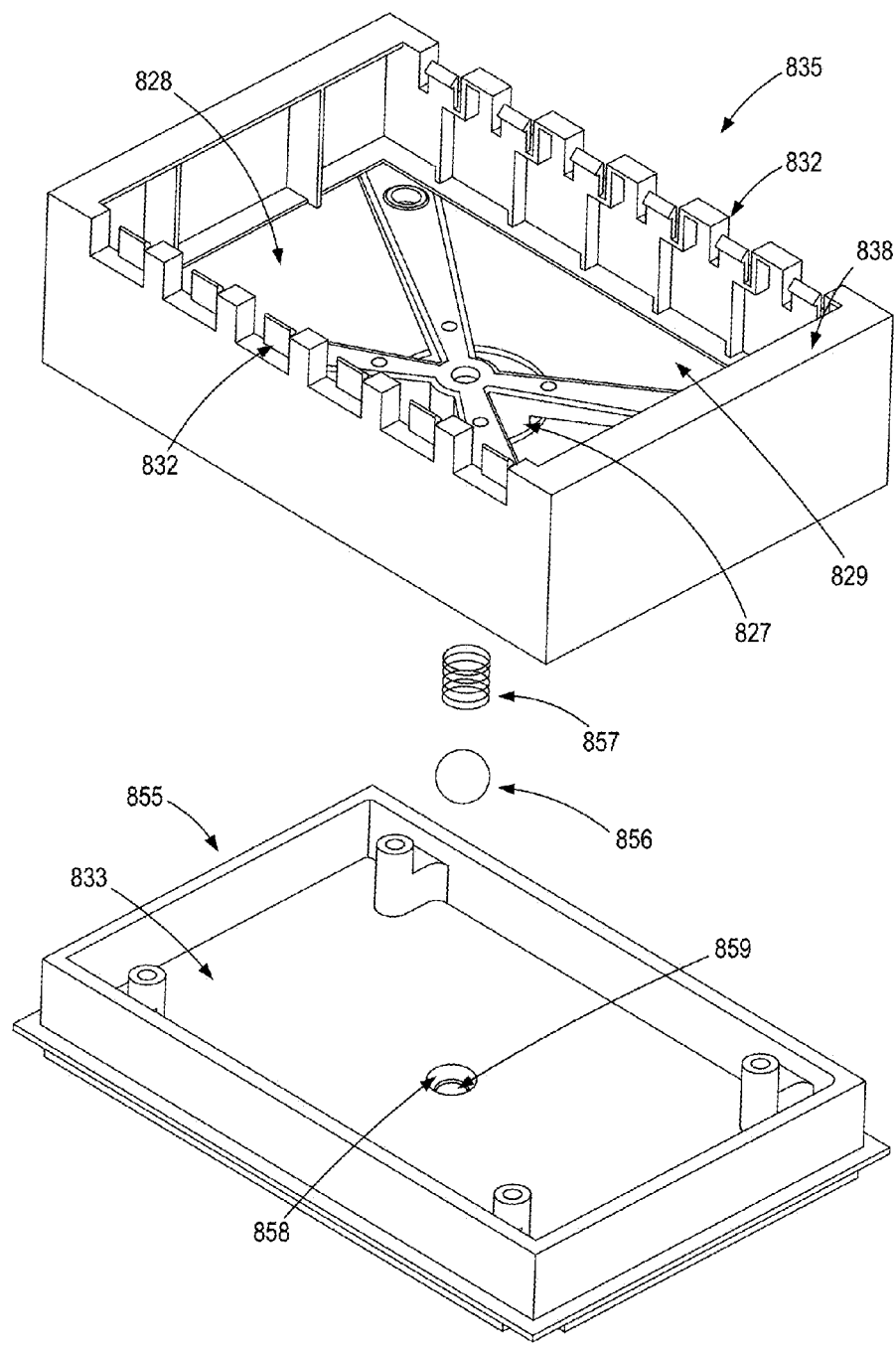
FIGS. 36 and 37 are exploded views of a first portion and a second portion, respectively, of the tray assembly of FIG. 34.

As shown in FIG. 35, the coupling tray 835 includes a base surface 828 that defines a drain portion 827. The base surface 828 can be any suitable configuration. For example, in some embodiments, the base surface 828 can be separated into, for example, distinct portions that can have a slope between the containment walls 838 and the drain portion 827. Said another way, in some embodiments, the base surface 828 can be separated into sections that each form an obtuse angle (e.g., greater than 90°) with a corresponding inner surface of the containment walls 838. Said yet another way, the base surface 828 can be divided into portions that are each angled away from the containment walls 838 towards the drain portion 827 such that the drain portion 827 is disposed, for example, below a bottom surface of the containment walls 838. In this manner, a fluid can flow within the inner volume 829 and into contact with a portion of the base surface 828, and with the base surface 828 being divided into substantially sloped sections, the fluid can flow along the slope of the portion of the base surface 828 towards the drain portion 827. As shown in FIGS. 35 and 36, the drain portion 827 can be substantially open (e.g., the drain portion 827 can include and/or can define one or more openings). Thus, a fluid can flow along a portion of the base surface 828 towards the drain portion 827, and can flow substantially out of the inner volume 829 of the coupling tray 835 via the drain portion 827.

As shown in FIGS. 35 and 36, the coupling tray 835 of the tray assembly 895 can be coupled to and/or otherwise disposed adjacent to the collection tray 855. The collection tray 855 can be any suitable configuration. For example, as shown in FIG. 36, the collection tray 855 can define an inner volume 833 (e.g., a collection chamber). As such, when the collection tray 855 is coupled to the coupling tray 835 (as shown in FIG. 35), a fluid that flows through, for example, the drain portion 827 of the coupling tray 835 can be collected, stored, retained, and/or the like in the inner volume 833 of the collection tray 855. The collection tray 855 can include a valve ball 856, and a bias member 857.

Furthermore, as shown, the collection tray 855 can include a valve seat 858 and define an opening 859. As such, when the collection tray 855 is coupled to and/or otherwise disposed adjacent to the coupling tray 835, a first end portion of the bias member 857 can be placed in contact with a surface of the coupling tray 835 and a second end portion (e.g., an opposite end portion) can be in contact with the ball valve 856. The ball valve 856, in turn, can be in contact with the valve seat 858 included in the collection tray 855. Thus, the bias member 857 (e.g., a spring or the like) can be configured to exert a biasing force that substantially maintains the ball valve 856 in contact with the valve seat 858. In some instances, this arrangement can fluidically isolate the opening 859 from the inner volume 833 (e.g., the collection chamber) in the absence of an externally applied force (e.g., a force exerted to move the ball valve 856 relative to the valve seat 858, as described in further detail herein.

Figure 37:
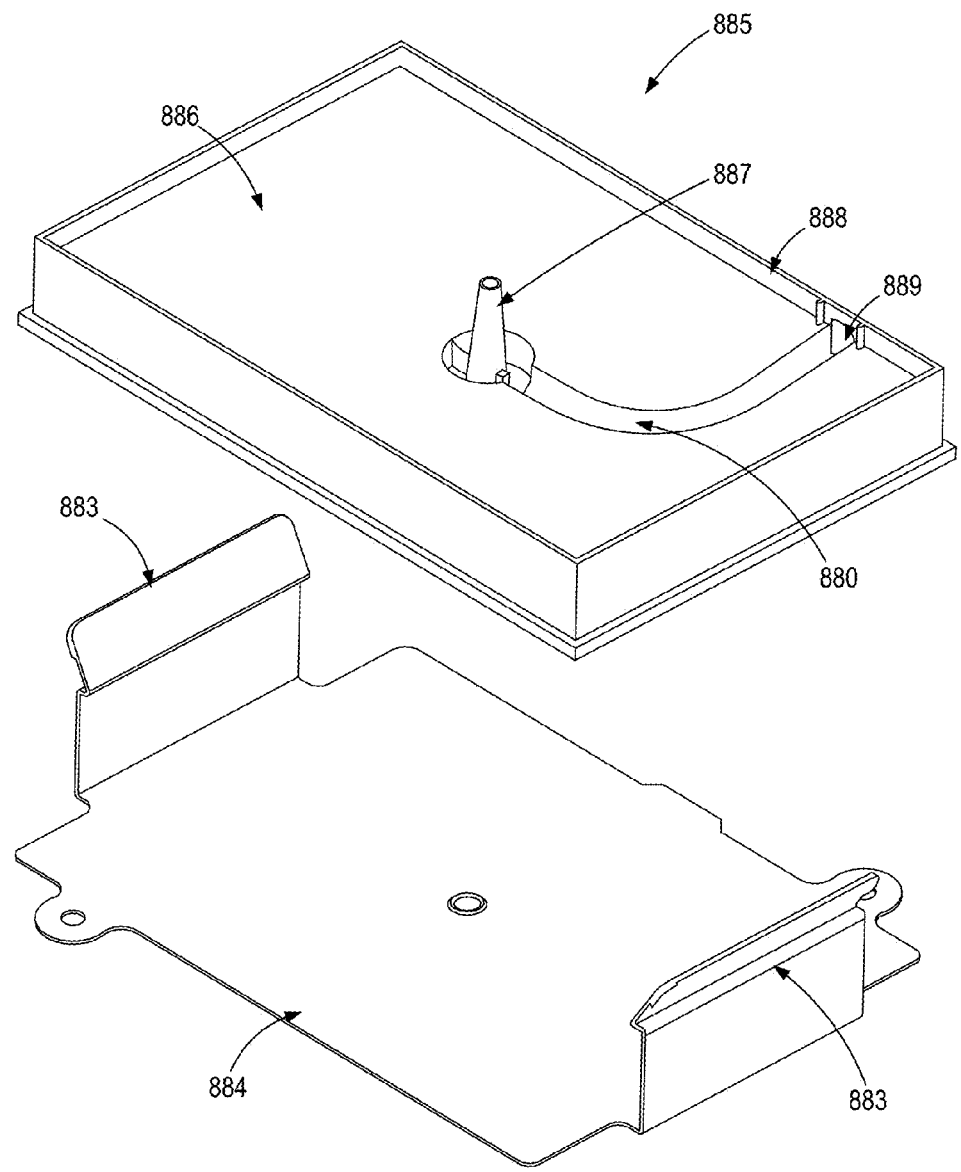

As shown in FIGS. 34, 35, and 37, the collection tray 855 of the tray assembly 895 can be coupled to and/or otherwise disposed adjacent to the drain tray 885. Said another way, the tray assembly 895 can be arranged such that the collection tray 855 is disposed between the coupling tray 835 and the drain tray 885. More specifically, as shown in FIGS. 34 and 37, the drain tray 885 can include and/or can be coupled to a retaining clip 884. The retaining clip 884 can be any suitable configuration. For example, as shown in FIG. 37, the retaining clip 884 can be a substantially planar plate from which a set of clip arms 883 can extend. The clip arms 883 can be any suitable configuration. As such, when the retaining clip 884 is coupled to the drain tray 885 and the drain tray 885 is placed adjacent to the collection tray 855, the clip arms 883 can engage a portion or surface of the coupling tray 835 to couple the collection tray 855 and the drain tray 885 thereto (e.g., the clip arms 883 can include a protrusion, tab, latch, etc. that can engage, for example, a recess, tab, notch, etc. of the coupling tray 835).

The drain tray 885 can be any suitable configuration. For example, as shown in FIG. 37, the drain tray 885 can include a drain protrusion 887, a set of walls 888, and a recessed surface 886. The recessed surface 886 defines a channel 880 that is in fluid communication with an opening 889 defined by the walls 888, as described in further detail herein. In some embodiments, the channel 880 can include, for example, a flexible hose or the like. As such, the flexible hose can be connected to a laboratory vacuum trap or similar device for removing the liquid that collects in the recessed surface 886 in a manner that is considered safe and convenient in the laboratory environment. For example, in some instances, a vacuum trap and/or the like can be used to aspirate supernatant from the recessed surface 886, filter plates, and/or similar devices. Moreover, the recessed surface 886 can be substantially non-planar. For example, in a similar manner as described above with the coupling tray 835, the arrangement of the drain tray 885 can be such that the recessed surface 886 forms a slope away from the walls 888 towards the drain protrusion 887. Thus, a fluid can flow along a portion of the recessed surface 886 towards the drain protrusion 887. The drain protrusion 887 can extend from a central portion of the recessed surface 886 to selectively engage a portion of the collection tray 855. More specifically, the arrangement of the drain tray 885 and the collection tray 855 can be such that, when disposed adjacent to one another, the drain protrusion 887 extends through the opening 859 of the collection tray 855 and into contact with the ball valve 856. As such, when the collection tray 855 is disposed between the coupling tray 835 and the drain tray 885 and the drain tray 885 is coupled o the coupling tray 835, the drain protrusion 887 can exert an external force on the ball valve 856 that is sufficient to overcome a force exerted by the bias member 857 and thus, the ball valve 856 can be moved away from the valve seat 858. In this manner, the opening 859 can place the inner volume 833 (e.g., the collection chamber) in fluid communication with the drain tray 885. Furthermore, the arrangement of the channel 880 can be such that at portion of the channel substantially circumscribes an area of the drain protrusion 887. Therefore, a fluid can flow from, for example, the well plate assembly 800, through the drain portion 827 of the coupling tray 835, through the opening defined by the collection tray 855, into, for example, the flexible tubing guided by the channel 880 and through the opening 889 to be collected in a laboratory vacuum trap and/or the like, as described in further detail herein.

As shown in FIGS. 38-41, the plate assembly 800 includes a top plate 820 (also referred to herein as "top portion"), a membrane 840, and a bottom plate 850 (also referred to herein as "bottom portion"). The top plate 820 can be at least temporarily coupled to the bottom plate 850 such that the membrane 840 is disposed therebetween. The top plate 820 includes coupling portions or flanges 822 disposed on opposite sides of the plate assembly 800 that can be operable in at least temporarily coupling the plate assembly 800 to the coupling portion 832 of the coupling tray 835, as described above. For example, the coupling portions 822 can define openings 844 that can receive therethrough tabs 846 of the coupling portions 832. As shown in FIGS. 34 and 35, the plate assembly 800 can be coupled to a first section of the coupling portion 832 (e.g., not across the entire coupling portion 832) and extend across, for example a width of the coupling tray 835. As such, any suitable number of plate assemblies 800 can be coupled to the coupling portion 832 such as, for example, one plate assembly, two plate assemblies, three plate assemblies, four plate assemblies, five plate assemblies, six plate assemblies, or more. As shown in FIG. 34, six plate assemblies 800 are coupled to the tray assembly 895.

Figure 38:
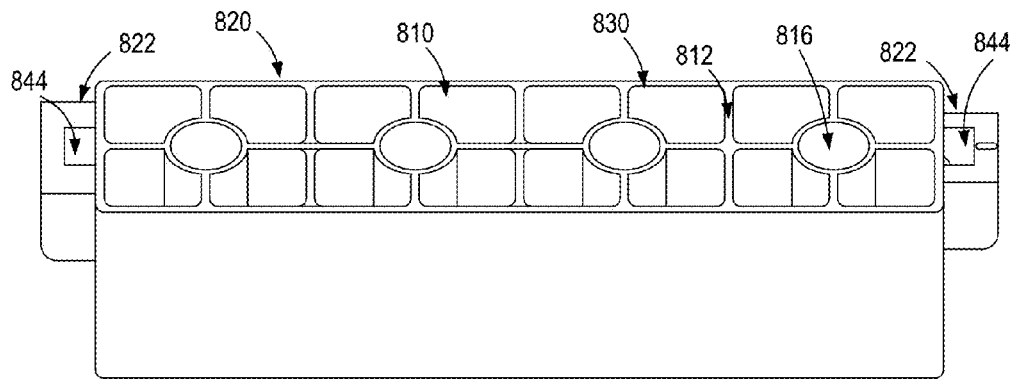
FIG. 38 is a perspective view of a top plate included in the well plate assembly of FIG. 34.

The top plate 820 can include and/or can define a set of wells 810 that can receive therein a sample (e.g., a biological sample) to be tested, for example, using a centrifugal testing system or the like. More specifically, the top plate 820 includes a set of inner walls 812 that can form at least a portion of a boundary defining the wells 810. The inner walls 812 can have any suitable arrangement. That is to say, the top plate 820 can define any suitable number of wells 810 in any suitable arrangement. For example, as shown in FIG. 38, the arrangement of the inner walls 812 can be such that the top portion 820 defines a set of 16 wells 810 in a 2×8 well arrangement. More particularly, the arrangement of the inner walls 812 can be such that the set of wells 812 are defined in 2×8 grid arrangement, with each well 810 defining and/or encompassing a volume of substantially equal size and/or shape. The arrangement of the inner walls 812 can also be such that the top plate 820 defines a set of four drain columns 816 (e.g., collection columns or the like), with each drain column 816 being in selective fluid communication with a subset of four wells 810, as described in further detail herein.

Although, the arrangement of the plate assembly 800 is specifically described as including the 16 wells 810 in a 2×8 arrangement, in other embodiments, the plate assembly 800 can include and/or can define any number of wells 810 in any suitable arrangement. For example, in some embodiments, a plate assembly can include and/or can define 96 wells in an 8×12 arrangement. In still other embodiments, a plate assembly can include and/or can define any suitable number of wells in any suitable arrangement (e.g., one well, two wells, four wells, six wells, nine wells, 24 wells, 48 wells, 128 wells, 144 wells, 384 wells, 768 wells, 1536 wells, and/or any number of wells therebetween. Similarly, although the plate assembly 800 is specifically described as including four drain columns 816, in other embodiments, a plate assembly can include any number of drain columns that can be configured to be in selective fluid communication with any number of wells such that each well included in the plate assembly is in fluid communication with at least one drain column.

Figure 41:
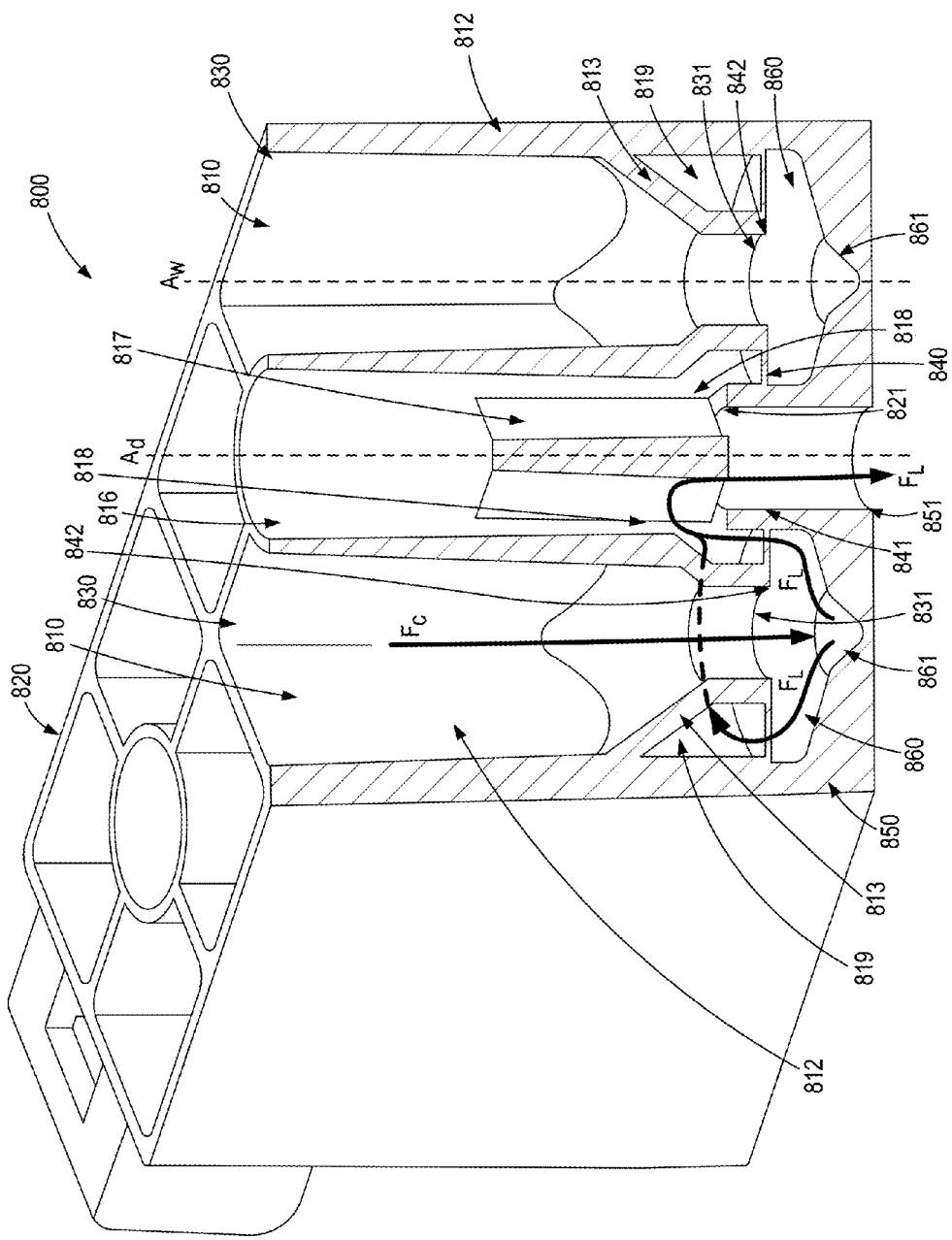
FIG. 41 is a cross-sectional view of the well plate assembly of FIG. 34, taken along the line C-C in FIG. 34.

Expanding further, as shown in FIGS. 38 and 41, the arrangement of the inner walls 812 of the top plate 820 is such that the wells 810 are grouped, subdivided, and/or otherwise collected into subsets disposed around or about one of the drain columns 816. For example, the set of wells 810 can be grouped into subsets of four wells, with each well in a set being in fluid communication with one drain column 816 associated with that set of four wells. More specifically, the arrangement of the top portion 820 can be such that a portion of the inner walls 812 defining each well 810 included in a subset (e.g., a grouping of four wells) also forms and/or defines the drain column 816 and vice versa. In other words, the arrangement of the top plate 820 can be such that a portion of the inner walls 812 that defines a drain column 816 also defines a portion of each of the four wells 810 in the subset disposed about the drain column 816. For example, as shown in FIGS. 38 and 41, in some embodiments, a portion of the inner walls 812 can form and/or can be arranged as a substantially cylindrical annulus to define the drain volumes 816 therebetween (i.e., internal of the substantially cylindrical annulus), and a portion of the wells 810 thereabout (i.e., external of the substantially cylindrical annulus). Furthermore, a portion the inner walls 812 that forms the substantially cylindrical annulus can define an opening, port, channel, and/or the like that can selectively place the wells 810 included in the subset of wells 810 disposed about that drain column 816 in fluid communication with at least one drain column 816, as described in further detail herein. Although the inner walls 812 are specifically described above as defining the wells 810 and the drain columns 816, the arrangement of the top plate 820 can also be considered as including any number of wells 810 and any number of drain columns 816, each of which has an outer structure or the like that can form, for example, a portion of the inner walls 812 of the top plate 820.

The wells 810 and/or the inner walls 812 defining the wells 810 can include and/or can define a top opening 830 and a bottom opening 831, as shown in FIG. 41. As such, a sample can be delivered to the well 810 via the top opening 830 and the well 810 can be configured such that the sample can pass therethrough via the bottom opening 831. Moreover, the inner walls 812 include a tapered portion 813 such that a size (e.g., diameter) of the bottom opening 831 is smaller than a size of the top opening 830. Expanding further, the arrangement of the wells 810 and/or the inner walls 812 can be such that a channel 819 is defined between an outer surface of the tapered portion 813 and, for example, an inner surface of a portion of the inner walls 812 defining that well 810. The channel 819 can be configured to substantially circumscribe the tapered portion 813 of the inner walls 812 (and thus, a portion of the corresponding well 810). Moreover, as shown in FIG. 41, the inner walls 812 can define an opening 818 that can place the channel in fluid communication with the drain column 816. In addition, the plate assembly 800 can include a divider 817 or the like that is disposed within the drain column 816. The divider 817 can, for example, divide and/or separate the drain column 816 into substantially fluidically isolated portions. As such, the inner walls 812 and/or the drain column 816 can define a set of the openings 818 with each opening being associated with a divided segment or volume of the drain column 816. Thus, a flow of a fluid, liquid, and/or the like can flow through the channel 819 associated with, for example, a first well 810 and into a first opening 818 to be disposed in a first portion of the drain column 816, and a flow of a fluid, liquid, and/or the like can flow through a channel 819 associated with, for example, a second well 810 and into a second opening 818 to be disposed in a second portion of the drain column 816.

Although not shown in FIGS. 38-41, in some embodiments, a bottom surface and/or portion of the top plate 820 can be arranged such that the channel 819 extends therethrough (e.g., the bottom surface of the top plate 820 defines an opening corresponding to the channel 819 associated with each well 810). As described in further detail herein, the arrangement of the plate assembly 800 can be such that when the membrane 840 is disposed adjacent to and in alignment with the top plate 820, the membrane 840 substantially covers the channel 819 (e.g., the channel 819 is physically separated from a volume on an opposite side of the membrane 840).

The membrane 840 of the plate assembly 800 is configured to be disposed between the top plate 820 and the bottom plate 850 of the plate assembly 800 (see e.g., FIG. 41) when the top plate 820 and the bottom plate 850 are coupled together. The membrane 840 can be formed from and/or can be arranged as a substantially planar microporous sheet. In some embodiments, the membrane 840 can be formed with a material such that the membrane 840 is a barrier to the passage of cells, but allows liquid to pass through with little impedance. Such membranes can include, but are not restricted to, hydrophilic membranes including those used in plasmapheresis such as polyethersulfone membranes with a pore size between, for example, 0.2 micron and 2 microns and that are considered "low-binding" in that proteins and cells do not readily stick to them. In some embodiments, the pore size is smaller than the diameter of the cells that are to be retained in the sample well (e.g., most leukocytes are approximately 8 microns in diameter), but large enough to allow reagents to pass through the membrane 840. For example, such reagents can include, but are not limited to, human serum constituents, culture media, bovine serum albumen, antibodies, cytokines, small molecule drugs, quantum dots, oligonucleotides, fluorophores, fixatives, alcohols, and isotopes appropriate for mass cytometry chelated and attached to polymers. Additionally, the membrane 840 can be formed from and/or can include a material that is chemically compatible with the reagents and wash liquids to be used in the assay process. As such, the membrane 840 can be formed from any suitable material and/or can have any suitable arrangement such as those described above with reference to the membrane 140 in FIGS. 1-14.

Figure 39:
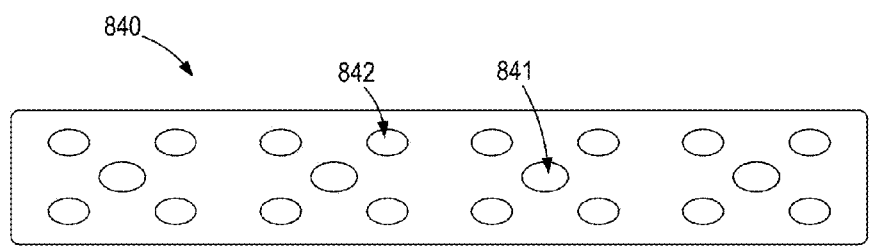
FIG. 39 is a perspective view of a membrane included in the well plate assembly of FIG. 34.

As shown in FIG. 39, the membrane 840 defines a set of drain openings 841 and a set of well openings 842. The arrangement of the plate assembly 800 can be such that when the membrane 840 is disposed between the top plate 820 and the bottom plate 850 (e.g., when the top plate 820 is coupled to the bottom plate 850), the drain openings 841 are substantially aligned with and/or are coaxial with a corresponding drain column 816 and the well openings 842 are substantially aligned with and/or are coaxial with a corresponding well 810. Thus, the arrangement of the drain openings 841 and the well openings 842 can allow a sample and/or a portion thereof to pass through the membrane 840, as described in further detail herein. Although shown in FIG. 39 as being a substantially continuous membrane 840 having a size and/or shape that is associated with an overall size and/or shape of the top portion 820, in other embodiments, the membrane 840 can include any number of independent portions with each portion being, for example, associated with and/or substantially aligned with a different well 810, as described above with reference to the membrane 140.

Figure 40:
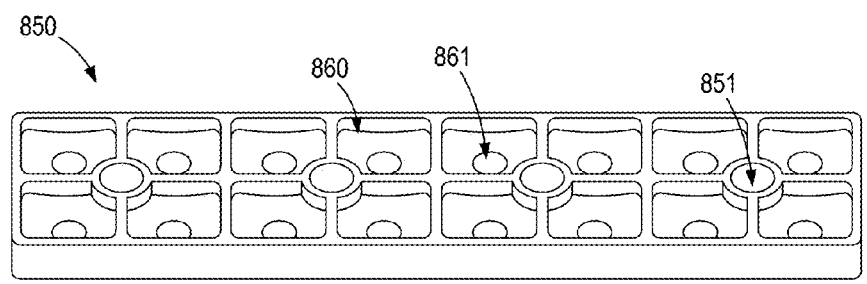
FIG. 40 is a perspective view of a bottom plate included in the well plate of FIG. 34.

The bottom plate 850 of the plate assembly 800 includes an inner surface that defines and/or forms multiple reservoirs 860 each having a recessed portion 861, as shown in FIG. 40. In addition, the bottom plate 850 defines a set of drain openings 851. As described above, the bottom plate 850 is configured to be coupled to the top plate 820. In some embodiments, the bottom plate 850 can be removably coupled to the top plate 820 (e.g., via a friction fit, a press fit, a snap fit, a mechanical fastener, a latch, a threaded coupling, and/or the like or combination thereof). In other embodiment, the bottom plate 850 can be fixedly coupled to the top plate 820 (e.g., via an adhesive such as, an epoxy, a urethane, a polyurethane, etc.; via a mechanical coupling such as, a friction fit, a press fit, ultrasonic welding, friction welding; via any other suitable manufacturing process such as, insert molding, over-molding, co-molding, thermal adhesion, etc.; and/or the like or a combination thereof).

As shown in FIG. 41, the bottom plate 850 can be coupled to the top plate 820 such that the fluid reservoirs 860 are substantially aligned with and/or coaxial with a corresponding well 810 of the top plate 820 (i.e., each fluid reservoir 860 is aligned with a different well 810), while the drain openings 851 are substantially aligned with and/or coaxial with a corresponding drain column 816 (i.e., each drain opening 851 is aligned with a different drain column 816). With the membrane 840 disposed between the top plate 820 and the bottom plate 850 and with the membrane 840 substantially aligned with the top plate 820 (as described above), the drain openings 851 of the bottom plate 850 can also be aligned with and/or coaxial with the drain openings 841 defined by the membrane 840 and the reservoirs 860 of the bottom plate 850 can also be substantially aligned with and/or coaxial with the well openings 842 defined by the membrane 840. Said another way, the arrangement of the plate assembly 800 (e.g., when the membrane 840 is disposed between the top plate 820 and the bottom plate 850 and the top plate 820 and the bottom plate 850 are coupled together, as shown in FIG. 41) can be such that each well 810 (and more specifically, the bottom opening 831 of each well 810) shares an axial centerline $A_W$ with a corresponding well opening 842 of the membrane 840 and a corresponding reservoir 860 of the bottom portion 850. Similarly, each drain column 816 (and more particularly, a drain opening 821 associated with each drain column 816) shares an axial centerline $A_d$ with a corresponding drain opening 841 of the membrane 840 and a corresponding drain opening 851 of the bottom plate 850. In addition, the plate assembly 800 can be arranged such that the membrane 840 physically separates the reservoir 860 from the channel 819 circumscribing the tapered portion 813 of the inner walls 812 defining the corresponding or aligned well 810. Thus, with the membrane 840 being selectively permeable, the membrane 840 can allow, for example, a fluid disposed in the reservoir 860 to pass through the membrane 840 to be disposed in the channel 819 and in turn, with the channel 819 in fluid communication with the drain column 816 (via the opening 818 described above), the fluid can pass through the channel 819 to be disposed in the drain column 816.

In use, a sample can be delivered through the top opening 830 of any suitable number of wells 810 defined by the plate assembly 800. Under the force of gravity, at least a portion of the sample, can flow through the well 810 and can exit the wells 810 via the bottom openings 831. With the membrane 840 and the bottom plate 850 aligned with the top plate 820, as described above, a portion of the sample can similarly flow through the corresponding well openings 842 of the membrane 842 to be disposed in the corresponding reservoirs 860. With the samples disposed in the plate assembly 800, the plate assembly 800 can be coupled to the tray assembly 895 (e.g., via the coupling portion 832 of the coupling tray 835 and the flange 822 of the top portion 820 of the plate assembly 800) and the lid 814 can be disposed about the coupling tray 835. The tray assembly 895 can then be disposed in, for example, a centrifuge device. Although the sample is described above as being transferred to the wells 810 prior to the plate assembly being coupled to the tray assembly 895, in other instances, the plate assembly 800 can be coupled to the tray assembly 895 and subsequently, the sample can be transferred to the wells 810. In such instances, the sample can be transferred to the wells 810 prior to the tray assembly 895 being disposed in the centrifuge device or after being disposed in the centrifuge device.

While being centrifuged, as shown by the flow directional arrow $F_C$ in FIG. 41, the remaining portion of the sample in well 810 is drawn to a bottom portion of the well 810 and through the openings 831 and 842 defined by the top plate 820 and the membrane 840, respectively, and into the reservoir 860 of the bottom plate 850. As shown by flow directional arrow $F_L$ in FIG. 41, the wash liquid separates from the cells and is urged to flow through a portion of the membrane 840 and into the channel 819 defined by the inner walls 812. More specifically, as the tray assembly 895 is rotated, the sample disposed in the reservoir 860 is exposed to centripetal force and/or acceleration as well as centrifugal force and/or acceleration. As such, the tray assembly 895 can be rotated with sufficient rotational velocity to separate the sample, for example, by density. In this manner, the centrifugal force and/or acceleration exerted on portions of the sample having a lower density (e.g., less dense portions such as, for example, liquid portions including wash liquids, fluids, or the like) can be sufficient to overcome, for example, the centripetal forces similarly exerted on the portions of the sample, as well as, for example, a friction force between the portions of the sample and the inner surface of the bottom plate 850 defining the reservoir 860. Thus, the centrifugal force exerted on the portions of the sample can urge such portions (e.g., the portions having a lower density) to flow along the surface of the reservoir 860 (radially and/or in an expanding spiral away from, for example, the axial centerline $A_W$) towards the membrane 840. Moreover, the centrifugal force exerted on, for example, such fluids (e.g., the less dense portions of the sample) can be sufficient to urge the fluids to flow through the membrane 840 and into the channel 819. The portion of the sample (e.g., the wash liquid, effluent, etc.) can then pass through the opening 818 and into the drain column 816. The fluids can then flow through the drain hole 821 defined by the top plate 820, through the drain hole 841 defined by the membrane 840, and through the drain hole 851 of the bottom plate 850, thereby flowing out of the plate assembly 800. Although not shown in FIGS. 34-41, in some embodiments, the inner volume 833 of the collection tray 855 and/or any other suitable portion of the tray assembly 895 can include an absorbent and/or trapping material that is configured to absorb and/or neutralize, for example, a biohazardous fluid or the like as described above for previous embodiments.

With the plate assembly 800 coupled to the tray assembly 895, the fluids can flow along the base surface 828 of the coupling tray 835, through the drain portion 827, and into the inner volume 833 (e.g., the collection chamber) defined by the collection tray 855. Furthermore, with the drain protrusion 887 engaging the ball valve 856, the fluids can flow through the opening 859 and into the channel 880 defined by the drain tray 885. The arrangement of the drain tray 885 is such that the fluids can then flow within the channel 880 and through the opening to be discarded in any suitable biologically safe manner.

As described above, centripetal force and/or acceleration directly opposes the flow of liquid out of the reservoir 860 and through membrane 840, thus forcing the cells away from the membrane 840 and into the recessed portion 861 of the reservoir 860. The level of the remaining supernatant in the well 810 can be equal to a height of the drain hole 821 of the top plate 820. The height of the entrance to drain hole 821 can act as a weir, and by adjusting this height above the membrane 840, the amount of the remaining supernatant in the well 810 after centrifugation can be adjusted. The cells or particles within the well 810 and/or the reservoir can collect or "pellet" in, for example, the recessed portion 861 of the reservoir 860. Moreover, as described above, the size of the pores in the membrane 840 can be sufficiently small as to not allow the cells to pass up through the membrane 840 with the wash liquid during centrifugation. In this manner, centrifugal processes can be serially performed on the sample with substantially less sample loss than would otherwise be possible.

Figure 42:
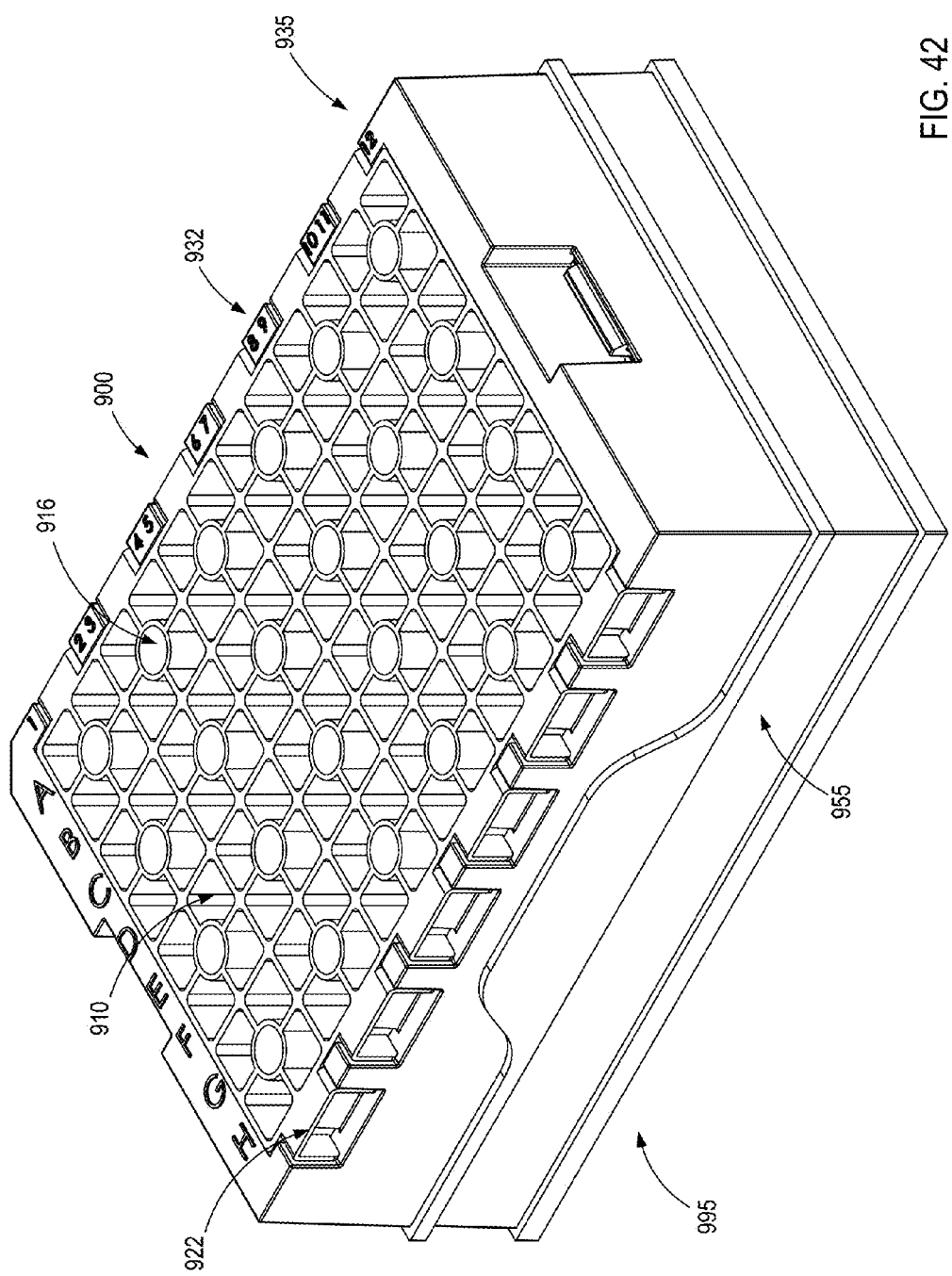
FIG. 42 is a perspective view of a well plate assembly and a tray assembly according to another embodiment.
Figure 43:
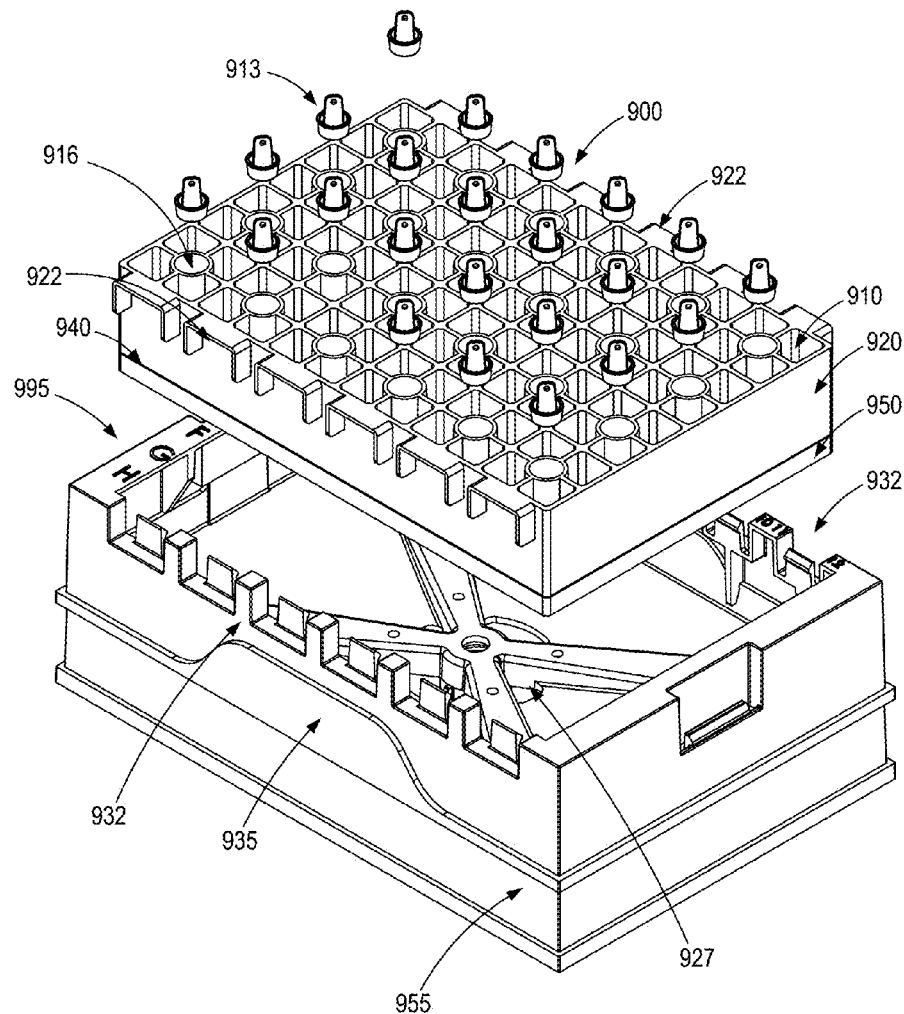
FIG. 43 is a partially exploded view of the well plate assembly and the tray assembly of FIG. 42.

Referring now to FIGS. 42-51, a well plate assembly 900 (also referred to herein as "plate assembly") and a tray assembly 995 are illustrated according to another embodiment. The tray assembly 995 can be any suitable shape, size, or configuration. As shown in FIGS. 42 and 43, the tray assembly 995 can include a coupling tray 935, a collection tray 955, and a drain tray (not shown) arranged in a similar manner as described above for tray assembly 895. As shown, for example, in FIG. 45, the tray assembly 995 can include and/or can be coupled to a lid 914 or the like that can substantially cover, for example, the plate assembly 900 when the plate assembly 900 is coupled to the tray assembly 995. The tray assembly 995 can be substantially similar to the tray assembly 895 described above with reference to FIGS. 34-37. Thus, the discussion of the tray assembly 895 can apply to the tray assembly 995 unless explicitly expressed otherwise and hence, the tray assembly 995 is not described in further detail herein.

As shown in FIGS. 42-51, the plate assembly 900 includes a top plate 920 (also referred to herein as "top portion"), a membrane 940, and a bottom plate 950 (also referred to herein as "bottom portion"). The top plate 920 can be at least temporarily coupled to the bottom plate 950 such that the membrane 940 is disposed therebetween. In some embodiments, portions of the plate assembly 900 can be substantially similar to or the same as corresponding portions of the plate assembly 800 described above with reference to FIGS. 34-41. Thus, some aspects of the plate assembly 900 are not described in further detail herein and should be considered the same as the corresponding aspects of the plate assembly 800 unless explicitly expressed otherwise.

The top plate 920 can include and/or can define multiple wells 910 that can receive therein a sample (e.g., a biological sample) to be tested, for example, using a centrifugal testing system or the like. More specifically, the top plate 920 includes a set of inner walls 912 that can form at least a portion of a boundary defining the wells 910. The inner walls 912 can have any suitable arrangement. That is to say, the top plate 920 can define any suitable number of wells 910 in any suitable arrangement. For example, as shown in FIGS. 42 and 46-49, the arrangement of the inner walls 912 can be such that the top portion 920 defines a set of 96 wells 910 in a 12×8 well arrangement. The arrangement of the inner walls 912 can also be such that the top plate 920 defines a set of 24 drain columns 916 (e.g., collection columns), with each drain column 916 being in fluid communication (i.e., via the membrane 940) with a subset of wells 910 (e.g., four wells), as described above with reference to the plate assembly 800. In other words, liquid can pass through the membrane 940 and into the drain column 916. As shown, for example, in FIGS. 42 and 43, the top plate 920 includes a set of flanges 922 disposed on opposite sides of the plate assembly 900 that can be operable in at least temporarily coupling the plate assembly 900 to a coupling portion 932 of the coupling tray 935. Expanding further, although the plate assembly 800 included a single flange 822 on opposite sides of the top plate 820 that engaged a portion of the coupling portion 832, the plate assembly 900 can include, for example, six flanges 922 disposed on opposite sides of the top plate 920 that can engage substantially the entire extent of the coupling portion 932 of the coupling tray 935 to couple the plate assembly 900 to the tray assembly 995.

Figure 44:
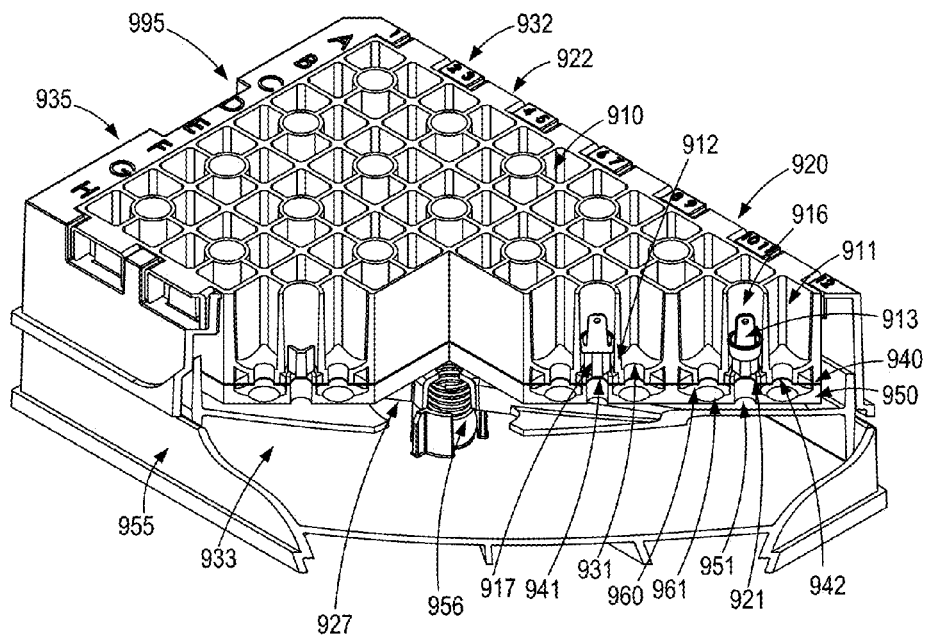
FIG. 44 is a cutaway view of a portion of the well plate assembly and a portion of the tray assembly of FIG. 42.
Figure 45:
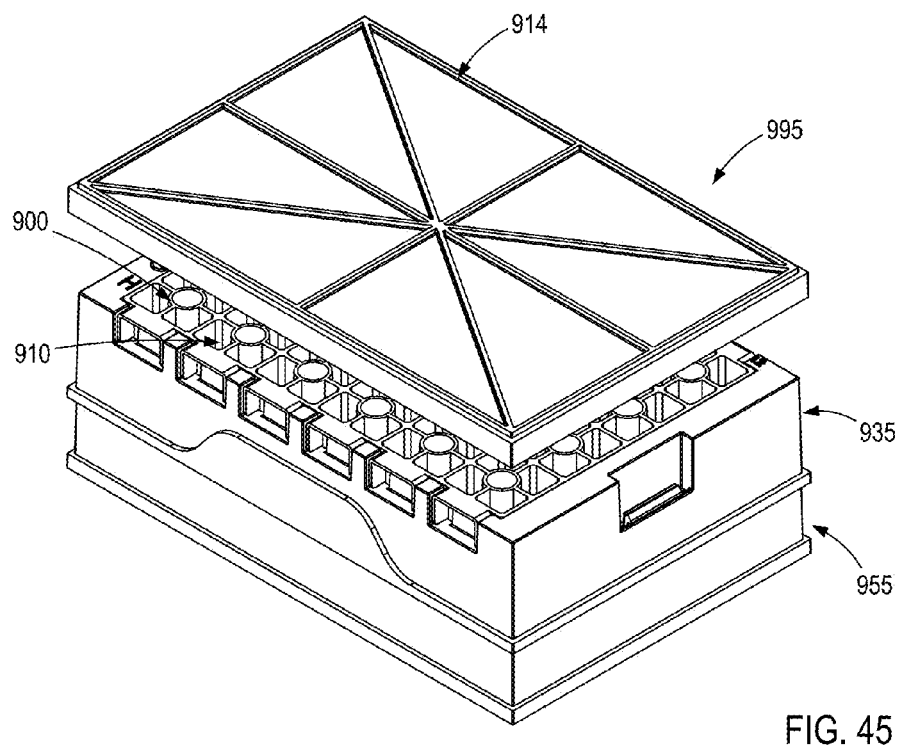
FIG. 45 is a perspective view of the well plate assembly and the tray assembly of FIG. 42 being coupled to a lid.

As shown in FIGS. 42-43, 48, and 49, the arrangement of the inner walls 912 of the top plate 920 is such that the wells 910 are grouped, subdivided, and/or otherwise collected into subsets disposed around or about one of the drain columns 916. For example, the set of wells 910 can be grouped into subsets of four wells, with each well in the subset being in fluid communication (i.e., via the membrane 940) with one drain column 916 associated with that set of four wells, as described in detail above with reference to the top plate 820 in FIGS. 38 and 41. The wells 910 and/or the inner walls 912 defining the wells 910 can include and/or can define a top opening 930 and a bottom opening 931, as shown in FIG. 44. As such, a sample can be delivered to the well 910 via the top opening 930 and the well 910 can be configured such that the sample can pass therethrough via the bottom opening 931. Moreover, the inner walls 912 include a tapered portion 913 such that a size (e.g., diameter) of the bottom opening 931 is smaller than a size of the top opening 930. Expanding further, the arrangement of the wells 910 and/or the inner walls 912 can be such that a channel 919 is defined between an outer surface of the tapered portion 913 and, for example, an inner surface of a portion of the inner walls 912 defining that well 910. The channel 919 can substantially circumscribe the tapered portion 913 of the inner walls 912 (and thus, a portion of the corresponding well 910). Moreover, as shown in FIG. 41, the inner walls 912 can define an opening 918 that can place the channel 919 in fluid communication with the drain column 916, as described in detail above with reference to the top plate 820 in FIGS. 38 and 41.

Figure 46:
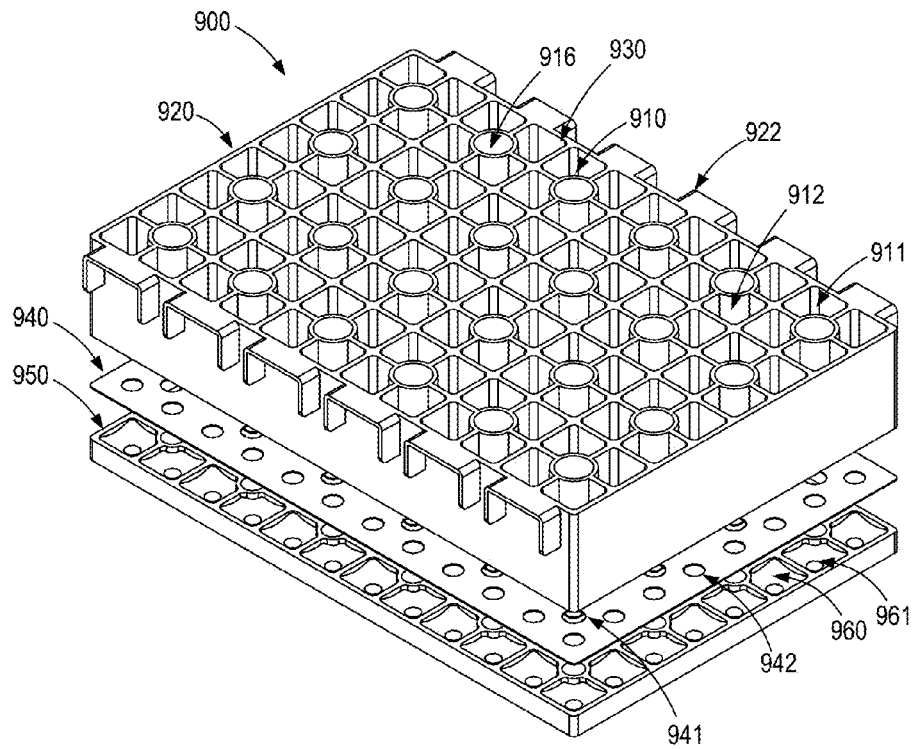
FIG. 46 is an exploded view of the well plate assembly of FIG. 42.
Figure 47:
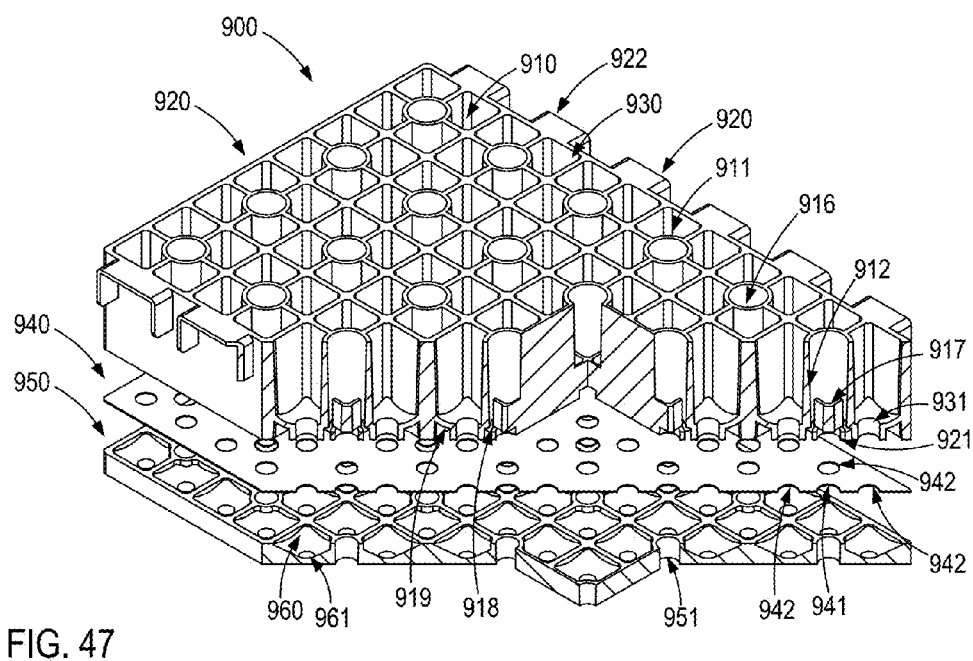
FIG. 47 is a cross-sectional view of the well plate assembly in FIG. 46 in an exploded configuration.
Figure 48:
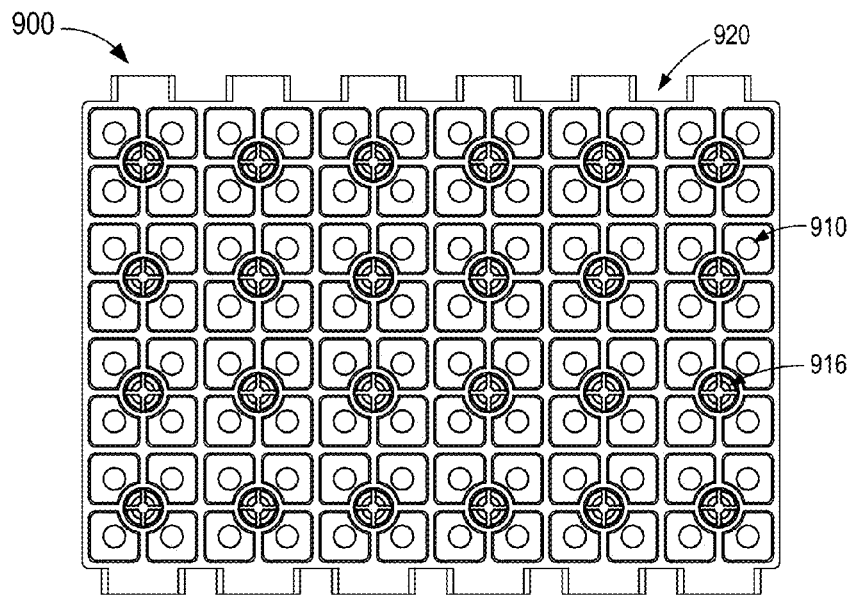
FIGS. 48 and 49 are top views of a top plate and a bottom plate, respectively, included in the well plate assembly of FIG. 42.
Figure 49:
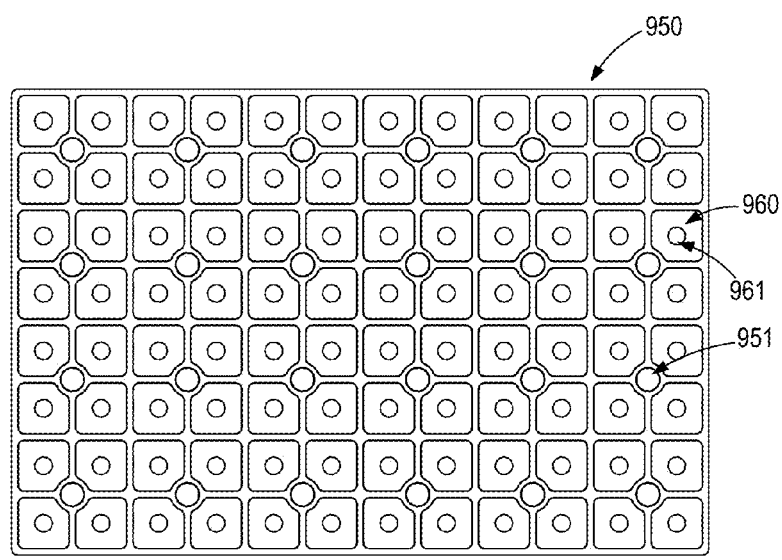
Figure 50:
FIG. 50 is a cross-sectional side view of the bottom plate included in the well plate assembly of FIG. 42.

The membrane 940 of the plate assembly 900 is configured to be disposed between the top plate 920 and the bottom plate 950 of the plate assembly 900 (see e.g., FIGS. 46 and 47) when the top plate 920 and the bottom plate 950 are coupled together. The membrane 940 can be formed from and/or can be arranged as a substantially planar microporous sheet. In some embodiments, the membrane 940 can be formed with a material such that the membrane 940 is a barrier to the passage of cells, but allows liquid to pass through with little impedance, such as those described above with reference to the membrane 840 in FIG. 39. As shown in FIGS. 46 and 47, the membrane 940 defines a set of drain openings 941 and a set of well openings 942. The arrangement of the plate assembly 900 can be such that when the membrane 940 is disposed between the top plate 920 and the bottom plate 950 (e.g., when the top plate 920 is coupled to the bottom plate 950), the drain openings 941 are substantially aligned with and/or are coaxial with a corresponding drain column 916 and the well openings 942 are substantially aligned with and/or are coaxial with a corresponding well 910. Thus, the arrangement of the drain openings 941 and the well openings 942 can allow a sample and/or a portion thereof to pass through the membrane 940, as described in further detail herein. Moreover, the membrane 940 can have a size and shape that is associated with, for example, the 96 well configuration of the top plate 920.

Figure 51:
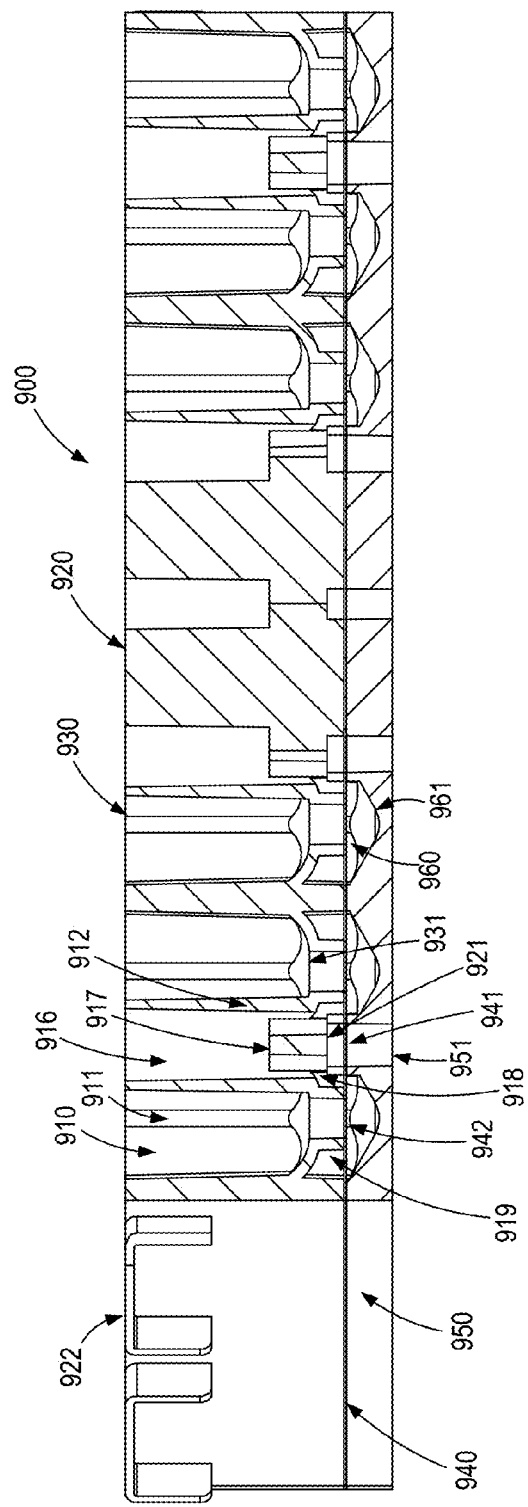
FIG. 51 is cross-sectional view of the well plate assembly in FIG. 46.

The bottom plate 950 of the plate assembly 900 includes an inner surface that defines and/or forms a reservoir 960 having a recessed portion 961, as shown in FIGS. 46, 47, 50, and 51. In addition, the bottom plate 950 defines a set of drain openings 951. As described above, the bottom plate 950 is configured to be coupled to the top plate 920 via any suitable coupling method. As shown in FIGS. 44, 46, and 51, the bottom plate 950 can be coupled to the top plate 920 such that the fluid reservoirs 960 are substantially aligned with and/or coaxial with a corresponding well 910 of the top plate 920 (i.e., each fluid reservoir 960 is aligned with a different well 910), while the drain openings 951 are substantially aligned with and/or coaxial with a corresponding drain column 916 (i.e., each drain opening 951 is aligned with a different drain column 916). With the membrane 940 disposed between the top plate 920 and the bottom plate 950 and with the membrane 940 substantially aligned with the top plate 920 (as described above), the drain openings 951 of the bottom plate 950 can also be aligned with and/or coaxial with the drain openings 941 defined by the membrane 940 and the reservoirs 960 of the bottom plate 950 can also be substantially aligned with and/or coaxial with the well openings 942 defined by the membrane 940, as described above with reference to the plate assembly 800 in FIGS. 34-41. In addition, the plate assembly 900 can be arranged such that the membrane 940 physically separates the reservoir 960 from the channel 919 circumscribing the tapered portion 913 of the inner walls 912 defining the corresponding or aligned well 910. Thus, with the membrane 940 being permeable, the membrane 940 can allow, for example, a fluid disposed in the reservoir 960 to pass through the membrane 940 to be disposed in the channel 919 and in turn, with the channel 919 in fluid communication with the drain column 916 (via the opening 918 described above), the fluid can pass through the channel 919 to be disposed in the drain column 916.

In use, a sample can be delivered through the top opening 930 of any suitable number of wells 910 defined by the plate assembly 900. Under the force of gravity, at least a portion of the sample can flow through the well 910 to be disposed in the corresponding reservoirs 960, as described in detail above with reference to the plate assembly 800. With the samples disposed in the plate assembly 900, the plate assembly 900 can be coupled to the tray assembly 995 (e.g., via the coupling portion 932 of the coupling tray 935 and the flange 922 of the top portion 920 of the plate assembly 900) and the lid 914 can be disposed about the coupling tray 935 (see e.g., FIG. 45). The tray assembly 995 can then be disposed in, for example, a centrifuge device. Although the sample is described above as being transferred to the wells 910 prior to the plate assembly being coupled to the tray assembly 995, in other instances, the plate assembly 900 can be coupled to the tray assembly 995 and subsequently, the sample can be transferred to the wells 910. In such instances, the sample can be transferred to the wells 910 prior to the tray assembly 995 being disposed in the centrifuge device or after being disposed in the centrifuge device.

While being centrifuged, the remaining portion of the sample in well 910 is drawn to a bottom portion of the well 910 and into the reservoir 960 of the bottom plate 950. As described above, the centrifugation of the sample, can be such that the wash liquid separates from the cells by virtue of the greater density of the cells, and as such, the pressure generated by centripetal acceleration acting on the column of liquid in well 910 is sufficient for the liquid to be propelled through a portion of the membrane 940 and into the channel 919 defined by the inner walls 912. The wash liquid can then pass through the opening 918 (FIGS. 47 and 51) and into the drain column 916. As shown, for example, in FIGS. 43 and 44, the plate assembly 900 can include a set of caps 913 or the like that can each be disposed in a drain column 916 that can, for example, prevent the wash liquid from passing over the divider 917 and thereby generating the risk of contaminating the channel 919 of adjacent wells. Contaminating liquid from adjacent wells 910 entering the channel 919 could result in the contamination of the sample in the reservoir 960 of that well 910 in the event that contaminating liquid flows in the reverse direction through the membrane 940 when the liquid levels in the well 910 and in the channel 919 have reached near equilibrium. Although the caps 913 are shown as being separate components, in other embodiments, the caps 913 can be formed, for example, as part of the top plate 920. For example, the caps 913 can be formed integral with the dividers 917 and/or otherwise formed by the walls 912 of the top plate 920.

As such, the wash liquid can then flow through the drain hole 921 defined by the top plate 920, through the drain hole 941 defined by the membrane 940, and through the drain hole 951 of the bottom plate 950, thereby flowing out of the plate assembly 900. With the plate assembly 900 coupled to the tray assembly 995, the wash liquid and/or effluent can flow through a drain portion 927 of the coupling tray 935 and into an inner volume 933 (e.g., the collection chamber) defined by the collection tray 955. While the drain tray is not shown in FIGS. 42-51, in some instances, a drain protrusion of the drain tray can engage a ball valve 956 (see e.g., FIG. 44), and the wash liquid can flow through an opening, which is otherwise obstructed by the ball valve 956, and removed by, for example, a flexible hose disposed in and/or defining a channel of the drain tray. The arrangement of the drain tray (not shown) is such that the wash liquid can then flow within the channel and through an opening to be discarded in any suitable biologically safe manner.

As described above, centripetal force and/or acceleration directly opposes the flow of liquid out of the reservoir 960 and through membrane 940, thus forcing the cells away from the membrane 940 and into the recessed portion 961 of the reservoir 960. Thus, the cells or particles within the well 910 and/or the reservoir 960 can collect or "pellet" in, for example, the recessed portion 961 of the reservoir 960 (see e.g., FIG. 51). Moreover, as described above, the size of the pores in the membrane 940 can be sufficiently small as to not allow the cells to pass up through the membrane 940 with the wash liquid during centrifugation. In this manner, centrifugal processes can be serially performed on the sample with substantially less sample loss than would otherwise be possible. Although the method of using the plate assembly 900 and the tray assembly 995 in a centrifugal process for testing has been briefly described, it should be understood that, while, the plate assembly 900 includes and/or defines more wells 910 than the plate assembly 800, the centrifuge process described above with reference to the plate assembly 800 can apply to a similar centrifuge process of the plate assembly 900. Thus, the centrifuge process was not described in detail above.

Figure 52:
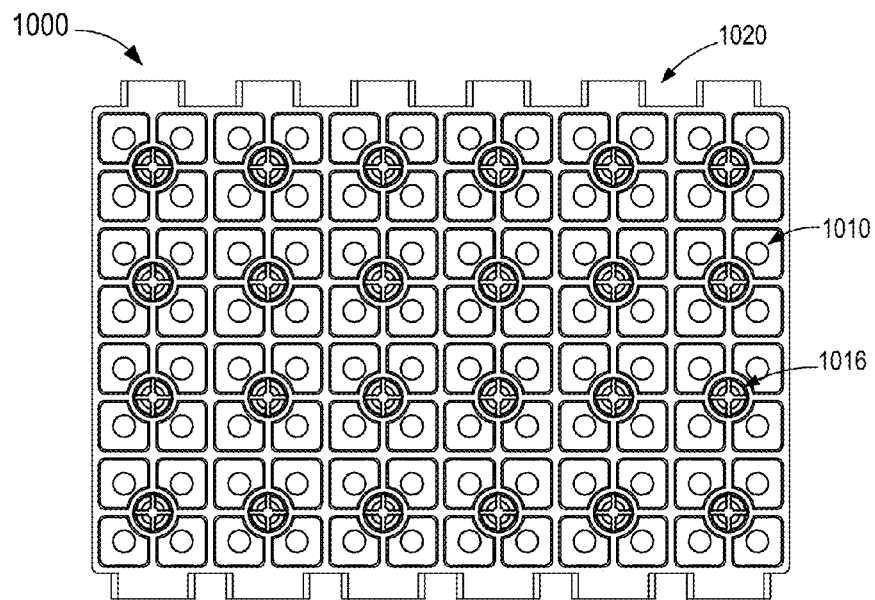
FIGS. 52 and 53 are top views of a top plate and a bottom plate, respectively, included in a well plate assembly, according to an embodiment.
Figure 53:
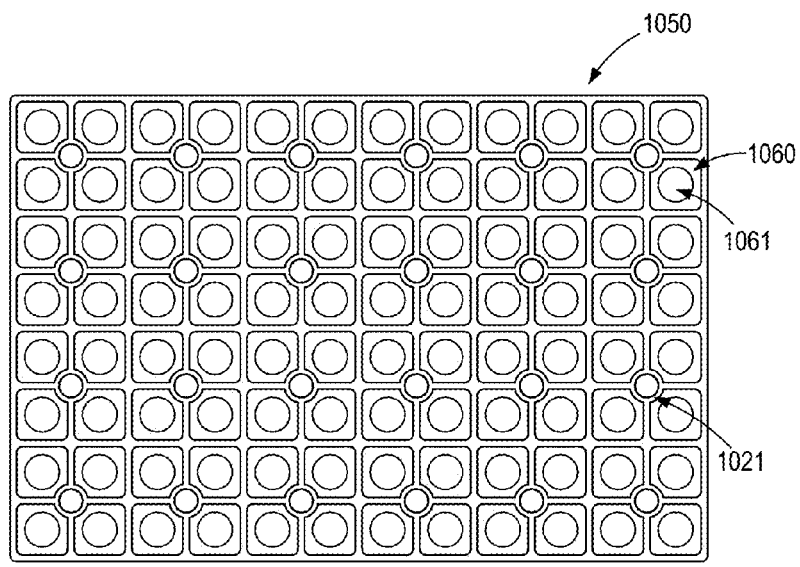
Figure 54:
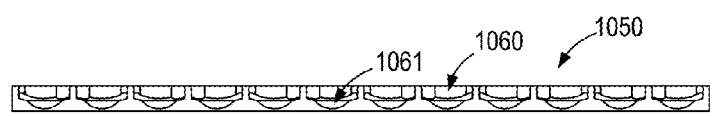
FIG. 54 is a cross-sectional side view of the bottom plate included in the well plate assembly of FIGS. 52 and 53.

Although the plate assembly 900 has been particularly shown and described above, in other embodiments, a plate assembly can be configured to include and/or define a set of wells, openings, reservoirs, channels, walls, etc. in any suitable arrangement. For example, while the plate assembly 900 is shown in FIGS. 48-51 as including the top plate 920 in which the wells 910 are substantially square and the drain column 916 is substantially round, in other embodiments, a plate assembly can include a top plate with any suitable configuration. Similarly, while the plate assembly 900 is shown in FIGS. 48-51 as including the bottom plate 920 having, for example, substantially V-shaped reservoirs 960, in other embodiments, a plate assembly can include a bottom plate with any suitable configuration. For example, FIGS. 52-54 illustrate a portion of a well plate assembly 1000 according to another embodiment. The portion of the well plate assembly 1000 (also referred to herein as "plate assembly") can be substantially similar in form and function as the plate assembly 900 described above with reference to FIGS. 42-51. Thus, similar portions of the plate assembly 1000 and/or its use are not described in further detail herein. The plate assembly 1000 can differ from the plate assembly 900, however, in the arrangement of, for example, a top plate 1020 and a bottom plate 1050. For example, as shown in FIG. 54, while the bottom plate 950 was shown and described as defining reservoirs 960 with a substantially V-shaped cross-sectional area, the bottom plate 1050 defines multiple reservoirs 1060 with a substantially U-shaped cross-sectional area. Accordingly, as shown in FIGS. 52 and 53, the top plate 1020 of the well plate assembly 1000 can have a set of wells 1010 that define a bottom opening 1031 that is substantially larger than the bottom opening 931 defined by the top plate 920. Moreover, the bottom opening 1031 can have a size and/or diameter such that the bottom opening 1031 is substantially unobstructed by a drain column 1016.

Figure 55:
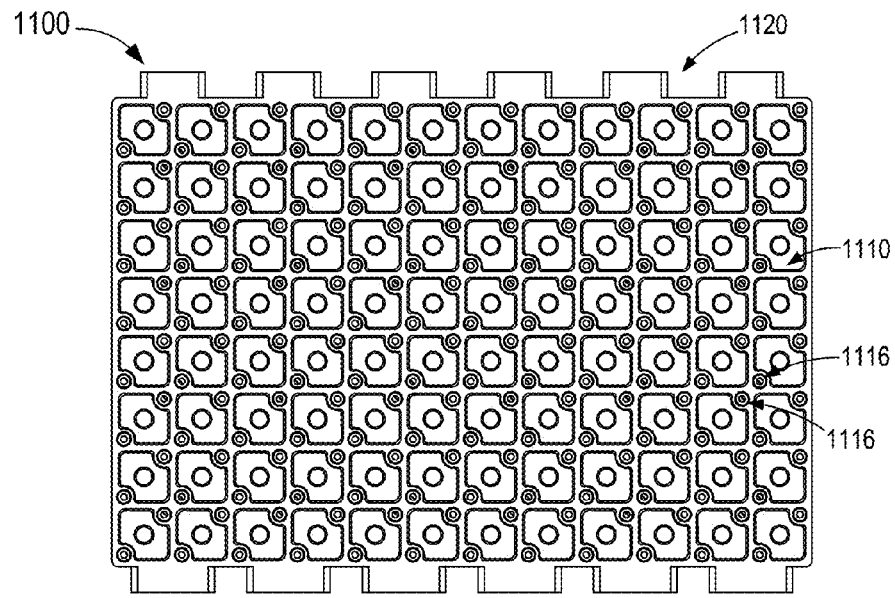
FIGS. 55 and 56 are top views of a top plate and a bottom plate, respectively, included in a well plate assembly, according to an embodiment.
Figure 56:
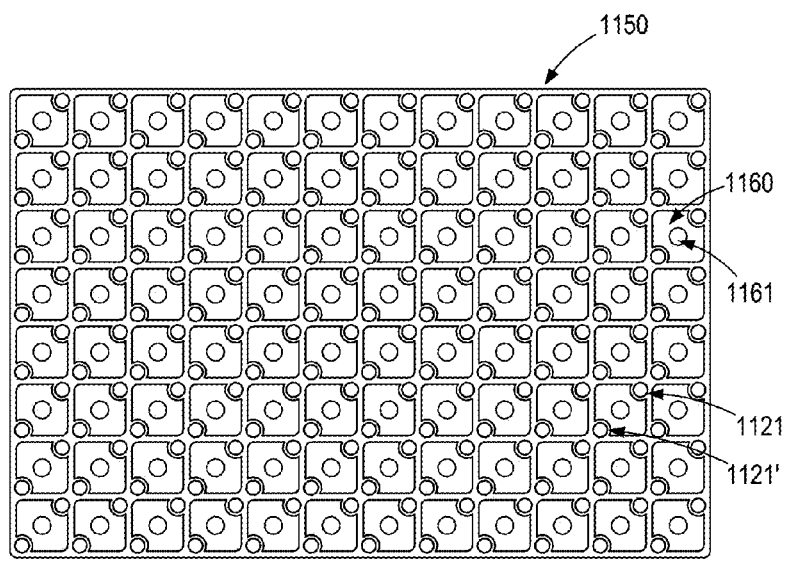
Figure 57:
FIG. 57 is a cross-sectional side view of the bottom plate included in the well plate assembly of FIGS. 55 and 56.

FIGS. 55-57 illustrate a portion of a well plate assembly 1100 according to another embodiment. The portion of the well plate assembly 1100 (also referred to herein as "plate assembly") can be substantially similar in form and function as the plate assembly 900 described above with reference to FIGS. 42-51. Thus, similar portions of the plate assembly 1100 and/or its use are not described in further detail herein. The plate assembly can differ from the plate assembly 900, however, in the arrangement of, for example, a top plate 1120 and/or a bottom plate 1150. For example, as shown in FIGS. 55 and 56, while the top plate 920 is shown and described above as including a set of wells 910, each of which were in fluid communication with a drain column 916, the top plate 1120 defines a set of wells 1110 that are each in fluid communication with two distinct drain columns 1116 and 1116'. Thus, in a similar manner as described above, each well 1110 of the well plate assembly 1100 can receive a sample and can undergo a centrifugal process such that a wash liquid or the like of the sample passes through a membrane (not shown) and into the drain column 1116 or the drain column 1116'. As shown in FIG. 57, in some embodiments, the bottom plate 1150 defines a set of reservoirs 1160. In some embodiments, the bottom plate 1150 can be substantially similar to or the same as the bottom plate 950 described above with reference to, for example, FIG. 50.

Figure 58:
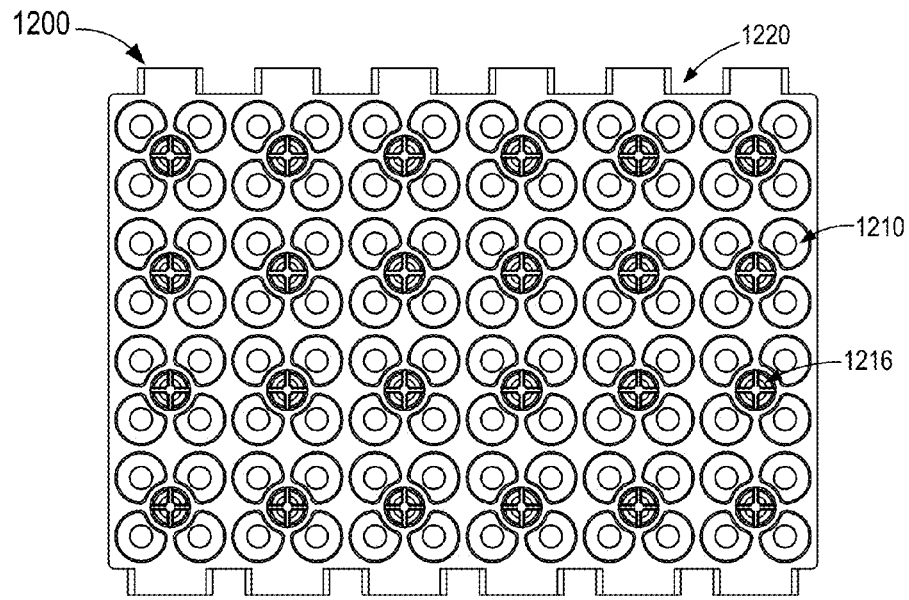
FIGS. 58 and 59 are a top view and a bottom view, respectively, of a top plate included in a well plate assembly, according to an embodiment.
Figure 59:
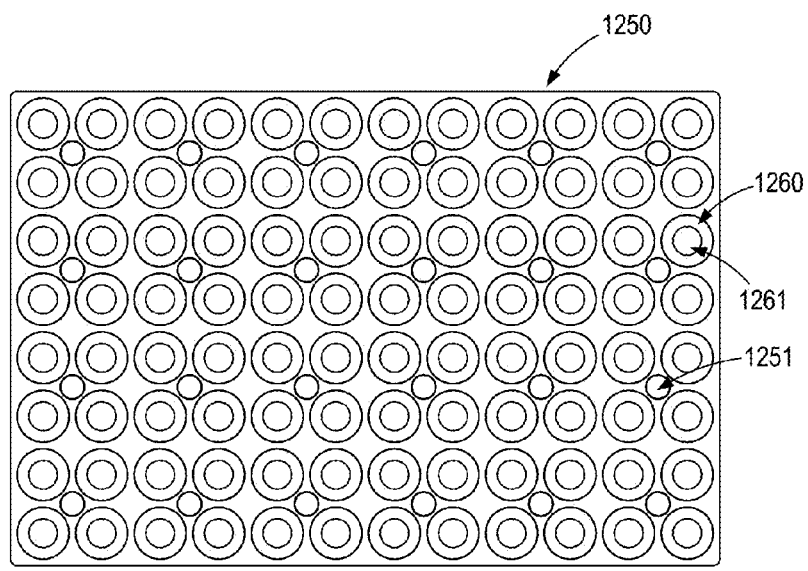
Figure 60:
FIG. 60 is a cross-sectional side view of a bottom plate included in the well plate assembly of FIGS. 58 and 59.

FIGS. 58-60 illustrate a portion of a well plate assembly 1200 according to another embodiment. The portion of the well plate assembly 1200 (also referred to herein as "plate assembly") can be substantially similar in form and function as the plate assembly 900 described above with reference to FIGS. 42-51. Thus, similar portions of the plate assembly 1200 and/or its use are not described in further detail herein. The plate assembly 1200 can differ from the plate assembly 900, however, in the arrangement of, for example, a top plate 1220 and/or a bottom plate 1250. For example, as shown in FIGS. 58 and 59, while the top plate 920 is shown and described above as including a set of wells 910 that are each substantially square, the top plate 1220 defines a set of wells 1210 that are each substantially cylindrical. Thus, in a similar manner as described above, each well 1210 of the well plate assembly 1200 can receive a sample and can undergo a centrifugal process such that a wash liquid or the like of the sample passes through a membrane (not shown) and into a drain column 1216. As shown in FIG. 60, the bottom plate 1250 defines a set of reservoirs 1260 that can have a substantially broad U-shaped cross-sectional area that can, for example, correspond to the cylindrical wells 910.

Figure 61:
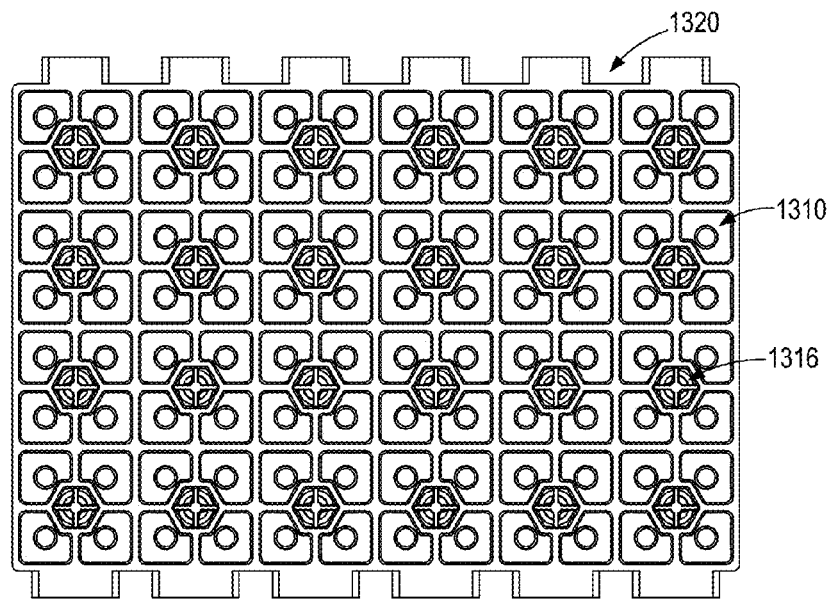
FIGS. 61 and 62 are top views of top plates included in different well plate assemblies, each according to different embodiments.

Although the top plates 920, 1020, 1120, and 1220 are shown and described above as including a set of drain columns 916, 1016, 1116, and 1216, respectively, that have a substantially cylindrical shape (i.e., circular cross-sectional shape when viewing top-down), in other embodiments, a top plate can define a set of drain columns having any suitable top-down cross-sectional shape. For example, FIG. 61 illustrates a top plate 1320 of a well plate assembly according to another embodiment. The top plate 1320 can be substantially similar in form and function as the top plate 920 described above with reference to FIGS. 42-51. Thus, similar portions of the plate assembly 1320 and/or its use are not described in further detail herein. The plate assembly 1320 can differ from the plate assembly 920, however, in the arrangement of, for example, a set of wells 1310 and/or a set of drain columns 1316. For example, as shown in FIG. 61, while the top plate 920 is shown and described above as including a set of drain columns 916 that are substantially cylindrical and/or annular, the top plate 1320 defines a set of drain columns 1316 that have a hexagonal cross-sectional shape, which in turn, can modify at least one surface defining each well 1310. In this manner, the top plate 1320 can function in a substantially similar manner as described above with reference to the top plate 920.

Figure 62:
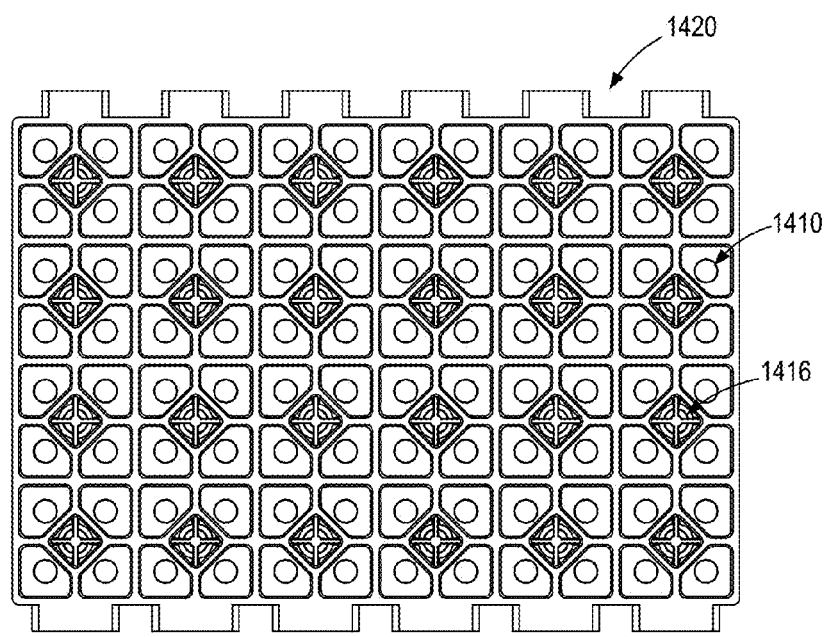

By way of another example, FIG. 62 illustrates a top plate 1420 of a well plate assembly according to another embodiment. The top plate 1420 can be substantially similar in form and function as the top plate 920 described above with reference to FIGS. 42-51. Thus, similar portions of the plate assembly 1420 and/or its use are not described in further detail herein. The plate assembly 1420 can differ from the plate assembly 920, however, in the arrangement of, for example, a set of wells 1410 and/or a set of drain columns 1416. For example, as shown in FIG. 62, while the top plate 920 is shown and described above as including a set of drain columns 1416 that are substantially cylindrical and/or annular, the top plate 1420 defines a set of drain columns 1416 that have a substantially diamond-shaped cross-sectional shape, which in turn, can modify at least one surface defining each well 1410. In this manner, the top plate 1420 can function in a substantially similar manner as described above with reference to the top plate 920.

Figure 63:
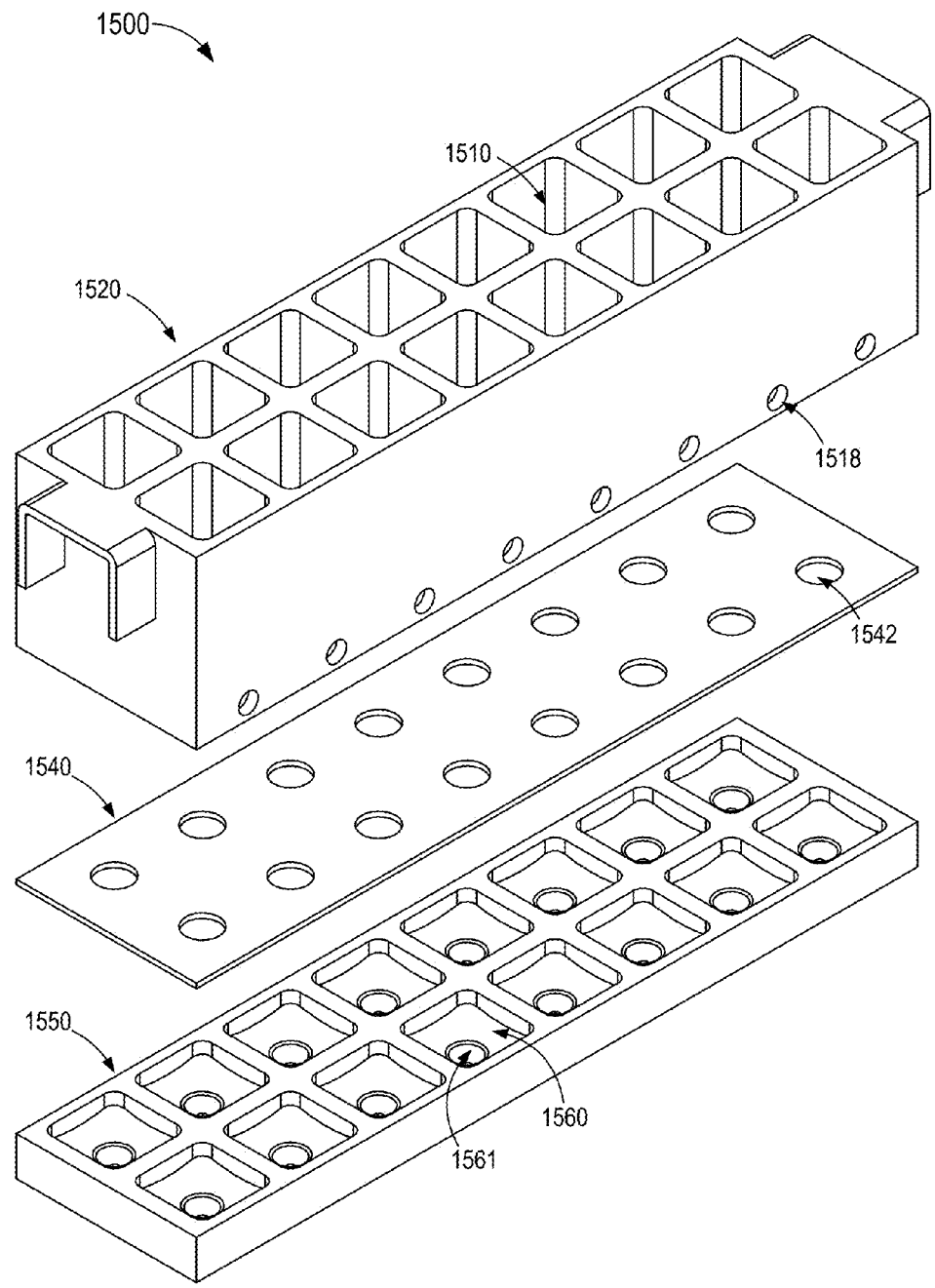
FIG. 63 is an exploded view of a well plate assembly according to an embodiment.
Figure 64:
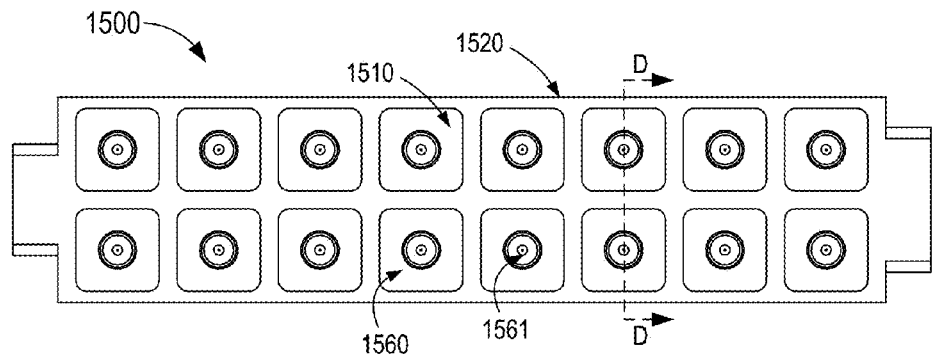
FIG. 64 is a top view of the well plate assembly of FIG. 63.
Figure 65:
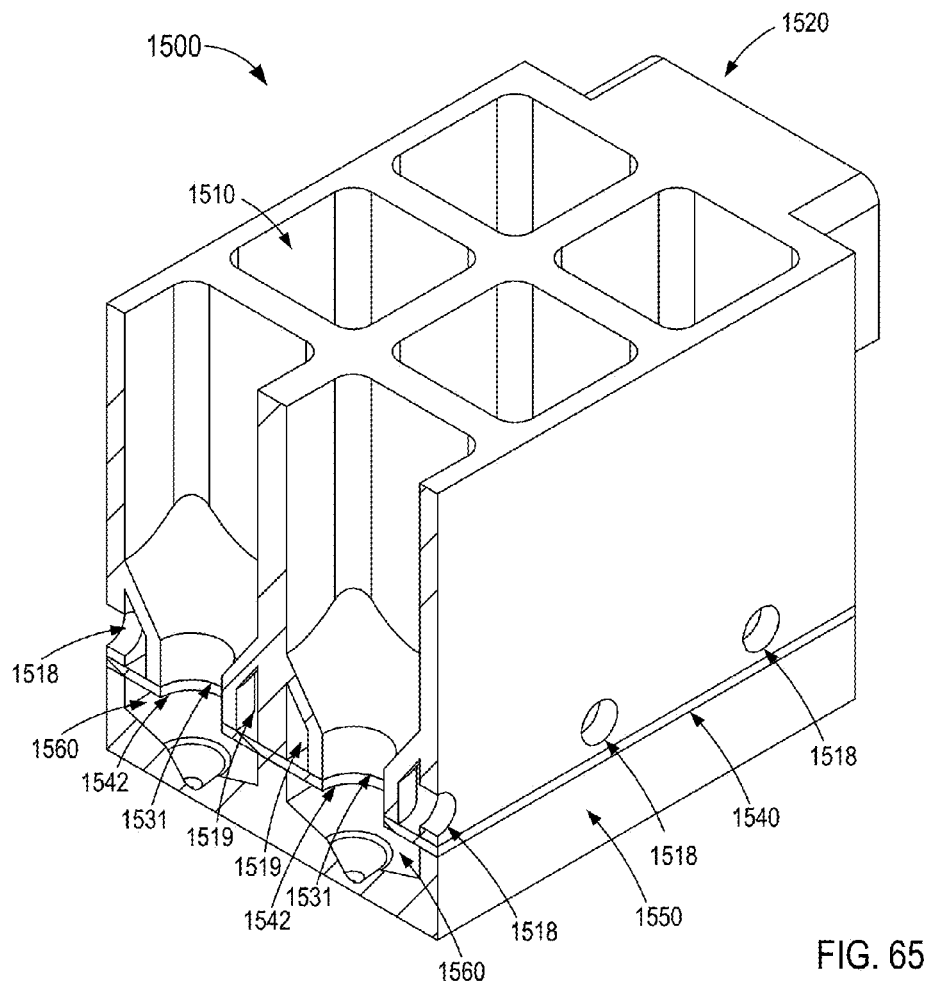
FIG. 65 is a cross-sectional view of the well plate assembly of FIG. 64 taken along the line D-D.

By way of another example, FIGS. 63-65 illustrate a well plate assembly 1500 according to another embodiment. The well plate assembly 1500 includes a top plate 1520, a bottom plate 1550, and a membrane 1540. In contrast to top plate 920 described above, the top plate 1520 defines a set of wells 1510, yet does not include a set of drain columns (e.g., such as the drain columns 916). For example, as shown in FIGS. 63 and 65, the top plate 1520 defines a set of side openings 1518 defined by, for example, a side of the top plate 1520 that can allow a fluid (e.g., a wash liquid) to drain from the well plate assembly 1520. For example, wash liquid that has passed through the membrane 1540 can drain out the side openings 518 and drain downward to be collected.

The top plate 1520 and bottom plate 1550 can be coupled together such that the membrane 1540 is disposed therebetween, as described in detail above with reference to the well plate assembly 800 of FIGS. 34-41. Each well 1510 of the top plate 1520 can define a bottom opening 1531, with each bottom opening 1531 being substantially aligned with and/or coaxial with a corresponding opening 1542 defined by the membrane 1540 (see e.g., FIGS. 63 and 65). As such, each well 1510 can be in fluid communication with a reservoir 1560 defined by the base plate 1550, in a similar manner as described in detail above with reference to, for example, the well plate assembly 800. Moreover, the arrangement of the top plate 1520 can be such that the top plate 1520 defines channels 1519 with each channel 1519 substantially circumscribing a portion of a corresponding well 1510. As shown in FIG. 65, each channel 1519 is in fluid communication with a side opening 1518 of the top plate 1520. Thus, as described in detail above with reference to other embodiments, the well plate assembly 1500 can be used in a centrifugal process such that cells of a sample remain disposed, for example, in a recessed portion of the reservoirs 1560 (e.g., due to centripetal acceleration) and a fluid (e.g., a wash liquid) separates from the cells (e.g., the sample) and is urged to pass up through the membrane 1540 (e.g., due to centrifugal acceleration). The fluid can then be urged to flow through the corresponding channels 1519 and the corresponding side openings 1518 to exit the well plate assembly 1500. In some embodiments, the fluid can exit the well plate assembly 1500 and pass through a tray assembly such as the tray assembly 895 described above with reference to FIGS. 34-41.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above. Furthermore, any portion of the apparatus and/or methods described herein may be combined in any combination, except mutually exclusive combinations. While certain embodiments have been described in detail above, it should be understood that various embodiments can share common features and such description applies equally to such features between embodiments. The embodiments described herein can include various combinations and/or sub-combinations of the functions, components, and/or features of the different embodiments described.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed is:

1. A method, comprising:
    disposing a test sample within a sample well of a well plate, the well plate including a top plate, a bottom plate having a reservoir, and a membrane disposed between the top plate and the bottom plate, the test sample including a wash liquid and a sample material;
    centrifuging the test sample such that a centripetal acceleration associated with the centrifuging draws the sample material away from the membrane and opposes a binding of the sample material to the membrane,
    the membrane configured to filter the wash liquid from the test sample during the centrifuging such that the wash liquid can pass from the reservoir defined by the bottom plate in a direction that directly opposes the centripetal acceleration during centrifuging, and is captured within a collection chamber in fluid communication with the reservoir via the membrane, such that wash liquid passes from the reservoir, through the membrane through a drain hole defined by the membrane, while the sample material remains within the reservoir.

2. The method of claim 1, wherein during the centrifuging, prior to the wash liquid being captured within the collection chamber, the wash liquid moves laterally in a plane of the membrane, and then moves in a direction of the centripetal acceleration and into the collection chamber.

3. The method of claim 1, wherein the wash liquid filtered through the membrane leaves the reservoir during the centrifuging without requiring subsequent aspiration of excess wash liquid from the sample well of the sample plate.

4. The method of claim 1, wherein the wash liquid filtered through the membrane leaves the reservoir during centrifuging without requiring removal of a supernatant trapping element from the sample well of the well plate.

5. The method of claim 1, wherein the collection chamber is disposed substantially beneath the well plate and coupled to the bottom plate of the well assembly.

6. The method of claim 1, wherein the collection chamber is disposed substantially beneath the well plate and removably coupled to the bottom plate of the well assembly.

7. The method of claim 1, further comprising:
    absorbing at least a portion of the filtered wash liquid collected within the collection chamber with a trapping membrane disposed within the collection chamber.

8. The method of claim 1, further comprising:
    absorbing at least a portion of the filtered wash liquid collected within the collection chamber with a trapping membrane disposed within the collection chamber; and
    neutralizing biohazards within the filtered wash liquid captured within the collection chamber.

9. The method of claim 1, wherein the sample material remaining within the reservoir forms a pellet.

10. A method, comprising:
    disposing each of a plurality of test samples within a different sample well from a plurality of sample wells of a well plate, the well plate including a top plate, a bottom plate and a membrane disposed between the top plate and the bottom plate, the bottom plate defining a plurality of reservoirs, each sample well from the plurality of sample wells in fluid communication with a reservoir from the plurality of reservoirs, each test sample from the plurality of test samples including a wash liquid and a sample material;

centrifuging the plurality of test samples such that a centripetal acceleration associated with the centrifuging draws the sample material within each sample well away from the membrane and opposes a binding of each sample material to the membrane, the membrane configured to filter the wash liquid from the test sample in each sample well from the plurality of sample wells during the centrifuging such that the wash liquid can pass from a respective reservoir from the plurality of reservoirs in a direction that directly opposes the centripetal acceleration during centrifuging, and is captured within a collection chamber in fluid communication with each reservoir from the plurality of reservoirs via the membrane, such that wash liquid passes from each respective reservoir, through the membrane through a respective drain hole defined by the membrane, while each sample material remains within the respective reservoir from the plurality of reservoirs.

11. The method of claim 10, wherein during the centrifuging, prior to the wash liquid from each sample well from the plurality of sample wells being captured within the collection chamber, the wash liquid moves laterally in a plane of the membrane, and then moves in a direction of the centripetal acceleration and into the collection chamber.

12. The method of claim 10, wherein the wash liquid from each sample well from the plurality of sample wells that is filtered through the membrane leaves the respective reservoir from the plurality of reservoirs during the centrifuging without requiring subsequent aspiration of excess wash liquid from the respective sample well from the plurality of sample wells of the sample plate.

13. The method of claim 10, wherein the wash liquid from each sample well from the plurality of sample wells that is filtered through the membrane leaves the respective reservoir from the plurality of reservoirs during centrifuging without requiring removal of a supernatant trapping element from the respective sample well from the plurality of sample wells of the well plate.

14. The method of claim 10, wherein the collection chamber is disposed substantially beneath the well plate and coupled to the bottom plate of the well assembly.

15. The method of claim 10, wherein the collection chamber is disposed substantially beneath the well plate and removably coupled to the bottom plate of the well assembly.

16. The method of claim 10, further comprising:
absorbing at least a portion of the filtered wash liquid collected within the collection chamber with a trapping membrane disposed within the collection chamber.

17. The method of claim 10, further comprising:
absorbing at least a portion of the filtered wash liquid collected within the collection chamber with a trapping membrane disposed within the collection chamber; and
neutralizing biohazards within the filtered wash liquid captured within the collection chamber.

18. The method of claim 10, wherein the sample material remaining within each reservoir from the plurality of reservoirs forms a pellet.

* * * * *